(12) United States Patent
Levengood

(10) Patent No.: US 11,541,128 B2
(45) Date of Patent: Jan. 3, 2023

(54) MULTI-DRUG ANTIBODY DRUG CONJUGATES

(71) Applicant: Seagen Inc., Bothell, WA (US)

(72) Inventor: Matthew R. Levengood, Bothell, WA (US)

(73) Assignee: Seagen Inc., Bothell, WA (US)

( * ) Notice: Subject to any disclaimer, the term of this patent is extended or adjusted under 35 U.S.C. 154(b) by 322 days.

(21) Appl. No.: 16/463,541

(22) PCT Filed: Dec. 14, 2017

(86) PCT No.: PCT/US2017/066504
§ 371 (c)(1),
(2) Date: May 23, 2019

(87) PCT Pub. No.: WO2018/112253
PCT Pub. Date: Jun. 21, 2018

(65) Prior Publication Data
US 2020/0129639 A1     Apr. 30, 2020

Related U.S. Application Data

(60) Provisional application No. 62/434,333, filed on Dec. 14, 2016.

(30) Foreign Application Priority Data

Jun. 13, 2017 (JP) .............................. JP2017-115832

(51) Int. Cl.
| | | |
|---|---|---|
| A61K 47/61 | (2017.01) | |
| A61K 31/4745 | (2006.01) | |
| A61K 31/704 | (2006.01) | |
| A61K 31/496 | (2006.01) | |
| A61K 47/68 | (2017.01) | |
| A61K 47/60 | (2017.01) | |

(52) U.S. Cl.
CPC ...... *A61K 47/6889* (2017.08); *A61K 31/4745* (2013.01); *A61K 31/496* (2013.01); *A61K 31/704* (2013.01); *A61K 47/60* (2017.08); *A61K 47/61* (2017.08); *A61K 47/6803* (2017.08); *A61K 47/6809* (2017.08); *A61K 47/6817* (2017.08); *A61K 47/6849* (2017.08); *A61K 47/6883* (2017.08)

(58) Field of Classification Search
CPC .............. A61K 47/6889; A61K 47/61; A61K 47/6883; A61K 47/60; A61K 47/6803; A61K 47/6817; A61K 47/6809; A61K 47/6849; A61K 31/4745; A61K 31/704
USPC .................................................... 424/133.1
See application file for complete search history.

(56) References Cited

U.S. PATENT DOCUMENTS

| | | |
|---|---|---|
| 4,816,397 A | 3/1989 | Boss |
| 4,816,567 A | 3/1989 | Cabilly |
| 5,225,539 A | 7/1993 | Winter |
| 5,585,089 A | 12/1996 | Queen |
| 5,672,662 A | 9/1997 | Harris et al. |
| 5,757,078 A | 5/1998 | Matsuda et al. |
| 6,077,939 A | 6/2000 | Wei et al. |
| 7,498,298 B2 | 3/2009 | Doronina |
| 7,659,241 B2 | 2/2010 | Senter |
| 8,163,888 B2 | 4/2012 | Steeves |
| 8,257,706 B2 | 9/2012 | Mcdonagh |
| 9,000,130 B2 | 4/2015 | Bhakta et al. |
| 11,103,593 B2 | 8/2021 | Lyon et al. |
| 2006/0292616 A1 | 12/2006 | Neely et al. |
| 2008/0311134 A1 | 12/2008 | Junutula et al. |
| 2009/0136526 A1 | 5/2009 | Mcdonagh |
| 2009/0148942 A1 | 6/2009 | Mcdonagh |
| 2011/0256157 A1 | 10/2011 | Howard |
| 2013/0309256 A1 | 11/2013 | Lyon |
| 2016/0263244 A1 | 9/2016 | Lin et al. |
| 2016/0310612 A1 | 10/2016 | Lyon et al. |
| 2022/0072146 A1 | 3/2022 | Lyon et al. |

FOREIGN PATENT DOCUMENTS

| | | |
|---|---|---|
| CN | 102036660 A | 4/2011 |
| EP | 0401384 A1 | 12/1990 |
| TW | 201400131 A | 1/2014 |
| TW | 201515662 A | 5/2015 |
| WO | 198601533 A1 | 3/1986 |
| WO | 198702671 A1 | 5/1987 |
| WO | 90/12874 A2 | 11/1990 |
| WO | 2005112919 A2 | 12/2005 |
| WO | 2007/011968 A2 | 1/2007 |
| WO | 2007/011968 A3 | 1/2007 |
| WO | 2005112919 A3 | 2/2007 |
| WO | 2007085930 A1 | 8/2007 |
| WO | 2009117277 A2 | 9/2009 |

(Continued)

OTHER PUBLICATIONS

Levengood et al., "Orthogonal cysteine protection enables homogeneous multi-drug antibody-drug conjugates," Angew. Chemie, 2016, 129(3):751-755.

(Continued)

*Primary Examiner* — Yan Xiao
(74) *Attorney, Agent, or Firm* — Morrison & Foerster LLP

(57) ABSTRACT

The present disclosure provides, inter alia, multi-drug Antibody Drug Conjugates (MD-ADCs) and Linking Assembly (LA) Units, that are constructed in a site-specific matter via 'orthogonal' deprotection and drug loading. Also provided are, Protected Linking Assembly Units, which allow for 'orthogonal' deprotection and construction of MD-ADCs and LA Units of the present disclosure.

15 Claims, 18 Drawing Sheets

Specification includes a Sequence Listing.

(56) References Cited

FOREIGN PATENT DOCUMENTS

| WO | 2009117277 A3 | 4/2010 |
|---|---|---|
| WO | 2010091150 A1 | 8/2010 |
| WO | 2011023883 A1 | 3/2011 |
| WO | 2012112708 A1 | 8/2012 |
| WO | 2013123152 A2 | 8/2013 |
| WO | 2013/173337 A2 | 11/2013 |
| WO | 2013/173337 A3 | 11/2013 |
| WO | 2013123152 A3 | 11/2014 |
| WO | 2015057699 A2 | 4/2015 |
| WO | 2015057876 A1 | 4/2015 |
| WO | 2015057699 A3 | 9/2015 |
| WO | WO 2016/175551 | 11/2016 |
| WO | 2016190770 A1 | 12/2016 |

OTHER PUBLICATIONS

Lidicky et al., "Anti-lymphoma efficacy comparison of Anti-Cd20 monoclonal antibody-targeted and non-targeted star-shaped polymer-prodrug conjugates," Molecules, 2015, 20(11):19849-19864.
Ma et al., "Targeted delivery of polyamidoamine-paclitaxel conjugate functionalized with anti-human epidermal growth factor receptor 2 trastuzumab," Int. J. Nanmed., 2015, 10:2173-2190.
Maruani et al., "A plug-and-play approach to antibody-based therapeutics via a chemoselective dual click strategy," Nature Communications, 2015, 6:6645.
Otis et al., "Dendrimer antibody conjugate to target and image HER-2 overexpressing cancer cells," Oncotarget, 2016, 7(24):36002-36013.
Supplementary European Search Report in EP Appln. No. 17879927.6, dated Jul. 9, 2020, 12 pages.
Wangler et al., "Antibody-dendrimer conjugates: the number, not the size of the dendrimers, determines the immunoreactivity," Bioconjugate Chemistry, 2008, 19(4):813-820.
International Search Report dated Apr. 30, 2018 corresponding to PCT/US2017/066504 filed Dec. 14, 2017, 7 pages.
Written Opinion of the International Search Authority dated Apr. 30, 2018 corresponding to PCT/US2017/066504 filed Dec. 14, 2017, 9 pages.
Burke, Patrick J. et al., "Optimization of a PEGylated Glucuronide-Monomethylauristatin E Linker for Antibody-Drug Conjugates," Mol Cancer Ther (Jan. 2017; published online first Nov. 9, 2016); 16(1):116-123.
Doronina, Svetlana O. et al., "Development of potent monoclonal antibody auristatin conjugates for cancer therapy," Nature Biotechnology (Jul. 2003; Published online Jun. 1, 2003); 21(7):778-.
Doronina, Svetlana O. et al., "Enhanced Activity of Monomethylauristatin F through Monoclonal Antibody Delivery: Effects of Linker Technology on Efficacy and Toxicity," Bioconjugate Chem. (2006; published on Web Dec. 22, 2005); 17(1):114-124.
Gaertner, Hubert F. et al., "Chemo-enzymic Backbone Engineering of Proteins," The Journal of Biological Chemistry (Mar. 11, 1994); 269(10):7224-7230.
Goodson, Robert J. et al., "Site-Directed PEGylation of Recombinant Interleukin-2 at its Glycosylation Site," Biotechnology (Apr. 1990); 8:343-346.
Jain, Nareshkumar et al., "Current ADC Linker Chemistry," Pharm Res (Mar. 11, 2015); 32(11):3526-3540.
Levengood, Matthew R. et al., "Orthogonal Cysteine Protection Enables Homogeneous Multi-Drug Antibody-Drug Conjugates," Angew. Chem. Int. Ed. (Jan. 16, 2017); 56(3):733-737.
Lewis, Timothy S. et al., "Abstract 688: Characterization and circumvention of drug resistance mechanisms in SGN-35-resistant HL and ALCL clonal cell lines," Experimental and Molecular Therapeutics (DOI: 10. 1158/1538-7445.AM2014-688 Published Oct. 2014); 5 pages.
Li, Fu et al., "Intracellular Released Payload Influences Potency and Bystander-Killing Effects of Antibody-Drug Conjugates in Preclinical Models," Cancer Res (May 1, 2016); 76(9):2710-2719.

Lyon, Robert P. et al., "Conjugation of Anticancer Drugs Through Endogenous Monoclonal Antibody Cysteine Residues," Methods in Enzymology (2012; ISSN 0076-6879, DOI: 10.1016/B978-0-12-416039-2.00006-9); 502:123-137.
Lyon, Robert P. et al., "Self-hydrolyzing maleimides improve the stability and pharmacological properties of antibody-drug conjugates," Nature Biology (Oct. 2014; published online Sep. 7, 2014); 32(10):1059-1062.
Malik, Farooq et al., "Polyethylene Glycol (PEG)-modified Granulocyte-Macrophage Colony-stimulating Factor (GM-CSF) with Conserved Biological Activity," Exp. Hematol. (accepted Feb. 27, 1992); 20:1028-1035.
Maruani, Antoine et al., "Dual modification of biomolecules," Org. Biomol. Chem. (2016; accepted Jun. 2, 2016); 14:6165-6178.
Puthenveetil, Sujiet et al., "Development of Solid-Phase Site-Specific Conjugation and Its Application toward Generation of Dual Labeled Antibody and Fab Drug Conjugates," Bioconjugate Chemistry (Mar. 4, 2016); 27:1030-1039.
Rose, Keith et al., "Preparation of Well-Defined Protein Conjugates Using Enzyme-Assisted Reverse Proteolysis," Bioconjugate Chem.; 2:154-159.
Schmidt, Michael M. et al., "A modeling analysis of the effects of molecular size and binding affinity on tumor targeting," Mol Cancer Ther (Oct. 12, 2009); 8(10):2861-2871.
Schwarz, Alexander et al., "[15] Enzymatic C-Terminal Biotinylation of Proteins," Methods in Enzymology (Copyright© 1990 by Academic Press, Inc.); 184:160-162.
Veronese, F.M. et al., "Surface Modification of Proteins. Activation of Monomethoxy-Polyethylene Glycols by Phenylchloroformates and Modification of Ribonuclease and Superoxide Dismutase," Applied Biochemistry and Biotechnology (1985; Accepted Nov. 13, 1984); 11:141-152.
Veronese, Francesco M., "Peptide and protein PEGylation: a review of problems and solutions," Biomaterials (2001; Accepted May 30, 2000); 22:405-417.
Wahl, Alan F. et al., "The Anti-CD30 Monoclonal Antibody SGN-30 Promotes Growth Arrest and DNA Fragmentation in Vitro and Affects Antitumor Activity in Models," Cancer Research (Jul. 1, 2002); 62:3736-3742.
Beidler, C.B. et al. (Dec. 1, 1988). "Cloning and High Level Expression of a Chimeric Antibody With Specificity for Human Carcinoembryonic Antigen," J. Immunol. 141(11):4053-4060.
Berter, M. et al. (May 20, 1988). "Escherichia coli Secretion of an Active Chimeric Antibody Fragment," Science 240:1041-1043.
Bowen, M.A. et al. (Dec. 1, 1993). "Functional Effects of CD30 on a Large Granular Lymphoma Cell Line, YT. Inhibition of Cytotoxicity, Regulation of CD28 and IL-2R, and Induction of Homotypic Aggregation," J. Immunol. 151 (11):5896-5906.
Burke, P.J. et al. (Jan. 2017, e-pub. Nov. 9, 2016). "Optimization of a PEGylated Glucuronide-Monomethylauristatin E Linker for Antibody-Drug Conjugates," Mol. Cancer Ther 16(1):116-123.
Chari, R.V.J. et al. (Jan. 1, 1992). "Immunoconjugates Containing Noveal maytansinoids: Promising Anticancer Drugs," Cancer Res. 52:127-131.
Francisco, J.A. et al. (Jun. 15, 2000). "Agonistic Properties and in Vivo Antitumor Activity of the Anti-CD40 Anibody SGN-14," Cancer Res. 60:3225-3231.
Frankel, A.E. et al. (2000). "Cell Surface Receptor-Targeted Therapy of Acute Myeloid Leukemia: A Review," Cancer Biother. Radiopharm. 15(5):459-476.
Hu, Q-Y. et al. (2016, e-pub. Jan. 2016). "Toward the Next Generation of Biomedicines by Site-Selective Conjugation," Chem. Soc. Rev. 45:1691-1719.
International Preliminary Report on Patentability, dated Jun. 18, 2019, for PCT Application No. PCT/US2017/066504, filed Dec. 14, 2017, 10 pages.
Jones, P. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th Ed. Public Health Service, National Institutes of Health, Bethesda MD., Table of Contents, 21 pages.

(56) References Cited

OTHER PUBLICATIONS

Kabat, E.A. et al. (Sep. 1980). "Origins of Antibody Complementarity and Specificity-Hypervariable Regions and the Minigene Hypothesis," J Immunology 125(3):961-969.

Kozbor, D. et al. (1983). "The Production of Monoclonal Antibodies From Human Lymphocytes," Immunology Today 4(3):72-79.

Liu, A.Y. et al. (May 1987). "Chimeric Mouse-Human IgG1 Antibody That Can Mediate Lysis of Cancer Cells," Proc. Natl. Acad. Sci. USA 84:3439-3443.

Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.

Morrison, S.L. (Sep. 1985). "Transfectomas Provide Novel Chimeric Antibodies," Science 229 (4719):1202-1207.

Murray.J.L. (Dec. 2000). "Monoclonal Antibody Treatment of Solid Tumors: A Coming of Age," Semin. Oncol. 27(Suppl. 1):64-70.

Nishimura, Y. et al. (Feb. 15, 1987). "Recombinant Human-Mouse Chimeric Monoclonal Antibody Specific for Common Acute Lymphocytic Leukemia Antigen," Cancer. Res. 47(4):999-1005.

Oi, V.T. et al. (1986). "Chimeric Antibodies," BioTechniques 4(3):214-221.

Olsson, L. et al. (1983), "Human-Human Monoclonal Antibody-Producing Hybridomas: Technical Aspects," Meth Enzymol. 92:3-16.

Page, B. et al. (Sep. 1993). "A New Fluorometric Assay for Cytotoxicity Measurements In-Vitro," Intl. J. of Oncology 3(3):473-476.

Shaw, D.R. et al. (Dec. 7, 1988). "Mouse/Human Chimeric Antibodies to a Tumor-Associated Antigen: Biologic Activity of the Four Human IgG Subclasses," J. Natl. Cancer Inst. 80(19):1553-1559.

Skehan, P. et al. (Jul. 4, 1990). "New Colorimetric Cytotoxicity Assay for Anticancer-Drug Screening," J. Nat'l Cancer Inst. 82(13):1107-1112.

Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.

Teng, N.N.H. et al. (Dec. 1983). "Construction and Testing of Mouse-Human Heteromyelomas for Human Monoclonal Antibody Production," Proc. Natl. Acad. Sci. USA. 80:7308-7312.

Trail, P.A. et al. (Jan. 1, 1997). "Effects of Linker Variation on the Stability, Potency, and Efficacy of Carcinoma-Reactive BR64-Doxorubicin Immunoconjugates," Cancer Research 57:100-105.

Trail, P.A. et al. (Jul. 9, 1993). "Cure of Xenografted Human Carcinomas by BR-96-Doxorubicin Immunoconjugates," Science 261(5118):212-215.

Verhoeyan, M. et al. (Mar. 25, 1988). "Reshaping Human Antibodies: Grafting an Antilysozyme Activity," Science 239:1534-1536.

Wood, C.R. et al. (Apr. 4, 1985). "The Synthesis and in vivo Assembly of Functional Antibodies in Yeast," Nature 314 (6010):446-449.

MULTI-DRUG ANTIBODY DRUG CONJUGATES

CROSS-REFERENCES TO RELATED APPLICATIONS

This application claims domestic priority under 35 U.S.C. § 119(e) to U.S. Provisional Application No. 62/434,333 filed on Dec. 14, 2016, and foreign priority under 35 U.S.C. § 119(a) to Japanese Patent Application No. 2017-115832, filed Jun. 13, 2017, which claims the benefit of priority to the U.S. Provisional Application 62/434,333 filed Dec. 14, 2016, the content of each are incorporated herein by reference for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

A sequence listing designated 4200-00111PC-ST25.txt of 12 KB created Dec. 12, 2017, is incorporated herein by reference.

BACKGROUND OF THE INVENTION

Antibody-drug conjugates (ADCs) combine the tumor targeting specificity of monoclonal antibodies with the potent cell-killing activity of cytotoxic warheads. There has been a surge of interest in designing new ADC formats due in part to the recent clinical success of ADCs, which includes the approvals of brentuximab vedotin (ADCE-TRIS™) in relapsed Hodgkin lymphoma and anaplastic large-cell lymphoma, and ado-trastuzumab mertansine (KADCYLA™) in HER2-positive metastatic breast cancer. Most of these new methodologies have focused on addressing some of the shortcomings of existing clinical molecules, such as heterogeneous drug loading, limited drug-linker stability, and warheads with activities that are restricted to a subset of cancer types. To enable improved ADCs, much notable advancement has been made in the field. These include site-specific drug-linker conjugation strategies that enable homogeneous loading, drug-linker attachment modalities with improved stability, potent new payloads, and linker strategies that utilize alternative release mechanisms.

Almost all effective cancer chemotherapies utilize complementary drug combinations that are designed to overcome differential drug sensitivities within heterogeneous tumor cell populations. That strategy has recently been applied to ADCs, which are now being tested in combination with unconjugated, clinically approved anticancer drugs. In addition, emerging clinical and preclinical data for ADCs has demonstrated that insensitivity to a particular ADC can be overcome through delivery of an alternative warhead by administering a separate ADC using the same antibody. Here, we disclose complementary drug payloads within a single ADC, which constitutes a significant advancement in the field of targeted drug delivery, by describing an accessible dual-cytotoxic drug conjugate technology for antibodies targeting cancer cell antigens. That technology, which is applicable for other targeting agents, demonstrates the first use of orthogonal thiol protecting groups for preparing ADCs which is not dependent on an engineered antibody. We present the first data demonstrating that multiple drug ADCs having dual conjugated drugs (MD-ADCs) exhibit enhanced in vitro and in vivo activities compared to conventional ADCs.

In one exemplification of the MD-ADC technology, two different, highly potent auristatin molecules with complementary physiochemical properties are conjugated to a single antibody that enhances ADC activity on heterogeneous cancer cell populations. Commonly employed auristatin drug-linkers, also referred to as auristatin Linking Assembly Units, include mc-MMAF (1), mc-vc-MMAF (2), and mc-vc-MMAE (3). The released drug from the mc-vc-MMAE drug linker, monomethyl auristatin E (MMAE), is cell-permeable and exhibits bystander activity, or the killing of neighboring antigen-negative cancer cells. However, MMAE is also a substrate for multiple drug resistant (MDR) exporters and thus has diminished activity on cells with high MDR expression. Conversely, MMAF and cys-mc-MMAF, released from mc-vc-MMAF and mc-MMAF ADCs respectively, are not susceptible to drug export and retain activity on MDR(+) cells but are minimally cell-permeable. Thus, they do not exhibit bystander activity and have little activity on antigen-negative tumor cells. Combining the features of both types of drugs could provide complementary activities on cancers, yielding ADCs with enhanced cytotoxicity profiles.

To date, only a single example of a MD-ADC has been reported, but this work was conducted on an antibody Fab fragment and required the genetic introduction of an engineered cysteine (eCys) residue to enable site-specific discrimination of conjugation sites (Puthenveetil et al. Bioconjugate Chem. (2016) 27(4): 1030-1039). A number of other approaches for the site-specific conjugation of two separate agents to an antibody have been presented (Maruani et al. Org. Biomol. Org. (2016) 14(26): 6165-6178), but most of these methods require specialized reagents including site-specific amino acid mutations or custom enzymes, and sometimes require two distinct conjugation handles. All of those factors increase the complexity of reagents required to generate and screen MD-ADCs. One such method utilized pyridazine-dione re-bridging of reduced native antibody disulfides followed by dual-Click functionalization to construct a largely homogeneous product, but this method was only used to create a fluorophore-drug antibody conjugate and consumed two conjugatable sites on the antibody, thus reducing potential total drug loading.

What is needed is a methodology (and ADCs) for incorporation of dual drugs into a single Linking Assembly Unit that requires only one conjugatable site for each Unit, and results in a homogeneous and site-specific loading of both drugs in a specified ratio. That approach should not be dependent on engineered antibodies requiring restrictive eCys sites or enzyme-mediated conjugations and should be applicable for drug combinations that can be screened on an array of antibodies, including commercial antibodies and hybridoma antibody libraries. The present disclosure addresses those and other needs.

BRIEF SUMMARY OF THE INVENTION

Provided herein are multi-drug antibody drug conjugates (MD-ADCs) comprising an antibody and one to eight covalently attached Linking Assembly Units (LA), wherein each of the up to eight covalently attached Linking Assembly Units are attached to a thiol produced by reduction of interchain disulfide linkages in the antibody and/or each of the covalently attached LA Units is attached to a thiol from an engineered cysteine residue, and wherein each of the covalently attached Linking Assembly Units has from two to four drug moieties, also referred to as Drug Units, attached thereto in which two of the Drug Units are different and an optional Partitioning Agent (Y). Specific embodiments of these MD-ADCs are provided in formulae (I), (II), (III) and (IV), as well as formulae (I*), (II*), (III*), and (IV*).

Also provided herein are Linking Assembly Units that are useful in the preparation of the MD-ADCs, which are embodied by formulae (Ia), (IIa), (IIIa) (IVa), and (XIIIa).

In another aspect, provided herein are Protected Linking Assembly Units (useful in preparing the Linking Assembly Units and the MD-ADCs), which are embodied by formulae (Ib), (IIb), (IIIb), (IVb), and (XIIIb) below.

In another aspect, provided herein are antibody conjugates having 1 to 8 orthogonally protected Linking Assembly Units.

In still other aspects, provided herein as pharmaceutical compositions, and methods for treating diseases, using the MD-ADCs described.

DETAILED DESCRIPTION OF THE INVENTION

General

Figure 1:
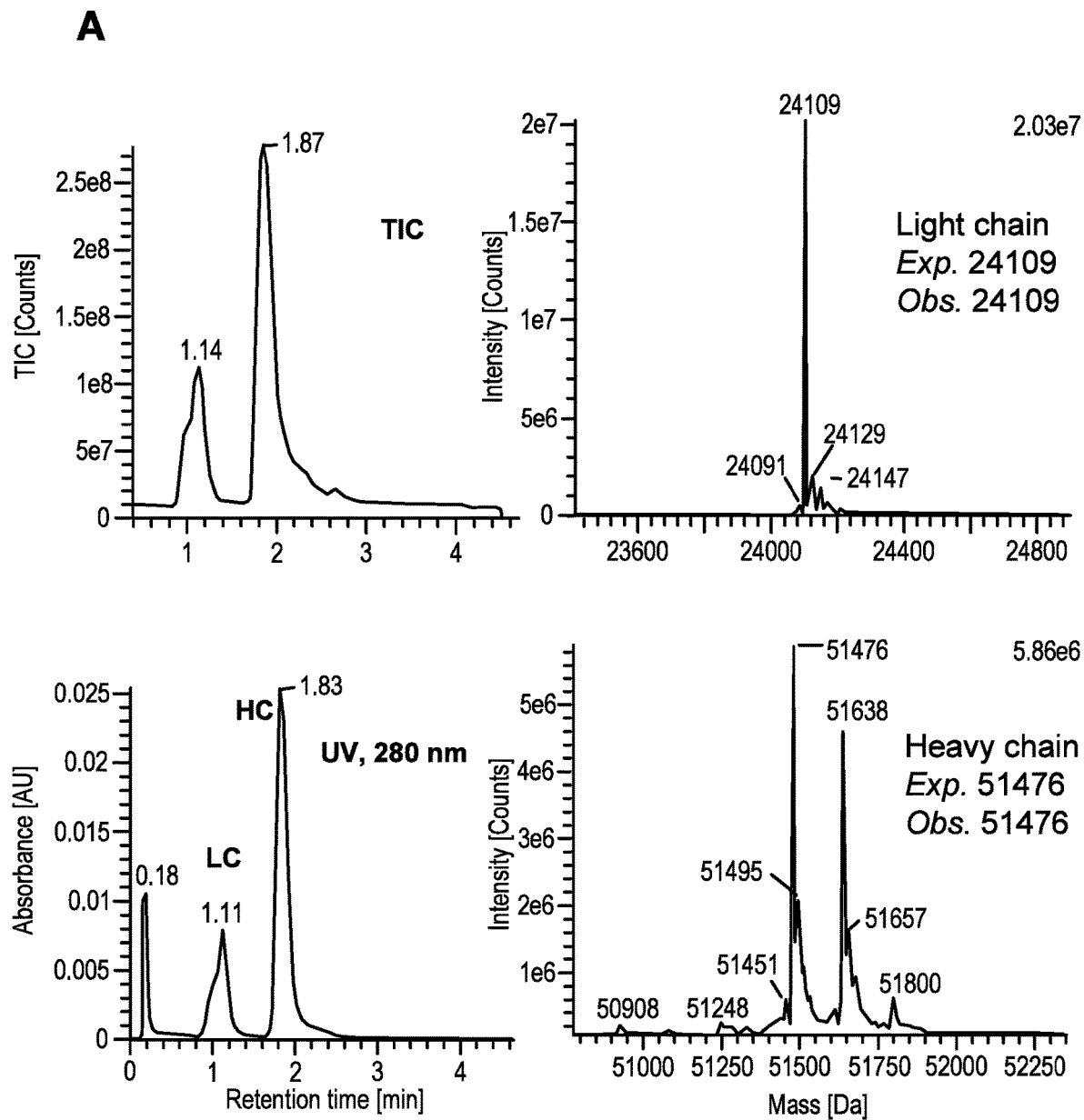
FIGS. 1A and 1B show the total ion chromatogram (TIC) and UV chromatogram (280 nm) after reverse-phase separation of light and heavy chain antibodies after conjugation (A) and after deprotection (B). The deconvoluted mass spectra for the main light and heavy chain species are shown to the right of the chromatograph, with the expected and observed masses shown. Note that multiple heavy chain mass species are present due to heterogeneity in the N-linked glycan. Only the G0 glycoform mass is noted for the heavy chain. LC=light chain, HC=heavy chain.
Figure 1:
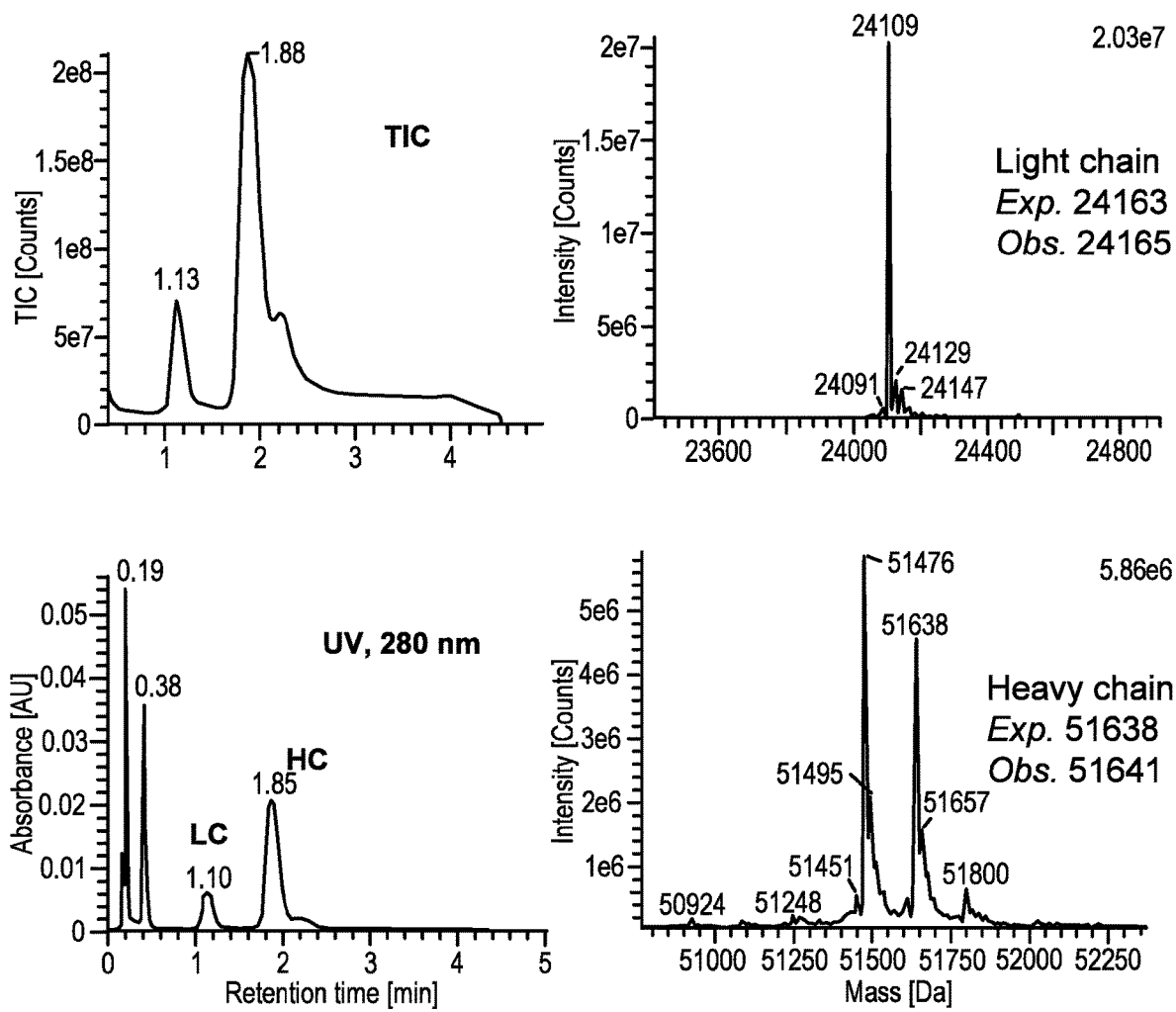

Provided herein are multi-drug antibody drug conjugates (MD-ADCs) that are constructed in a site-specific manner, leading to homogeneous drug loading (16 drug, 24 drug or 32 drug versions, for example) and which are prepared with antibodies that need not be engineered to introduce other natural or non-natural amino acids. Preparation of the MD-ADCs utilizes an orthogonal protection strategy for constructing the Linking Assembly Unit, which in an MD-ADC conjugates the dual drugs to the targeting antibody, in an approach that enables both high drug loading in a defined assembly, yet is flexible to allow for different stoichiometries of the drugs (ratios of Drug 1 to Drug 2). Still further, only a single attachment chemistry to the antibody is required for connection of each Drug Linker Assembly Unit, or orthogonally protected intermediate thereof, to the MD-ADC. The orthogonal protection is either in the Linking Assembly Unit of an Antibody-Linker Assembly Unit intermediate, prior to covalent attachment of one or both of $D^1$ and $D^2$ or a Multiple Drug Linker (MD-Linker) compound, which is used in the preparation of the MD-ADC, in which one or both of the $D^1$ and $D^2$ are covalently attached. A person of skill in the art will recognize that a Drug Linking Assembly Unit is a Linking Assembly Unit where Drug Units ($D^1$ and/or $D^2$) are covalently attached to the linking Assembly Unit, while an orthogonally protected Linking Assembly Unit is a Linking Assembly Unit where Protecting Groups ($P^1$ and $P^2$) are covalently attached to a Linking Assembly Unit. However, at times, this application refers to a Linking Assembly Unit without specifying Drug or orthogonally protected. Based on the context of the paragraph, it will be apparent to the skilled reader if the reference to Linking Assembly Unit refers to the Drug Linking Assembly Unit, the orthogonally protected Linking Assembly Unit, both, or an intermediate thereof.

The MD-ADCs provided herein further provide the advantage that multiple drugs can be successfully targeted to a particular binding site through conjugation to the same antibody which overcomes the difficulties associated with, for example, the delivery of an ADC1/ADC2 combination in which ADC1 has one of the two different drugs to be delivered and ADC2 has the other drug. In methods involving co-delivery of, for example, ADC1 and ADC2 (1) the conjugates compete for antigen binding, leading to large differences in drug delivery and activity on cells, particularly those with lower antigen copy number, or (2) are cleared at different rates leading to pharmacodynamic variability for exposures of the two drugs to the same targeted cells.

Definitions

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment have the requisite number of attachment sites for a drug-linker. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system. (see, e.g., Janeway et al., 2001, Immuno. Biology, 5th Ed., Garland Publishing, New York). An antibody includes any isotype (e.g., IgG, IgE, IgM, IgD, and IgA), or subclass (e.g., IgG1, IgG2, IgG3, IgG4, IgA1 and IgA2) thereof. The antibody is derivable from any suitable species. In some aspects, the antibody is of human or murine origin, and in other aspects an antibody is a human, humanized or chimeric antibody.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

An "intact antibody" is one which comprises an antigen-binding variable region as well as a light chain constant domain (CL) and heavy chain constant domains, $C_H1$, $C_H2$, $C_H3$ and $C_H4$, as appropriate for the antibody class. The constant domains are either native sequence constant domains (e.g., human native sequence constant domains) or amino acid sequence variant thereof.

An "antibody fragment" comprises a portion of an intact antibody comprising the antigen-binding or variable region thereof. In order to be of use in the present invention, the antibody fragment must have the requisite number of sites for attachment to a drug-linker, referred herein as a Drug Linking Assembly Unit. That is, antibody fragments of the present disclosure typically include all 8 cysteine residues that form the 4 disulfide bonds found in a natural antibody such that when fully reduced each cysteine residue is available for drug loading via the Linking Assembly Unit.

An "antigen" is an entity to which an antibody is capable of specifically binding.

The terms "specific binding" and "specifically binds" mean that the antibody or antibody fragment thereof will bind, in a selective manner, with its corresponding target antigen and not with a multitude of other antigens. Typically, the antibody or antibody derivative binds with an affinity of at least about $1 \times 10^{-7}$ M, and more typically $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The term "inhibit" or "inhibition of" means to reduce by a measurable amount, or to prevent entirely.

The term "therapeutically effective amount" refers to an amount of a Conjugate effective to treat a disease or disorder in a mammal. In the case of cancer, the therapeutically effective amount of the conjugate provides one or more of the following biological effects: reduction of the number of cancer cells; reduction of tumor size; inhibition (i.e., slow to some extent and preferably stop) of cancer cell infiltration into peripheral organs; inhibition of (i.e., slow to some extent and preferably stop) tumor metastasis; inhibition, to some extent, tumor growth; and/or relief to some extent one or more of the symptoms associated with the cancer. To the extent free drug released from the Conjugate inhibits growth and/or kills existing cancer cells, it is cytostatic and/or cytotoxic. For cancer therapy, efficacy in some aspects is typically measured by assessing the time to disease progression (TTP) and/or determining the response rate (RR).

Unless otherwise indicated by context, the term "substantial" or "substantially" refers to a majority, i.e. >50% of a population, of a mixture or a sample, typically more than 50%, 55%, 60%, 65%, 70%, 75%, 80%, 85%, 90%, 91%, 92%, 93%, 94%, 95%, 96%, 97%, 98%, or 99% of a population.

The terms "intracellularly cleaved" and "intracellular cleavage" refer to a metabolic process or reaction inside a cell on an MD-ADC, whereby the covalent attachment, between the Drug Unit ($D^1$ or $D^2$) and the Linking Assembly Unit (LA) or the antibody (Ab) is broken, resulting in free drug being dissociated from the MD-ADC, including degradant products thereof, inside the cell. The moieties resulting from that dissociation are thus intracellular metabolites.

The term "cytotoxic activity" refers to a cell-killing effect of a drug or MD-ADC or an intracellular metabolite of a MD-ADC. Cytotoxic activity is typically expressed by an $IC_{50}$ value, which is the concentration (molar or mass) per unit volume at which half the cells survive exposure to a cytotoxic agent.

The term "cytostatic activity" refers to an anti-proliferative effect other than cell killing of a cytostatic agent, or a MD-ADC having a cytostatic agent as its Drug Unit or an intracellular metabolite thereof wherein the metabolite is a cytostatic agent.

The term "cytotoxic agent" as used herein refers to a substance that has cytotoxic activity and causes destruction of cells. The term is intended to include chemotherapeutic agents, and toxins such as small molecule toxins or enzymatically active toxins of bacterial, fungal, plant or animal origin, including synthetic analogs and derivatives thereof.

The term "cytostatic agent" as used herein refers to a substance that has cytostatic activity e.g., inhibits a function of cells responsible for or that contributes to cell growth or multiplication. Cytostatic agents include inhibitors such as protein inhibitors, e.g., enzyme inhibitors.

The terms "cancer" and "cancerous" refer to or describe the physiological condition or disorder in mammals that is typically characterized by unregulated cell growth. A "tumor" comprises one or more cancerous cells.

An "autoimmune disease" herein is a disease or disorder arising from and directed against an individual's own tissues or proteins.

"Patient" as used herein refers to a subject to which an MD-ADC is administered. Examples of a "patient" include, but are not limited to, a human, rat, mouse, guinea pig, non-human primate, pig, goat, cow, horse, dog, cat, bird and fowl. Typically, a patient is a rat, mouse, dog, non-human primate or human. In some aspects, the patient is a human in need of an effective amount of an MD-ADC.

The terms "treat" or "treatment," unless otherwise indicated by context, refer to therapeutic treatment and prophylactic measures to prevent relapse, wherein the object is to inhibit or slow down (lessen) an undesired physiological change or disorder, such as, for example, the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" in some aspects also means prolonging survival as compared to expected survival if not receiving treatment. Those in need of treatment include those already with the condition or disorder and in some aspects further include those prone to have the condition or disorder.

In the context of cancer, the term "treating" includes any or all of: inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

The term "salt," as used herein, refers to organic or inorganic salts of a compound (e.g., a Drug, a Linking Assembly Unit, or a MD-ADC). In some aspects, the compound contains at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A salt may involve the inclusion of another molecule such as an acetate ion, a succinate ion or other counterion. The counterion may be any organic or inorganic moiety that stabilizes the charge on the parent compound. Furthermore, a salt has one or more than one charged atom in its structure. In instances where there are multiple charged atoms as part of the salt multiple counter ions are sometimes present. Hence, a salt can have one or more charged atoms and/or one or more counterions. A "pharmaceutically acceptable salt" is one that is suitable for administration to a subject as described herein and in some aspects includes salts as described by P. H. Stahl and C. G. Wermuth, editors, Handbook of Pharmaceutical Salts: Properties, Selection and Use, Weinheim/Züirich:Wiley-VCH/VHCA, 2002, the list for which is specifically incorporated by reference herein.

Unless otherwise indicated, the term "alkyl" by itself or as part of another term refers to an unsubstituted straight chain or branched, saturated hydrocarbon having the indicated number of carbon atoms (e.g., "—$C_1$-$C_8$ alkyl" or "—$C_1$-$C_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "—$C_1$-$C_8$ alkyl" groups include, but are not limited to, -methyl, -ethyl, -n-propyl, -n-butyl, -n-pentyl, -n-hexyl, -n-heptyl and -n-octyl; while branched —$C_1$-$C_8$ alkyls include, but are not limited to, -isopropyl, -sec-butyl, -isobutyl, -tert-butyl, -isopentyl, and -2-methylbutyl; the term "alkenyl" by itself or as part of another term refers to an unsaturated —$C_2$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexylenyl, 2-hexylenyl, -3-hexylenyl, the term "alkynyl" by itself or as part of another term refers to an unsaturated —$C_2$-$C_8$ alkyls having one or more triple bonds, for example, -acetylenyl, -propynyl, -1-butynyl, -2-butynyl, -1-pentynyl, -2-pentynyl and -3-methyl-1 butynyl.

Unless otherwise indicated, "alkylene," by itself of as part of another term, refers to a substituted or unsubstituted saturated or unsaturated branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene (—$CH_2CH_2$—), 1,3-propylene (—$CH_2CH_2CH_2$—), 1,4-butylene (—$CH_2CH_2CH_2CH_2$—), and the like. In some aspects, an alkylene is a branched or straight chain hydrocarbon (i.e., it is not a cyclic hydrocarbon). In other aspects, the alkylene is a saturated alkylene that typically is not a cyclic hydrocarbon.

Unless otherwise indicated, "aryl," by itself or as part of another term, means a substituted or unsubstituted monovalent carbocyclic aromatic hydrocarbon radical of 6-20 carbon (preferably 6-14 carbon) atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. An exemplary aryl group is a phenyl group.

Unless otherwise indicated, an "arylene," by itself or as part of another term, is an aryl group as defined above wherein one of the aryl group's hydrogen atoms is replaced with a bond (i.e., it is divalent) and can be in the ortho, meta, or para orientations as shown in the following structures, with phenyl as the exemplary group:

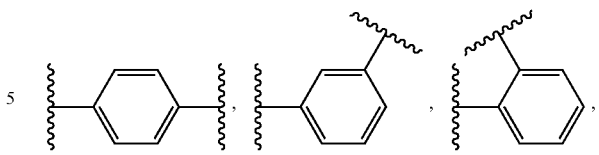

Unless otherwise indicated, a "$C_3$-$C_8$ heterocycle," by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Unless otherwise noted, the heterocycle is attached to its pendant group at any heteroatom or carbon atom that results in a stable structure. Representative examples of a $C_3$-$C_8$ heterocycle include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl.

Unless otherwise indicated, "$C_3$-$C_8$ heterocyclo", by itself or as part of another term, refers to a $C_3$-$C_8$ heterocycle group defined above wherein one of the heterocycle group's hydrogen atoms is replaced with a bond (i.e., it is divalent). In select embodiments, e.g., when a portion of the Linking Assembly Unit comprises a heterocyclo, the heterocyclo is a heterocycle group defined above wherein one or two of the heterocycle group's hydrogen atoms is replaced with a bond (i.e., the heterocyclo can be divalent or trivalent).

Unless otherwise indicated, a "$C_3$-$C_8$ carbocycle," by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Unless otherwise indicated, a "$C_3$-$C_8$ carbocyclo", by itself or as part of another term, refers to a $C_3$-$C_8$ carbocycle group defined above wherein another of the carbocycle groups' hydrogen atoms is replaced with a bond (i.e., it is divalent). In select embodiments, e.g., when a portion of the Linking Assembly Unit comprises a carbocyclo, the carbocyclo is a carbocycle group defined above wherein one or two of the carbocycle group's hydrogen atoms is replaced with a bond (i.e., the carbocyclo can be divalent or trivalent).

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. In preferred embodiments, a $C_1$ to $C_4$ heteroalkyl or heteroalkylene has 1 to 4 carbon atoms and 1 or 2 heteroatoms and a $C_1$ to $C_3$ heteroalkyl or heteroalkylene has 1 to 3 carbon atoms and 1 or 2 heteroatoms. In some aspects, a heteroalkyl or heteroalkylene is saturated.

Unless otherwise indicated, the term "heteroalkylene" by itself or as part of another substituent means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied. In certain aspects, e.g., when an Attachment Group or Tethering Group comprises a heteroalkylene, the heteroalkylene is a heteroalkyl group defined above wherein one or two of the heteroalkyl group's hydrogen atoms is replaced with a bond (i.e., the heteroalkylene can be divalent or trivalent).

"Substituted alkyl" and "substituted aryl" mean alkyl and aryl, respectively, in which one or more hydrogen atoms are each independently replaced with a substituent. Typical substituents include, but are not limited to, —X, —O$^-$, —OR, —SR, —S—, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=OXOR)$_2$, —P(=OXOR)$_2$, —PO$^-_3$, —PO$_3$H$_2$, —AsO$_2$H$_2$, —C(=O)X, —C(=S)R, —CO$_2$R, —CO$_2^"$, —C(=S)OR, C(=O)SR, C(=S)SR, C(=S)NR$_2$, or C(=NR)NR$_2$, where each X is independently a halogen: —F, —Cl, —Br, or —I; and each R is independently —H, —$C_1$-$C_{20}$ alkyl, —$C_6$-$C_{20}$ aryl, —$C_3$-$C_{14}$ heterocycle, a protecting group or a prodrug moiety. Typical substituents also include (=O). Alkylene, carbocycle, carbocyclo, arylene, heteroalkyl, heteroalkylene, heterocycle, and heterocyclo groups as described above are unsubstituted or similarly substituted. In some embodiments, substituents for "alkyl" and "alkylene" include —X, —O$^-$, —OR, —SR, —S—, —NR$_2$, —CX$_3$, —CN, —OCN, —SCN, —NRC(=O)R, —C(=O)R, —C(=O)NR$_2$, —SO$_3^-$, —SO$_3$H, or —CO$_2$R. In some embodiments, substituents for "aryl" "carbocyclic, "carbocyclo," "arylene," "heteroalkyl," "heteroalkylene," "heterocycle" and "heterocyclo" include —X, —O$^-$, —$C_1$-$C_{20}$ alkyl, —OR, —SR, —S$^-$, —NR$_2$, —CX$_3$, —CN, —OCN, —SCN, —NRC(=O)R, —C(=O)R, —C(=O)NR$_2$, —SO$_3$, —SO$_3$H, or —CO$_2$R.

As used herein, the term "free drug" refers to a biologically active drug moiety that is not covalently attached either directly or indirectly to any other portion of the MD-ADC or to a degradant product of a MD-ADC. Accordingly, free drug either refers to the drug prior to conjugation or as it exists immediately upon cleavage from a Drug Linking Assembly Unit of a MD-ADC via a release mechanism, which may be provided by the Optional Linking Groups in the MD-ADC, or to subsequent intracellular conversion or metabolism. In some aspects, the free drug will have the form H-D, which in some aspects exist as a charged moiety. The free drug is a pharmacologically active species capable of exerting the desired biological effect. In some aspects, the pharamacologically active species is the parent drug and in other aspects includes a component or vestige of a Linking Assembly Unit that has not undergone subsequent intracellular metabolism.

As used herein, the term "Partitioning Agent" is a structural unit that masks the hydrophobicity of particular Drug Units or Linking Assembly Units. In some aspects, a "Partitioning Agent" increases the hydrophilic character of a Drug Linking Assembly Unit. In other aspects, Partitioning Agents improve the pharmacokinetic properties of the Linking Assembly Units or MD-ADC's to which they are attached.

As used herein, the term "self-stabilizing linker assembly" refers to substituted succinimide) with a basic functional group proximal to a succinimide capable of catalyzing the hydrolysis of a carbonyl-nitrogen bond of the substituted succinimide. The hydrolysis of a substituted succinimide by the basic functional group forms a self-stabilized linker. Further details of the self-stabilizing linker assembly are described in WO 2013/173337. In some aspects the self-stabilizing linker assembly is MDPr, which has the structure disclosed herein.

As used herein the term "engineered cysteine residue" or "eCys residue" refers to a cysteine amino acid or a derivative thereof that is incorporated into an antibody. One or more eCys residues can be incorporated into an antibody, and typically, the eCys residues are incorporated in either the heavy chain or the light chain of an antibody. Generally, incorporation of an eCys residue into an antibody is performed by mutagenizing a nucleic acid sequence of a parent antibody to encode for one or more amino acid residues with a cysteine or a derivative thereof. Suitable mutations include replacement of a desired residue in the light or heavy chain of an antibody with a cysteine or a derivative thereof, incorporation of an additional cysteine or a derivative thereof at a desired location in the light or heavy chain of an antibody, as well as adding an additional cysteine or a derivative thereof to the N- and/or C-terminus of a desired heavy or light chain of an amino acid. Derivatives of cysteine (Cys) include, but are not limited to beta-2-Cys, beta-3-Cys, homocysteine, and N-methyl cysteine.

Aspects and Embodiments

Provided herein are multi-drug antibody drug conjugates (MD-ADCs, as described below), as well as Drug Linking Assembly Units (DLA) (having attachment to multiple Drug Units in which there are two different Drug Units ($D^1$ and $D^2$)), and orthogonally Protected Linking Assembly Units (PLA) or scaffolds both having functional groups for attachment to an antibody and to $D^1$ and $D^2$. Each of the MD-ADCs, the DLA Units or the PLA Units will optionally have a Partitioning Agent (Y) attached at a site or component of the DLA or PLA Unit or portion of the MD-ADC.

Multi-Drug Antibody Drug Conjugates

In one aspect, provided herein are multi-drug antibody drug conjugates (MD-ADCs) in which two different Drug Units are covalently attached to antibodies for simultaneous targeted delivery of two different drugs in a therapeutic protocol. For each antibody, the two drugs are attached in an integer ratio, and in some aspects are in a 1:1 ratio, a 2:1 ratio or a 3:1 ratio on each Linking Assembly Unit. Typically, an antibody of an MD-ADC has from 1 to 8 Linking Assembly Units attached thereto which in some aspects is connected to two different Drug Units for a total of 2 to 32 Drug Units ($D^1+D^2$) per antibody, more typically 2 to 10 for a total of 2 to 20 Drug Units.

In some embodiments, a total drug loading of 16 ($D^1$ to $D^2$ Drug Unit in 1:1 ratio) is achieved by completely reducing the antibody so that each of the four inter-chain disulfide linkages is cleaved to produce eight thiols used for attachment of Linking Assembly Units or orthogonally protected Linking Assembly Units. The Linking Assembly Units and orthogonally protected Linking Assembly Units are further designed to have optional attachment sites that connect to Partitioning Agents (e.g., PEG groups). The Partitioning Agents are attachable to a variety of sites on the Linking Assembly Unit or orthogonally protected Linking Assembly Units as will be discussed more completely below.

In some embodiments, the Linking Assembly Units are attached to an antibody at one or more engineered cysteine (eCys) residues. An eCys residue is a cysteine amino acid or a derivative thereof that is incorporated into the heavy chain or light chain of an antibody. It is understood that one or more eCys residues can be incorporated into a single antibody. Typically, Antibodies comprising eCys residues are prepared by mutagenizing a nucleic acid sequence of a parent antibody to encode for one or more amino acid residues with a cysteine. A person of skill in the art can determine suitable positions for incorporation of the eCys residues, and further information can be found in U.S. Pat. No. 9,000,130, the contents of which is incorporated herein for all purposes.

For ease of assembly, the Drug Linking Assembly Units (i.e. Linking Assembly Units with attached Drug Units) are typically constructed prior to attachment to an antibody—and are discussed below in the context of an assembled Linking Assembly Unit with attached Drug Units. One of skill in the art will appreciate that the order of construction, however, can be varied. For example, Linking Assembly Units with Protecting Groups may be attached to antibodies, where the Protecting Groups are removed and Drug Units are added after addition to the antibody.

Linking Assembly Units

A Linking Assembly (LA) Unit is characterized by the following features: (1) an antibody Tethering Group which facilitates attachment of LA to the antibody thiols; (2) Attachment Groups ($Q^1$ and $Q^2$) that in a deprotected form allow for covalent attachment of the Drug Units ($D^1$ and $D^2$); (3) an Attachment Group Linker which provides a connection between two Attachment Groups (X); and optional groups, including Drug Linking Groups ($L^1$ and $L^2$) and Partitioning Agent (Y). A Drug Linking Assembly (DLA) Unit has Drug Units attached.

In certain embodiments, the DLA Unit is characterized by the structure of Formula (Ia):

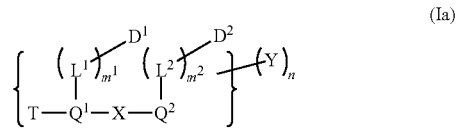

(Ia)

wherein

T is a Tethering Group that provides covalent attachment of LA to antibody thiols produced by reduction of an antibody's interchain disulfide linkages;

$Q^1$ is a first Attachment Group that provides covalent attachment to a first Drug Unit ($D^1$);

$Q^2$ is a second Attachment Group that provides covalent attachment to a second Drug Unit ($D^2$);

each X is an Attachment Group Linker that provides a connection, or spacing between two Attachment Groups;

$D^1$ is a first Drug Unit;

$D^2$ is a second Drug Unit;

$L^1$ is an Optional Linking Group joining $D^1$ to $Q^1$;

$L^2$ is an Optional Linking Group joining $D^2$ to $Q^2$;

subscripts $m^1$ and $m^2$ are each independently 0 or 1;

Y is a Partitioning Agent; and subscript n is 0 or 1.

In another group of embodiments, the DLA Unit is characterized by the structure of Formula (IIa):

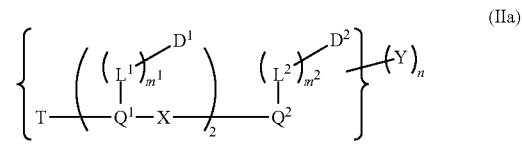

(IIa)

wherein

T is a Tethering Group provides covalent attachment of LA to antibody thiols produced by reduction of an antibody's interchain disulfide linkages;

each $Q^1$ is a first Attachment Group that provides covalent attachment of a first Drug Unit ($D^1$);

$Q^2$ is a second Attachment Group that provides covalent attachment of a second Drug Unit ($D^2$);

X is an Attachment Group Linker;

$D^1$ is a first Drug Unit;

$D^2$ is a second Drug Unit;

$L^1$ is an Optional Linking Group joining $D^1$ to $Q^1$;

$L^2$ is an Optional Linking Group joining $D^2$ to $Q^2$;

subscripts $m^1$ and $m^2$ are each independently 0 or 1;

Y is a Partitioning Agent; and subscript n is 0 or 1.

In yet another group of embodiments, the DLA Unit is characterized by the structure of Formula (IIIa):

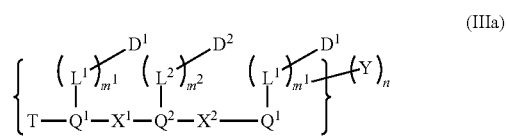

(IIIa)

wherein

T is a Tethering Group that provides covalent attachment of LA to antibody thiols produced by reduction of an antibody's interchain disulfide linkages;

each $Q^1$ is an independently selected first Attachment Group that provides covalent attachment of an independently selected first Drug Unit ($D^1$);

$Q^2$ is a second Attachment Group that provides covalent attachment of a second Drug Unit ($D^2$);

$X^1$ and $X^2$ are each an Attachment Group Linker;

$D^1$ is a first Drug Unit;

$D^2$ is a second Drug Unit;

$L^1$ is an Optional Linking Group joining $D^1$ to $Q^1$;
$L^2$ is an Optional Linking Group joining $D^2$ to $Q^2$;
subscripts $m^1$ and $m^2$ are each independently 0 or 1;
Y is a Partitioning Agent; and
subscript n is 0 or 1.

In still another group of embodiments, the DLA Unit is characterized by the structure of the Formula (IVa)

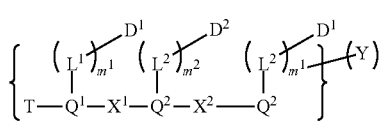

(IVa)

wherein
T is a Tethering Group that provides covalent attachment of LA to antibody thiols produced by reduction of an antibody's interchain disulfide linkages;
each $Q^1$ is an independently selected first Attachment Group that provides covalent attachment of an independently selected first Drug Unit ($D^1$);
$Q^2$ is a second Attachment Group that provides covalent attachment of a second Drug Unit ($D^2$);
$X^1$ and $X^2$ are each an independently selected Attachment Group Linker;
$D^1$ is a first Drug Unit;
$D^2$ is a second Drug Unit;
$L^1$ is an Optional Linking Group joining $D^1$ to $Q^1$;
$L^2$ is an Optional Linking Group joining $D^2$ to $Q^2$;
subscripts $m^1$ and $m^2$ are each independently 0 or 1;
Y is a Partitioning Agent; and
subscript n is 0 or 1.

Tethering Group (T)

A Tethering Group (T) refers to the portion of a Linking Assembly Unit that provides covalent and uniform attachment to antibody thiols. The structural requirements of (T) for the purpose include a functional group that provides covalent attachment to an antibody thiol, and a functional group that provides covalent attachment to a first Attachment Group (Q'). The Tethering Group (T), will in some embodiments have a site providing covalent attachment to a Partitioning Agent (Y).

A number of functional groups suitable as Tethering Groups have been described in the literature and include those functional groups designed for attachment to a thiol moiety present in an antibody. Those functional groups include maleimido moieties (e.g., maleimidocaproyl and self-stabilizing moieties such as mDPR, see WO 2013/173337).

Examples of Tethering Groups, prior to covalent attachment to an antibody thiol, within the scope of the present disclosure include, groups of Formulas (V) and (VI)

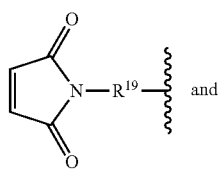

(V)

and

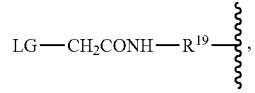

(VI)

wherein, LG is a leaving group, the wavy line to the right is an Attachment Group ($Q^1$ and $Q^2$), and $R^{19}$ is as defined below. One of skill in the art will recognize that the maleimide of Formula (V) is capable of reacting with a thiol of an antibody, and with reference to Formula VI, the thiol of an antibody will covalently attach to the carbon bearing LG via nucleophilic attack to displace the leaving group (LG). Suitable leaving groups are well known to one of skill in the art and include halogen, tosylate, and mesylate.

In some embodiments, $R^{19}$ is $C_1$-$C_{10}$ alkylene-, $C_1$-$C_{10}$ heteroalkylene-, $C_3$-$C_8$ carbocyclo-, —O—($C_1$-$C_8$ alkyl)-, -arylene-, $C_1$-$C_{10}$ alkylene-arylene-, -arylene-$C_1$-$C_{10}$ alkylene-, $C_1$-$C_{10}$ alkylene-($C_3$-$C_8$ carbocyclo)-, (C3-$C_8$ carbocyclo)-$C_1$-$C_{10}$alkylene-,$C_3$-$C_8$ heterocyclo-, $C_1$-$C_{10}$ alkylene-($C_3$-$C_8$, heterocyclo), ($C_3$-$C_8$ heterocyclo)-$C_1$-$C_{10}$ alkylene-, $C_1$-$C_{10}$ alkylene-C(=O)—, $C_1$-$C_{10}$ heteroalkylene-C(=O)—, $C_3$-$C_8$ carbocyclo-C(=O)—, —O—($C_1$-$C_8$ alkyl)-C(=O)—, -arylene-C(=O), $C_1$-$C_{10}$ alkylene-arylene-C(=O)—, -arylene-$C_1$-$C_{10}$ alkylene-C(=O)—, $C_1$-$C_8$ alkylene-($C_3$-$C_8$, carbocyclo)-C(=O)—, ($C_3$-$C_8$ carbocyclo)-$C_1$-$C_{10}$ alkylene-C(=O)—, $C_3$-$C_8$ heterocyclo-C (=O)—, $C_1$-$C_{10}$ alkylene-($C_3$-$C_8$ heterocyclo)-C(=O)—, ($C_3$-$C_8$ heterocyclo)-$C_1$-$C_{10}$ alkylene-C(=O)—, $C_1$-$C_{10}$ alkylene-NH—, $C_1$-$C_{10}$ heteroalkylene-NH—, $C_3$-$C_8$ carbocyclo-NH—, —O—($C_1$-$C_8$ alkyl)-NH—, -arylene-NH, $C_1$-$C_{10}$ alkylene-arylene-NH, -arylene-$C_1$-$C_{10}$ alkylene-NH—, $C_1$-$C_{10}$ alkylene-($C_3$-$C_8$ carbocyclo)-NH—, ($C_3$-$C_8$ carbocyclo)-$C_1$-$C_{10}$ alkylene-NH—, $C_3$-$C_8$ heterocyclo-NH—, $C_1$-$C_{10}$ alkylene-($C_3$-$C_8$ heterocyclo)-NH—, ($C_3$-$C_8$ heterocyclo)-$C_1$-$C_{10}$ alkylene-NH—, $C_1$-$C_{10}$ alkylene-S—, $C_1$-$C_{10}$ heteroalkylene-S—, $C_3$-$C_8$ carbocyclo-S—, —O—($C_1$-$C_8$ alkyl)-S—, -arylene-S—, $C_1$-$C_{10}$ alkylene-arylene-S—, -arylene-$C_1$-$C_{10}$ alkylene-S—, $C_1$-$C_{10}$ alkylene-($C_3$-$C_8$ carbocyclo)-S—, ($C_3$-$C_8$ carbocyclo)-$C_1$-$C_8$ alkylene-S—, $C_3$-$C_8$ heterocyclo-S—, $C_1$-$C_{10}$ alkylene-($C_3$-$C_8$ heterocyclo)-S—, or ($C_3$-$C_8$ heterocyclo)-$C_1$-$C_{10}$ alkylene-S—. Any of the $R^{19}$ substituents can be substituted or non-substituted. In some embodiments, the $R^{19}$ substituents are unsubstituted.

In some embodiments, a Tethering Group, prior to covalent attachment to an antibody thiol, has formula (VII)

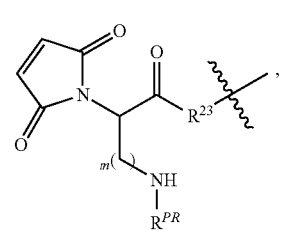

(VII)

wherein $R^{PR}$ is hydrogen or a protecting group, subscript m is 1 or 2, and $R^{23}$ is —NH—$C_{1-5}$alkylene-C(=O)—, or a mono, di-, tri-, tetra-, or penta-peptide. In some embodiments, $R^{23}$ is —NH—$CH_2$—C(=O)—. In some embodiments, $R^{23}$ is a di-, or tri-peptide. In some embodiments, the amino acids in the peptide unit of $R^{23}$ are independently selected from valine, alanine, glycine, leucine, and citrulline.

It is also understood that the substituted maleimide shown in Formula (V) and Formula (VII) will in some embodiments exist in hydrolyzed form(s) after attachment to an antibody thiol. That is, in exemplary embodiments, the resulting substituted succinimide is in hydrolyzed form(s) as shown below:

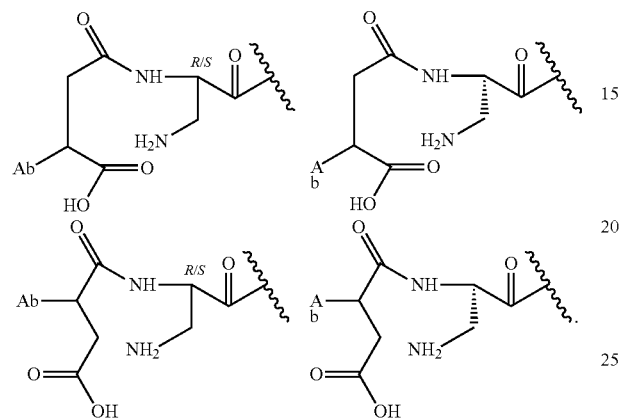

In some aspects, the $R^{19}$ substituents of Formulas (V) and (VI) are optionally substituted. In some of those embodiments, the $R^{19}$ substituent of formula (V), is substituted by a Basic Unit, e.g. $(CH_2)_xNH_2$, $(CH_2)_xNHR^a$, and $(CH_2)_xNR^a_2$, wherein subscript x is an integer ranging from 1-4 and each $R^a$ is an independently selected $C_1$-$C_6$ alkyl, or two $R^a$ groups are combined with the nitrogen to which they are attached to form an azetidinyl, pyrrolidinyl or piperidinyl group.

In some embodiments, the Tethering Group (T), prior to covalent attachment to an antibody thiol, is selected from the group consisting of

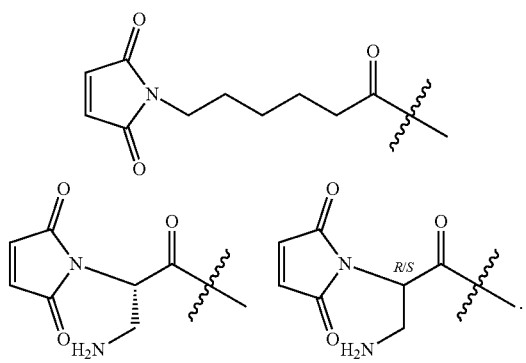

In some selected embodiments, the Tethering Group (T), prior to attachment to an antibody thiol, is, for example, a maleimido-containing linker moiety that is cleavable by a protease. Accordingly, exemplary T Units cleavable by a protease for use with the MD-ADCs described herein include the following structures wherein, S is the sulfur atom of an antibody thiol, the wavy line to the right is an Attachment Group Linker, and the wavy line to the left is the antibody:

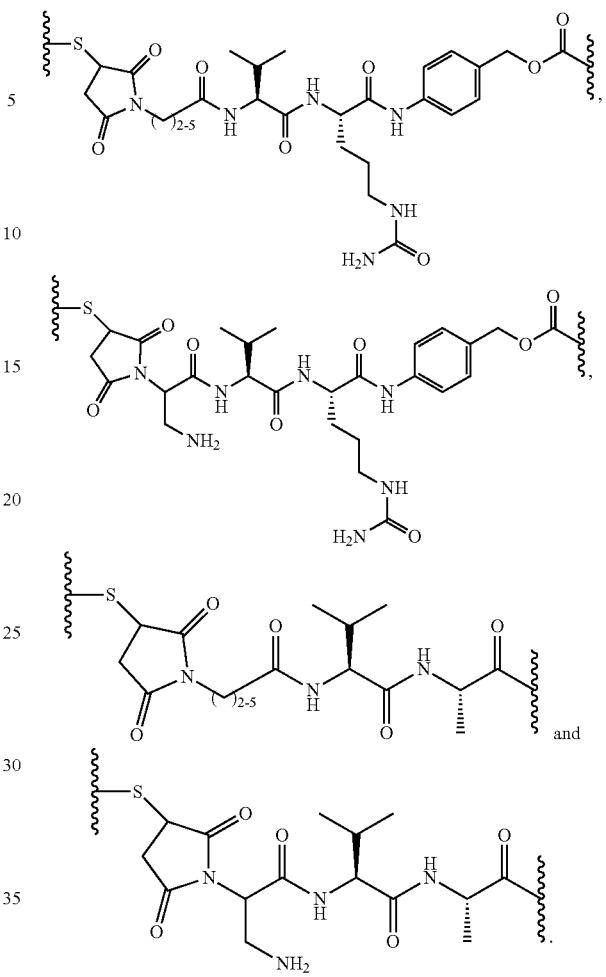

Attachment Groups ($Q^1$ and $Q^2$)

Attachment Groups useful in the LA Units described herein are those groups having functional groups that can be protected 'orthogonally'—protected to allow for selective de-protection when the attachment of a Drug Unit ($D^1$ or $D^2$) is being carried out. Protecting Groups ($P^1$ and $P^2$) of the present disclosure are discussed in greater detail in a later section.

In one group of embodiments, the Attachment Groups are natural or non-natural amino acids comprising a reactive functional group for attachment of a Protecting Group, a Drug Unit, or an Optional Linking Group. Those include amino acids with functional groups such as thiol, amine, hydroxyl, carboxylic acid, or amide such as, cysteine, serine, threonine, tyrosine, lysine, citrulline, arginine, aspartate, glutamate, asparagine, and glutamine. Those functional groups are capable of reacting with a suitable corresponding group on the Protecting Group, Drug Unit, or Optional Linking Group.

In some embodiments the Attachment Groups ($Q^1$ and $Q^2$) are independently selected from amino acids such as cysteine, serine, threonine, lysine, citrulline, and arginine. In some embodiments the Attachment Groups ($Q^1$ and $Q^2$) are independently selected from the group consisting of cysteine, serine, and lysine. In some embodiments, the Attachment Groups ($Q^1$ and $Q^2$) are cysteine.

In some embodiments the Attachment Groups ($Q^1$ and $Q^2$) are independently selected from cysteine (Cys) derivatives such as Cys (StBu), H-Cys(Acm)-OH, H-Cys(Trt)-OH, H-Cys(StBu)-OH, H-Cys(Bzl)-OH, H-Cys(S-Et)-OH, H-Cys($SO_3$H)—OH, H-Cys(aminoethyl)-OH, H-Cys(carbamoyl)-OH, H-Cys(S-phenyl)-OH, H-Cys(Boc)-OH, and H-Cys(hydroxyethyl)-OH.

In some embodiments the Attachment Groups ($Q^1$ and $Q^2$) are independently selected from cysteine (Cys) derivatives such as Cys(Stmp), Cys(Mmt), Thiaproline, Cys(Dpm), Cys(Thp), Cys(4-MeOBzl), Cys(Npys), Cys(Cys).

In some embodiments the Attachment Groups ($Q^1$ and $Q^2$) are independently selected from cysteine (Cys) derivatives such as beta-2-Cys, beta-3-Cys, homocysteine, and N-methyl cysteine.

In accordance with the Attachment Groups, Protecting Groups, Drug Units, or Optional Linking Groups described herein, suitable covalent attachments between the Attachment Group and adjacent groups or linkages include disulfides, thioethers, peptides, hydrazine, ester, or carbamate bonds.

It is understood that Attachment Groups do not have to include an amino acid residue. So long as the Attachment Group comprises a functional group that is capable of being protected/deprotected 'orthogonally' and are further comprised of chemical groups that are capable of covalent attachment to the Attachment Group Linker and/or the optional Linking unit, said Attachment Group are also suitable components of a Linking Assembly Unit.

Attachment Group Linkers (X, $X^1$, $X^2$, and $X^B$)

To provide suitable spacing between Attachment Groups, Linking Assembly Units provided herein include, in some embodiments, Attachment Group Linkers (X, $X^1$ and $X^2$). Those Attachment Group Linkers are typically groups that, in addition to providing spacing between the Attachment Groups ($Q^1$ and $Q^2$), will result in benign components when the MC-ADC composition is metabolized in vivo. Typical Attachment Group Linkers are, for example, glycine, alanine, β-alanine, and di-peptide or tri-peptides. While a variety of amino acids are useful in this context, preferred amino acids are those having side chains that do not require protection/de-protection steps during construction of the LA. For example, suitable amino acids that do not require protection/de-protecting steps during construction of the LA include glycine, alanine, β-alanine, valine, leucine, phenylalanine, and proline. In embodiments where the Attachment Group Linker is an amino acid, the amino position on each amino acid may be substituted or unsubstituted.

In some embodiments, an Attachments Group Linker (X, $X^1$, or $X^2$) is a di-peptide wherein each peptide is independently selected from the group consisting glycine, alanine, β-alanine, valine, leucine, phenylalanine, and proline.

In some embodiments, an Attachments Group Linker (X, $X^1$, or $X^2$) is a tri-peptide wherein each peptide is independently selected from the group consisting glycine, alanine, β-alanine, valine, leucine, phenylalanine, and proline.

In some embodiments, an Attachment Group Linker is branched. That is Attachment Groups ($Q^1$ and $Q^2$) are attached to a single Attachment Group Linker ($X^B$). In such embodiments, the branched Attachment Group Linker ($X^B$) is directly attached to Tethering Group (T). Typical branched Attachment Group Linkers are, for example, amino acids that include an additional functional group in their side chain that provide an easy means for covalently attaching the branched Attachment Group Linker and the Tethering Group. Suitable amino acids include, but are not limited to, lysine, aspartic acid, glutamic acid, serine, threonine, asparagine, and glutamine. In some embodiments, the branched Attachment Group Linker is lysine. Although, covalently attaching the branched Attachment Group Linker ($X^B$) to the Tethering Group via the side chain of the amino acid is a suitable means of attachment, a person of skill in the art will recognize that each functional group in the trifunctional amino acids listed above can be used for covalently attaching Attachment Groups, $Q^1$ and $Q^2$, as well as Tethering Group (T) to the branched Attachment Group Linker ($X^B$).

In some embodiments, the amino position on each amino acid is independently substituted with a methyl group.

It is understood that given the role of the Attachment Group Linkers, an amino acid unit is not required. So long as the Attachment Group Linker comprises chemical groups for covalent attachment to the two or more Attachment Groups ($Q^1$ and $Q^2$) in the Linker Assembly Unit, said group is a suitable component in a Linking Assembly Unit.

Optional Linking Groups ($L^1$ and $L^2$)

Still other components of the Linking Assembly Units are Optional Linking Groups ($L^1$ and $L^2$), which may be included for reasons such as facilitating attachment of the Drug Units to the LA Unit, or for introducing a cleavable linking group. In some embodiments, the Drug Linking Assembly (DLA) Units of the present disclosure include an Optional Linking Group between the Drug Unit and the Attachment Group ($Q^1$ or $Q^2$). A person of skill in the art will realize that "optional" indicates the linker can be replaced by a direct bond between, for example, the Drug Unit and the Attachment Group Linker.

A number of linkers are known in the art for attachment of Drug Units to functional groups present in antibodies or sites on linkers—and are useful herein for attaching Drug Units to the Attachment Groups of the Linking Assembly Unit.

In some embodiments, Optional Linking Groups include a terminal maleimide, allowing for reliable linkage between the attachment unit $Q^1$ or $Q^2$. It is understood that the terminal maleimide functional groups are most useful for covalent attachment to $Q^1$ or $Q^2$ moieties that include a nucleophilic group such as hydroxyl, thiol, or amine and in particular an antibody thiol. As described in the Tethering Group section, an attached succinimide, obtained from a maleimide-containing Tethering Group, exists in some embodiments, in hydrolyzed form(s), or when a basic group such as an amine is located proximal to a substituted succinimide, the succinimide is capable of reacting to form a self-stabilizing assembly (as described in further detail in WO 2013/173337).

In some embodiments, an Optional Linking Groups include a para-aminobenzyloxy-carbonyl (PABC) group that is covalently attached to a Drug Unit ($D^1$ or $D^2$). In some of those embodiments, the PABC group is substituted with a sugar such as glucose, or a derivative thereof to form a Glucuronide Unit (as described in further detail in WO 2007/011968).

In some embodiments, an Optional Linking Group has Formula (VIII) or (IX):

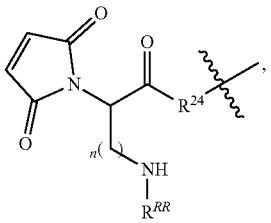

(VIII)

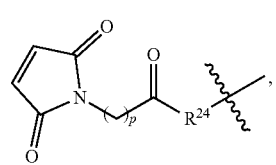

(IX)

wherein $R^{RR}$ is hydrogen or a protecting group, n is 1 or 2, p is an integer from 1-5, and $R^{24}$ is —NH—$C_{1-5}$alkylene-C(=O)—, —NH—$C_{1-5}$alkylene-C(=O)—NH—phenylene-$CH_2$—O—C(=O)—, -(di-peptide)-NH-phenylene-$CH_2$—O—C(=O)—, or a mono, di-, tri-, tetra-, or penta-peptide. The phenylene in the previous mentioned groups may be optionally substituted with a sugar such as glucose, or a derivative thereof. The amine groups of $R^{24}$ optionally include a methyl ($CH_3$) instead of an H. In some embodiments, $R^{24}$ is a di-, or tri-peptide. In some embodiments, $R^{24}$ is —NH—$CH_2$—C(=O)—. In some embodiments, the amino acids of the peptide unit in $R^{24}$ are independently selected from valine, alanine, glycine, leucine, and citrulline. It is understood that the Formulae above are shown before linkage to Attachment Groups (X). The "wavy line" indicates the point of attachment to the Drug Unit. Depending on the Drug Unit and the linking chemistry employed between the Drug Unit and the Optional Linking Group, the terminal moiety in the above listed $R^{24}$ groups also in some aspects include a nucleophilic groups such as an amine or a hydroxyl attached to the terminal carbonyl.

In some embodiments, an Optional Linking Group has Formula (XI) or (XII):

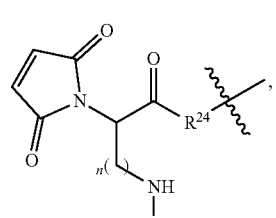

(XI)

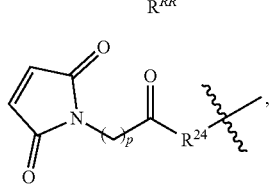

(XII)

wherein $R^{RR}$ is hydrogen or a protecting group, subscript n is 1 or 2, subscript p is an integer from 1-5, and $R^{24}$ is —NH—$C_{1-5}$alkylene-C(=O)—NH—phenylene-$CH_2$—O—C(=O)-heterocyclyl-$C_{1-4}$alkylene-$b^1$-heterocyclyl-$b^2$-; -(di-peptide)-NH-phenylene-$CH_2$—O—C(=O)-heterocyclyl-$C_{1-4}$alkylene-$b^1$-heterocyclyl-$b^2$-; wherein $b^1$ and $b^2$ are independently a bond or heteroatoms selected from NH or O, wherein the each heterocyclyl group is a 5 or 6 membered ring having 1-3 heteroatom ring members selected from N, O, and S; and wherein each heterocyclyl group is optionally substituted with from 1 to 3 groups selected from $C_{1-4}$ alkyl, hydroxyl, alkoxy, carboxyl, and —C(=O)—$C_{1-4}$alkyl. In some embodiments, $b^1$ and $b^2$ are each heteroatoms selected from NH or O. The amine groups of $R^{24}$ may also include a methyl ($CH_3$) instead of an H. In some embodiments, $R^{24}$ is a di-, or tri-peptide. In some embodiments, $R^{24}$ is —NH—$CH_2$—C(=O)—. In some embodiments, the amino acids of the peptide unit in $R^{24}$ are independently selected from valine, alanine, glycine, leucine, and citrulline. It is understood that the Formulae above are shown before covalent attachment to Attachment Groups (X). The "wavy line" indicates the point of attachment to Drug Unit $D^1$ or $D^2$.

In some embodiments, Optional Linking Groups are Releaseable Linking Group, $L^{R1}$ or $L^{R2}$. In some other aspects, the Optional Linking Group does not include a Releaseable Linking Group. In embodiments without a Releaseable Linking Group, release of Drug Unit is via a total protein degradation pathway (i.e., non-cleavable pathway).

For those embodiments in which the Optional Linking Group is a Releasable Linking Group ($L^{R1}$ or $L^{R2}$) that group allows efficient release of free drug at the target cell, sufficient to induce, e.g., cytotoxicity or cytostaticity. Preferably, the Releaseable Linking Group is designed for efficient release of the free drug once the conjugate has been internalized into the target cell, but may also be designed to release free drug within the vicinity of targeted cells. Suitable recognition sites for cleavage are those that allow efficient release of an MD-ADC's Drug Unit(s). Preferably, the recognition site is a peptide cleavage site (such as in a peptide-based releasable linker assembly), a sugar cleavage site (such as in sugar-based releasable linker assembly, which is or is comprised of a Glucuronide Unit), or a disulfide cleavage site (such as in disulfide-based releasable linker assembly). Examples of peptide cleavage sites include those recognized by intracellular proteases, such as those present is lysosomes. Examples of sugar cleavage site include those recognized by glycosidases, including glucuronidases, such as beta-glucuronidase.

In some embodiments, the Releaseable Linking Group ($L^{R1}$ or $L^{R2}$) is a di-peptide. In some embodiments, the di-peptide is -Val-Cit-, -Phe-Lys- or -Val-Ala-.

In some embodiments $L^1$ and $L^2$ are independently selected from the group consisting of maleimido-caproyl (mc), maleimido-caproyl-valine-citrulline (mc-vc), maleimido-caproyl-valine-citrulline-paraaminobenzyloxycarbonyl (mc-vc-PABC) and MDPr-vc. It is understood that $L^1$ and $L^2$ in some embodiments is further substituted with a basic moiety such as an amine to form a self-stabilizing succinimide linker discussed above and in greater detail in (WO 2013/173337).

General methods of covalent attachment of a Drug Unit to an Optional Linking Group ($L^1$ or $L^2$) are known in the art and linkers known in the art or traditional ADCs may be used with the MD-ADCs of the present disclosure. For example, auristatin and maytansine ADCs are currently in clinical development for the treatment of cancer. Monomethyl auristatin E is conjugated through a protease cleavable peptide linker to an antibody, monomethyl auristatin F is conjugated directly to an antibody through maleimidocaproic acid, DM1 is conjugated through a disulfide or directly through the heterobifunctional SMCC linker, and DM4 is conjugated through a disulfide linker. Those linker systems can be used with the MD-ADCs described herein and provide release of drug by an enzymatically cleavable or non-enzymatically cleavable system depending on the linker system used. Disulfide, thioether, peptide, hydrazine, ester, or carbamate bonds are all examples of bonds that are also useful for connecting Drug Unit $D^1$ or $D^2$ to a first or second Optional Linking Group ($L^1$ or $L^2$).

Optional partitioning agents (Y) can be linked via any suitable atom of the Optional Linking Groups. Methods of making such linkages are known in the art.

Optional Partitioning Agents (Y)

The MD-ADCs described herein can also include attached Partitioning Agents (Y). The Partitioning Agents are useful, for example, to mask the hydrophobicity of particular Drug Units or Linking Assembly Units. Accordingly, a number of Partitioning Agents will act to increase the hydrophilic character of the MD-ADC to which they are attached.

Representative Partitioning Agents include polyethylene glycol (PEG) units, cyclodextrin units, polyamides, hydrophilic peptides, polysaccharides and dendrimers.

When the optional Partitioning Agent is included in one or more of groups T, $L^1$, $L^2$, X, $X^1$ or $X^2$, $Q^1$ or $Q^2$, the Partitioning Agent in some embodiments includes a lysine residue which allows for covalent attachment of the Partitioning Agent to the Linking Assembly Unit.

Polyethylene Glycol Unit (PEG)

Polydisperse PEGS, monodisperse PEGS and discrete PEGs can be used to make the Compounds of the present invention. Polydisperse PEGs are a heterogeneous mixture of sizes and molecular weights whereas monodisperse PEGs are typically purified from heterogeneous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length.

The PEG Unit provided herein comprises one or multiple polyethylene glycol chains. The polyethylene glycol chains can be linked together, for example, in a linear, branched or star shaped configuration. Typically, at least one of the PEG chains is derivatized at one end for covalent attachment to an appropriate site on a component of the Linking Assembly Unit (e.g. $Q^1$, $Q^2$, X, $X^1$ or $X^2$, or to optional Linking Groups ($L^1$ or $L^2$)). Exemplary attachments to the Linking Assembly Unit are by means of non-conditionally cleavable linkages or via conditionally cleavable linkages. Exemplary attachments are via amide linkage, ether linkages, ester linkages, hydrazone linkages, oxime linkages, disulfide linkages, peptide linkages or triazole linkages. In some aspects, attachment to the Linking Assembly Unit is by means of a non-conditionally cleavable linkage. In some embodiments, attachment to the Linking Assembly Unit is not via an ester linkage, hydrazone linkage, oxime linkage, or disulfide linkage. In some embodiments, attachment to the Linking Assembly Unit is not via a hydrazone linkage.

A conditionally cleavable linkage refers to a linkage that is not substantially sensitive to cleavage while circulating in the plasma but is sensitive to cleavage in an intracellular or intratumoral environment. A non-conditionally cleavable linkage is one that is not substantially sensitive to cleavage in any biological environment. Chemical hydrolysis of a hydrazone, reduction of a disulfide, and enzymatic cleavage of a peptide bond or glycosidic linkage are examples of conditionally cleavable linkages.

The PEG Unit will be directly attached to the MD-ADC (or Intermediate thereof) at the Linking Assembly Unit. The other terminus (or termini) of the PEG Unit will be free and untethered and may take the form of a methoxy, carboxylic acid, alcohol or other suitable functional group. The methoxy, carboxylic acid, alcohol or other suitable functional group acts as a cap for the terminal PEG subunit of the PEG Unit. By untethered, it is meant that the PEG Unit will not be attached at that untethered site to a Drug Unit, to an antibody, or to a linking component linking a Drug Unit and/or an antibody. For those embodiments wherein the PEG Unit comprises more than one PEG chain, the multiple PEG chains may be the same or different chemical moieties (e.g., PEGs of different molecular weight or number of subunits). The multiple PEG chains are attached to the Linking Assembly Unit at a single attachment site. The skilled artisan will understand that the PEG Unit in addition to comprising repeating polyethylene glycol subunits may also contain non-PEG material (e.g., to facilitate coupling of multiple PEG chains to each other or to facilitate coupling to the Linking Assembly Unit). Non-PEG material refers to the atoms in the PEG Unit that are not part of the repeating —$CH_2CH_2O$-subunits. In some embodiments provided herein, the PEG Unit comprises two monomeric PEG chains attached to each other via non-PEG elements. In other embodiments provided herein, the PEG Unit comprises two linear PEG chains attached to a central core that is attached to the Linking Assembly Unit (i.e., the PEG Unit itself is branched).

There are a number of PEG attachment methods available to those skilled in the art, [see, e.g., Goodson, et al. (1990) *Bio/Technology* 8:343 (PEGylation of interleukin-2 at its glycosylation site after site-directed mutagenesis); EP 0 401 384 (coupling PEG to G-CSF); Malik, et al., (1992) *Exp. Hematol.* 20:1028-1035 (PEGylation of GM-CSF using tresyl chloride); ACT Pub. No. WO 90/12874 (PEGylation of erythropoietin containing a recombinantly introduced cysteine residue using a cysteine-specific mPEG derivative); U.S. Pat. No. 5,757,078 (PEGylation of EPO peptides); U.S. Pat. No. 5,672,662 (Poly(ethylene glycol) and related polymers monosubstituted with propionic or butanoic acids and functional derivatives thereof for biotechnical applications); U.S. Pat. No. 6,077,939 (PEGylation of an N-terminal .alpha.-carbon of a peptide); Veronese et al., (1985) *Appl. Biochem. Bioechnol* 11:141-142 (PEGylation of an N-terminal α-carbon of a peptide with PEG-nitrophenylcarbonate ("PEG-NPC") or PEG-trichlorophenylcarbonate); and Veronese (2001) *Biomaterials* 22:405-417 (Review article on peptide and protein PEGylation)].

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) are also useful as a reactive group for attaching PEG. In addition, enzyme-assisted methods for introducing activated groups (e.g., hydrazide, aldehyde, and aromatic-amino groups) specifically at the C-terminus of a polypeptide have been described (see Schwarz, et al. (1990) *Meth-* ods *Enzymol.* 184:160; Rose, et al. (1991) *Bioconjugate Chem.* 2:154; and Gaertner, et al. (1994) *J. Biol. Chem.* 269:7224].

In some embodiments, PEG molecules are attached to amino groups using methoxylated PEG ("mPEG") having different reactive moieties. Non-limiting examples of such reactive moieties include succinimidyl succinate (SS), succinimidyl carbonate (SC), mPEG-imidate, para-nitrophenylcarbonate (NPC), succinimidyl propionate (SPA), and cyanuric chloride. Non-limiting examples of such mPEGs include mPEG-succinimidyl succinate (mPEG-SS), mPEG$_2$-succinimidyl succinate (mPEG$_2$-SS); mPEG-succinimidyl carbonate (mPEG-SC), mPEG$_2$-succinimidyl carbonate (mPEG$_2$-SC); mPEG-imidate, mPEG-para-nitrophenylcarbonate (mPEG-NPC), mPEG-imidate; mPEG$_2$-para-nitrophenylcarbonate (mPEG$_2$-NPC); mPEG-succinimidyl propionate (mPEG-SPA); mPEG$_2$-succinimidyl propionate (mPEG, -SPA); mPEG-N-hydroxy-succinimide (mPEG-NHS); mPEG$_2$-N-hydroxy-succinimide (mPEG$_2$-NHS); mPEG-cyanuric chloride; mPEG$_2$-cyanuric chloride; mPEG$_2$-Lysinol-NPC, and mPEG$_2$-Lys-NHS.

Generally, at least one of the PEG chains that make up the PEG Unit is functionalized so that it is capable of covalent attachment to the Linking Assembly Unit. Functionalization includes, for example, via an amine, thiol, NHS ester, maleimide, alkyne, azide, carbonyl, or other functional group. In some embodiments, the PEG Unit further comprises non-PEG material (i.e., material not comprised of —CH$_2$CH$_2$O—) that provides coupling to its Linking Assembly Unit or coupling of two or more PEG chains.

A wide variety of polyethylene glycol (PEG) species can be used, and substantially any suitable reactive PEG reagent can be used. In some embodiments, the reactive PEG reagent will result in formation of a carbamate or amide bond upon attachment to the Linking Assembly Unit (e.g. Q$^1$, Q$^2$, X, X$^1$ or X$^2$, or to optional Linking Groups (L$^1$ or L$^2$)). The following PEG reagents are useful in various embodiments: mPEG$_2$-NHS, mPEG$_2$-ALD, multi-Arm PEG, mPEG(MAL)$_2$, mPEG$_2$(MAL), mPEG-NH$_2$, mPEG-SPA, mPEG-SBA, mPEG-thioesters, mPEG-Double Esters, mPEG-BTC, mPEG-ButyrALD, mPEG-ACET, heterofunctional PEGs (NH$_2$-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE™ series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs as selected by those skilled in the art for their particular application and usage.

The presence of the PEG Unit in a Drug Linking Assembly Unit is capable of having two potential impacts upon the pharmacokinetics of the resulting MD-ADC. The desired impact is a decrease in clearance (and consequent increase in exposure) that arises from the reduction in non-specific interactions induced by the exposed hydrophobic elements of the Drug Unit. The second impact is undesired and is a decrease in volume and rate of distribution that sometimes arises from the increase in the molecular weight of the MD-ADC. Increasing the number of PEG subunits increases the hydrodynamic radius of a conjugate, typically resulting in decreased diffusivity. In turn, decreased diffusivity typically diminishes the ability of the MD-ADC to penetrate into a tumor (Schmidt and Wittrup, *Mol Cancer Ther* 2009; 8:2861-2871). Because of these two competing pharmacokinetic effects, it is desirable to use a PEG that is sufficiently large to decrease the MD-ADC clearance thus increasing plasma exposure, but not so large as to greatly diminish its diffusivity, to an extent that it interferes with the ability of the MD-ADC to reach the intended target cell population. See the examples (e.g., examples 1, 18, and 21 of US2016/0310612), which is incorporated by reference herein, for methodology for selecting an optimal PEG size for a particular drug-linker.

In one group of embodiments, the PEG Unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. As used herein a subunit of a PEG Unit refers to a polyethylene glycol moiety having the formula

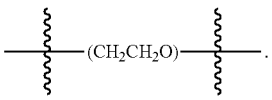

In some such embodiments, the PEG Unit comprises no more than about 72 subunits.

In one group of embodiments, the PEG Unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In preferred embodiments, the PEG Unit comprises a combined total of at least 6 subunits, at least 8, at least 10 subunits, or at least 12 subunits. In some such embodiments, the PEG Unit comprises no more than a combined total of about 72 subunits, preferably no more than a combined total of about 36 subunits.

In another group of embodiments, the PEG Unit comprises a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or from 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In another group of embodiments, the PEG Unit comprises one or more linear PEG chains having a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In another group of embodiments, the PEG Unit is a derivatized linear single PEG chain having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits.

In another group of embodiments, the PEG Unit is a derivatized linear single PEG chain having from 6 to 72, 6 to 60, 6 to 48, 6 to 36 or 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

In another group of embodiments, the PEG Unit is a derivatized linear single PEG chain having from 2 to 72, 2 to 60, 2 to 48, 2 to 36 or 2 to 24 subunits, from 2 to 72, 2 to 60, 2 to 48, 2 to 36 or 2 to 24 subunits, from 3 to 72, 3 to 60, 3 to 48, 3 to 36 or 3 to 24 subunits, from 3 to 72, 3 to 60, 3 to 48, 3 to 36 or 3 to 24 subunits, from 4 to 72, 4 to 60, 4 to 48, 4 to 36 or 4 to 24 subunits, from 5 to 72, 5 to 60, 5 to 48, 5 to 36 or 5 to 24 subunits.

Exemplary linear PEG Units that are useful as a Partitioning Agent in any of the embodiments provided herein are as follows:

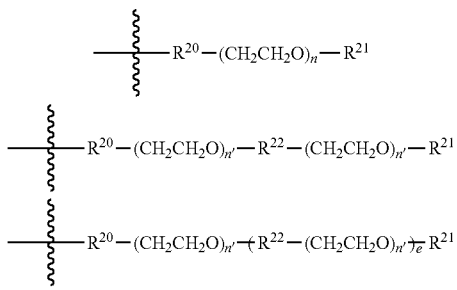

wherein the wavy line indicates site of attachment to the Parallel Connector Unit, $R^{20}$ is a PEG Attachment Unit, $R^{21}$ is a PEG Capping Unit;

$R^{22}$ is an PEG Coupling Unit (i.e., for coupling multiple PEG subunit chains together)

subscript n is independently selected from 2 to 72 (preferably from 4 to 72, more preferably from 6 to 72, from 8 to 72, from 10 to 72, from 12 to 72 or from 6 to 24);

subscript e is 2 to 5 each subscript n' is independently selected from 1 to 72. In preferred embodiments, there are at least 6, preferably at least 8, at least 10, or at least 12 PEG subunits in the PEG Unit. In some embodiments, there are no more than 72 or 36 PEG subunits in the PEG Unit.

In preferred embodiments, subscript n is 8 or about 8, 12 or about 12, 24 or about 24.

The PEG Attachment Unit is part of the PEG Unit and that covalently attaches the PEG Unit to other portions of the Linking Assembly Units. Accordingly, a portion of the Linking Assembly Unit (T, $Q^1$, $L^1$, $D^1$, X, $Q^2$, $L^2$, $D^2$, $X^1$ or $X^2$) has a functional group that provides a bond to the PEG Unit. Functional groups for attachment of the PEG Unit to a site on the Linking Assembly Unit include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, in some embodiments the PEG unit is covalently attached to a site on the Linking Assembly Unit, for example, via disulfide, thioether, hydrazone, oxime, peptide, ester, sulfonamide, carbamate, or amide bonds. In other embodiments, the PEG Attachment Unit is attached by means of Click chemistry (a product of the cycloaddition between azide and alkyne functional groups), addition reaction, addition/elimination or substitution reaction that occurs when attaching the PEG Unit to the Linking Assembly Unit.

The PEG Coupling Unit is part of the PEG Unit and is non-PEG material that acts to connect two or more chains of repeating $CH_2CH_2O$— subunits. In exemplary embodiments, the PEG coupling Unit $R^{22}$ is —$C_{1-10}$alkylene-C(O)—NH—, —$C_{1-10}$ alkylene-NH—C(O)—, —$C_{2-10}$ alkylene-NH—, —$C_{2-10}$ alkylene-O—, —$C_{1-10}$ alkylene-S—, or —$C_{2-10}$alkylene-NH—.

In exemplary embodiments, the PEG Attachment Unit $R^2$ is —C(O)—, —O—, —S—, —S(O)—, —NH—, —C(O)O—, —C(O)$C_{1-10}$alkyl, —C(O)$C_{1-10}$alkyl-O—, —C(O)$C_{1-10}$alkyl-$CO_2$—, —C(O)$C_{1-10}$alkyl-NH—, —C(O)$C_{1-10}$alkyl-S—, —C(O)$C_{1-10}$alkyl-C(O)—NH—, —C(O)$C_{1-10}$alkyl-NH—C(O)—, —$C_{1-10}$alkyl, —$C_{1-10}$alkyl-O—, —$C_{1-10}$alkyl-$CO_2$—, —$C_{1-10}$alkyl-NH—, —$C_{1-10}$alkyl-S—, —$C_{1-10}$alkyl-C(O)—NH—, —$C_{1-10}$alkyl-NH—C(O)—, —$CH_2CH_2SO_2$—$C_{1-10}$alkyl-, —$CH_2C(O)$—$C_{1-10}$alkyl-, =N—(O or N)—$C_{1-10}$alkyl-O—, =N—(O or N)—$C_{1-10}$alkyl-NH—, =N—(O or N)—$C_{1-10}$alkyl-$CO_2$—, =N—(O or N)—$C_{1-10}$alkyl-S—,

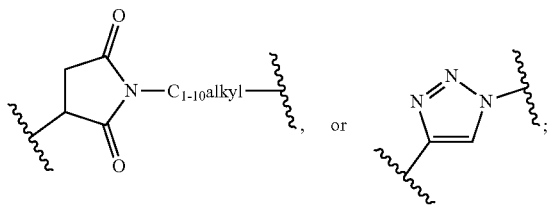

each $R^{21}$ is independently —$C_{1-10}$ alkyl, —$C_{2-10}$ alkyl-$CO_2H$, —$C_{2-10}$ alkyl-OH, —$C_{2-10}$ alkyl-$NH_2$, $C_{2-10}$ alkyl-NH($C_{1-3}$ alkyl), or $C_{2-10}$ alkyl-N($C_{1-3}$ alkyl)$_2$; and each $R^{22}$ is independently —$C_{1-10}$ alkyl-C(O)—NH—, —$C_{1-10}$ alkyl-NH—C(O)—, —$C_{2-10}$ alkyl-NH—, —$C_{2-10}$ alkyl-O—, —$C_{1-10}$ alkyl-S—, or —$C_{2-10}$ alkyl-NH—.

In some embodiments, $R^{20}$ is —NH—, —C(=O)—, triazole-linked groups, or —S—, or maleimido-linked groups such as

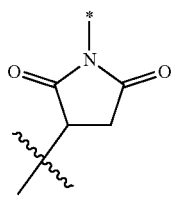

wherein the wavy line indicates the site of attachment to the Linking Assembly Unit and the asterisk indicates the site of attachment with the PEG Unit. In some such aspects, $R^{21}$ is $C_{1-10}$ alkyl, —$C_{2-10}$ alkyl-$CO_2H$, —$C_{2-10}$ alkyl-OH, or —$C_{2-10}$ alkyl-$NH_2$.

Illustrative linear PEG Units that can be used in any of the embodiments provided herein are as follows:

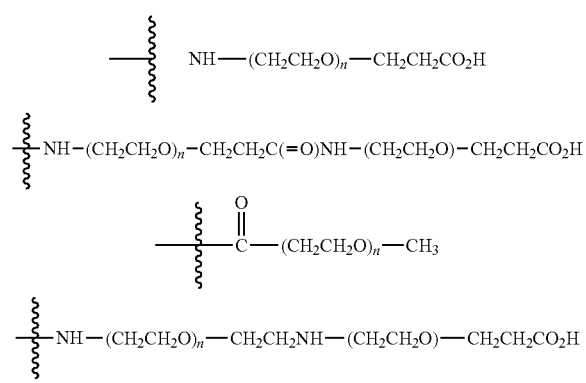

wherein the wavy line indicates site of attachment to the Linking Assembly Unit, and each subscript n is independently selected from 4 to 72, 6 to 72, 8 to 72, 10 to 72, 12 to 72, 6 to 24, or 8 to 24. In some embodiments, subscript n is about 8, about 12, or about 24.

In some embodiments, the PEG Unit is added to the terminal attachment group (Q) of the Linking Assembly Unit. This can be achieved using a derivatized PEG unit with a terminal amine. In some embodiments, the derivatized PEG with a terminal amine is linked to the terminal attachment group (Q) of the linking assembly unit via 1-3 amino acids (e.g. a mono-, di-, or tri-peptide). For example, in some embodiments, the PEG Unit is linked to the terminal attachment group (Q) with a formula of: Q-glycine-PEG unit.

As described herein, the PEG Unit is selected such that it improves clearance of the resultant MD-ADC but does not significantly impact the ability of the Conjugate to penetrate into the tumor. In embodiments wherein the Drug Unit and Linking Assembly Unit of the MD-ADC has a hydrophobicity comparable to that of a maleimido glucuronide MMAE drug-linker, the PEG unit to be selected for use will preferably have from 8 subunits to about 24 subunits, more preferably about 12 subunits. In embodiments wherein the Drug Unit and Linking Assembly Unit of the MD-ADC has a hydrophobicity greater than that of a maleimido glucuronide MMAE drug-linker, a PEG Unit with more subunits is sometimes required.

In preferred embodiments of the present invention the PEG Unit is from about 300 daltons to about 5 kilodaltons; from about 300 daltons, to about 4 kilodaltons; from about 300 daltons, to about 3 kilodaltons; from about 300 daltons, to about 2 kilodaltons; or from about 300 daltons, to about 1 kilodalton. In some such aspects, the PEG Unit has at least 6 subunits or at least 8, 10 or 12 subunits. In some such aspects, the PEG Unit has at least 6 subunits or at least 8, 10 or 12 subunits but no more than 72 subunits, preferably no more than 36 subunits.

In preferred embodiments of the present invention, apart from the PEG Unit, there are no other PEG subunits present in the Drug Linking Assembly Unit (i.e., no PEG subunits in any of the other components of the Conjugates and intermediates thereto as provided herein). In other embodiments of the present invention, apart from the PEG Unit, there are no more than 8, no more than 7, no more than 6, no more than 5, no more than 4, no more than 3, no more than 2 or no more than 1 other polyethylene glycol subunits present in the Drug Linking Assembly Unit (i.e., no more than 8, 7, 6, 5, 4, 3, 2, or 1 other polyethylene glycol (—$OCH_2CH_2$—) subunits in other components of the Conjugates and intermediates thereto as provided herein.)

It will be appreciated that when referring to PEG subunits, and depending on context, the number of subunits can represent an average number, e.g., when referring to a population of MD-ADCs or Intermediate Compounds, and using polydisperse PEGs.

Drug Units ($D^1$ and $D^2$)

Two or more Drug Units for which there are two different Drug Unit ($D^1$+$D^2$) are covalently attached to the LA Unit via the Attachment Groups ($Q^1$ or $Q^2$). As referenced in the previous section, in some embodiments, the LA Unit includes Optional Linking Groups ($L^1$ and $L^2$). It is understood that the Optional Linking Group may be attached to the drug moiety prior to LA Unit attachment, or the Optional Linking Group may be attached to the LA Unit prior to drug moiety attachment.

The effects of the present invention will be more pronounced in embodiments wherein the Drug Units are hydrophobic in nature. Accordingly, free drugs of the present invention are preferably hydrophobic in nature.

The Drug Unit (D) is that of a cytotoxic or cytostatic drug, also referred to herein as a cytotoxic or cytostatic agent. The Drug Unit has an atom that provides a covalent bond with the first or second Attachment Group ($Q^1$ or $Q^2$). In some embodiments, the Drug Unit ($D^1$ or $D^2$), has a nitrogen atom that can form a bond with the first or second Attachment Group ($Q^1$ or $Q^2$), respectively. In other embodiments, the Drug Unit ($D^1$ or $D^2$) has a carboxylic acid moiety providing a bond with the first or second Attachment Group ($Q^1$ or $Q^2$). In other embodiments, the Drug Unit ($D^1$ or $D^2$), contains a sulfhydryl functional group residue that provides a bond with the first or second Attachment Group ($Q^1$ or $Q^2$). In still other embodiments, the Drug Unit has a hydroxyl or ketone functional group residue that provides a bond with the first or second Attachment Group ($Q^1$ or $Q^2$).

Useful classes of cytotoxic agents include, for example, antitubulin agents, DNA minor groove binders, DNA replication inhibitors, alkylating agents, antibiotics, antifolates, antimetabolites, chemotherapy sensitizers, topoisomerase inhibitors, vinca alkaloids, or the like. Particularly examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids, taxanes, benzodiazepines or benzodiazepine containing drugs (e.g., pyrrolo[1,4]-benzodiazepines (PBDs), indolinobenzodiazepines, and oxazolidinobenzodiazepines) and vinca alkaloids. Select benzodiazepine containing drugs are described in WO 2010/091150, WO 2012/112708, WO 2007/085930, and WO 2011/023883.

In some embodiments, at least one Drug Unit is an auristatin. In some embodiments, all Drugs Units are auristatins. In some embodiments, at least one Drug Unit is MMAE, Auristatin T, MMAF or Dolastatin 10. In some embodiments, all Drug Units are MMAE, Auristatin T, MMAF or Dolastatin 10. In some embodiments, the Drug Units are MMAE and MMAF.

In some embodiments, at least one Drug Unit is MMAE, camptothecin, Superdox, Dolastatin 10, Vinblastine and Ciprofloxacin.

In certain embodiments, the cytotoxic agent is maytansine or a maytansinoid (e.g., DM1, DM4) another group of anti-tubulin agents. (ImmunoGen, Inc.; see also Chari et al., 1992, Cancer Res. 52:127-131 and U.S. Pat. No. 8,163,888).

In some embodiments, the Drug is a benzodiazepine (including benzodiazepine containing drugs e.g., pyrrolo[1,4]benzodiazepines (PBDs), indolinobenzodiazepines, and oxazolidinobenzodiazepines).

PBDs are of the general structure:

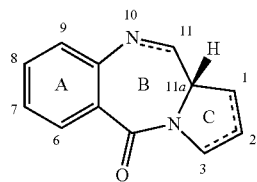

but differ in the number, type and/or position of substituents, in either or both their aromatic A rings and pyrrolo C rings, and/or in the degree of saturation of the C ring. In the B-ring there is either an imine (N=C), a carbinolamine(NH—CH (OH)), or a carbinolamine alkyl ether (NH—CH(Oalkyl)) at the $N^{10}$—$C^{11}$ positions, which is the electrophilic center responsible for alkylating DNA. All of the known natural products have an (S)-orientation at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumor agents. The biological activity of these molecules are sometimes potentiated by, for example, joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand cross-link which is thought to be mainly responsible for their biological activity.

The Drug Unit ($D^1$ or $D^2$), in some embodiments, are of different auristatin or non-auristatin conjugated drugs having a hydrophobicity comparable to or greater than monomethyl auristatin E. In other embodiments the two different Drug Units are selected so that the $IC_{50}$ values of the $D^1$ and $D^2$ are within 1 to 2 log units, more preferably with 0.5 to 1 log units, of each other, or have a disparity between these values that are compensatable by appropriate selection of the $D^1/D^2$ ratio on a DLA so that an effective amount of each drug is being simultaneously or near simultaneously delivered to the desired sites of intracellular action. In preferred embodiments, $D^1$ or $D^2$ is of MMAE or an auristatin having a hydrophobicity comparable to or greater than monomethyl auristatin E. The $D^1$ or $D^2$ auristatin Drug Unit is covalently attached to a first or second Attachment Group ($Q^1$ or $Q^2$), respectively, for example, via its N or C terminus. MMAE has a S log P value of 2.59. In more preferred embodiments, drugs to be used as $D^1$ or $D^2$ Drug Units in the present invention will have a S log P value of 1.5 or greater, 2.0 or greater, or 2.5 or greater. In some aspects, drugs to be used as $D^1$ or $D^2$ Drug Units in the present invention will have a S log P value from (a) about 1.5, about 2, or 2.5 to about 7, (b) about 1.5, about 2, or 2.5 to about 6, (c) about 1.5, about 2 or about 2.5 to about 5, (d) about 1.5, about 2, or 2.5 to about 4, or (e) about 1.5, about 2 or about 2.5 to about 3.

An auristatin $D^1$ or $D^2$ Drug Unit preferably has Formula $D_E$ as shown below wherein attachment to the first or second Attachment Group ($Q^1$ or $Q^2$) is via the N terminus:

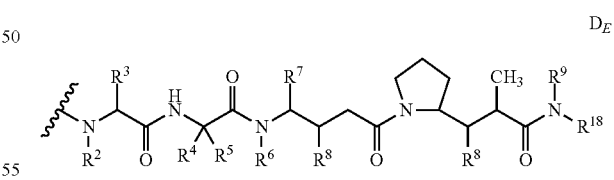

wherein, independently at each location:

$R^2$ is selected from the group consisting of H and $C_1$-$C_8$ alkyl;

$R^3$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from the group consisting of H and methyl;

or $R^4$ and $R^5$ jointly form a carbocyclic ring and have the formula $-(CR^aR^b)_n-$ wherein Re and $R^b$ are independently selected from the group consisting of H, $C_1$-$C_8$ alkyl and $C_3$-$C_8$ carbocycle and n is selected from the group consisting of 2, 3, 4, 5 and 6;

$R^6$ is selected from the group consisting of H and $C_1$-$C_8$ alkyl;

$R^7$ is selected from the group consisting of H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from the group consisting of H, OH, $C_1$-$C_8$ alkyl, $C_3$-$C_8$ carbocycle and O—($C_1$-$C_8$ alkyl);

$R^9$ is selected from the group consisting of H and $C_1$-$C_8$ alkyl;

$R^{1s}$ is selected from the group consisting of $-C(R^8)_2-$ $C(R^8)_2$-aryl, $-C(R^8)_2-C(R^8)_2-C_3$-$C_8$ heterocycle), and $-C(R^8)_2-C(R^8)_2-(C_3$-$C_8$ carbocycle).

MMAE conjugated via its N terminus is shown below:

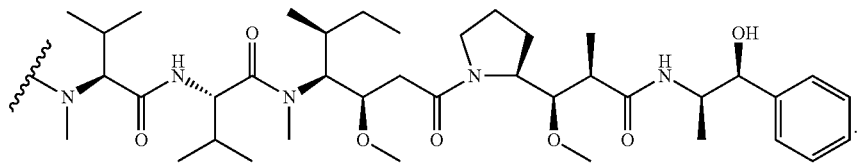 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

In some embodiments, the $D^1$ or $D^2$ Drug Unit is that of a vinca compound, a camptothecin or a anthracyclin cytotoxic compound. Example structures of those Drug Units when present in a -$L^1$-$D^1$ or -$L^2$-$D^2$ moiety are described herein for drug-linker intermediates.

In some embodiments, $D^1$ and $D^2$ are a drug pair selected from the group consisting of MMAE/MMAF, MMAE/camptothecin, Superdox/camptothecin, Superdox/MMAE, Dolastatin 10/MMAE, Dolastatin 10/MMAF, Vinblastine/MMAE, and Vinblastine/MMAF.

There are a number of different assays that can be used for determining whether a MD-ADC exerts a cytostatic or cytotoxic effect on a cell line. In one example for determining whether a MD-ADC exerts a cytostatic or cytotoxic effect on a cell line, a thymidine incorporation assay is used. For example, cells at a density of 5,000 cells/well of a 96-well plated is cultured for a 72-hour period and exposed to 0.5 µCi of $^3$H-thymidine during the final 8 hours of the 72-hour period, and the incorporation of $^3$H-thymidine into cells of the culture is measured in the presence and absence of MD-ADC. The MD-ADC has a cytostatic or cytotoxic effect on the cell line if the cells of the culture have reduced $^3$H-thymidine incorporation compared to cells of the same cell line cultured under the same conditions but not contacted with the MD-ADC.

In another example, for determining whether a MD-ADC exerts a cytostatic or cytotoxic effect on a cancer cell line, cell viability is measured by determining in a cell the uptake of a dye such as neutral red, trypan blue, or ALAMAR™ blue (see, e.g., Page et al., 1993, *Intl. J. of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Nat'l Cancer Inst.* 82:1107-12). Preferred MD-ADCs include those with an $IC_{50}$ value (defined as the mAB concentration that gives 50% cell kill) of less than 1000 ng/ml, preferably less than 500 ng/ml, more preferably less than 100 ng/ml, even most preferably less than 50 or even less than 10 ng/ml on the cell line.

General procedures for linking a drug to linkers are known in the art. See, for example, U.S. Pat. Nos. 8,163,888, 7,659,241, 7,498,298, U.S. Publication No. US20110256157 and International Application Nos. WO2011023883, and WO2005112919.

Antibodies (Ab) and (Ab*)

Antibodies useful in the MD-ADCs described herein are essentially any antibodies having four available inter-chain disulfide linkages, or the eight thiols that are produced by reduction of those inter-chain disulfide linkages for MD-ADCs having $D^1$+$D^2$ ranging from 2 to 16 when in 1:1 ratio. The antibodies are generally non-engineered antibodies—antibodies in which no modifications are made to introduce additional amino acids or peptides, but in some embodiments are genetically engineered to contain a conjugatable cysteine residue for MD-ADCs having $D^1$+$D^2$ ranging from 2 to 32 when in 1:1 ratio.

In some embodiments, the antibodies of the present disclosure include one or more engineered cysteine (eCys) residues. An eCys residue is a cysteine amino acid or a derivative thereof that is incorporated into the heavy chain or light chain of an antibody, typically the one or more eCys residues are incorporated into the antibody by mutagenizing the parent antibody. Further information can be found in U.S. Pat. No. 9,000,130, the contents of which is incorporated herein for all purposes. In some embodiments, derivatives of cysteine (Cys) include, but are not limited to beta-2-Cys, beta-3-Cys, homocysteine, and N-methyl cysteine.

In one group of embodiments, the multi-drug antibody drug conjugates (MD-ADCs) are represented by Formula (I):

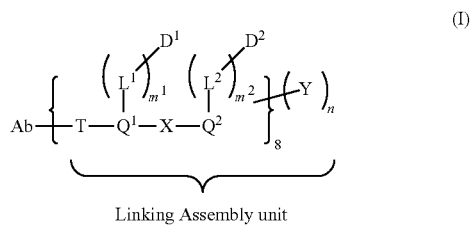

wherein

Ab is an antibody that is a non-engineered antibody;

T is a Tethering Group attached to a the sulfur atom of a thiol produced by reduction of the antibody's interchain disulfide linkages;

$Q^1$ is a first Attachment Group;
$Q^2$ is a second Attachment Group;
X is an Attachment Group Linker;
$D^1$ is a first Drug Unit;
$D^2$ is a second Drug Unit;
$L^1$ is an Optional Linking Group joining $D^1$ to $Q^1$;
$L^2$ is an Optional Linking Group joining $D^2$ to $Q^2$;
subscripts $m^1$ and $m^2$ are each independently 0 or 1;
Y is a Partitioning Agent; and
subscript n is 0 or 1.

In another group of embodiments, the MD-ADC is represented by formula (II):

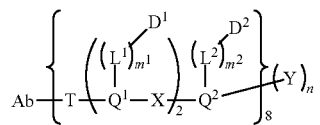

(II)

wherein
Ab is an antibody that is a non-engineered antibody;
T is a Tethering Group attached to the sulfur atom of a thiol produced by reduction of the antibody's interchain disulfide linkages;
$Q^1$ is a first Attachment Group;
$Q^2$ is a second Attachment Group;
X is an Attachment Group Linker;
$D^1$ is a first Drug Unit;
$D^2$ is a second Drug Unit;
$L^1$ is an Optional Linking Group joining $D^1$ to $Q^1$;
$L^2$ is an Optional Linking Group joining $D^2$ to $Q^2$;
subscripts $m^1$ and $m^2$ are each independently 0 or 1;
Y is a Partitioning Agent; and
subscript n is 0 or 1.

In yet another group of embodiments, the MD-ADC is represented by the Formula (III):

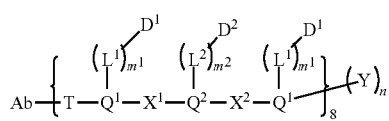

(III)

wherein
Ab is an antibody that is a non-engineered antibody;
T is a Tethering Group attached to a sulfur atom of a thiol produced by reduction of the antibody's interchain disulfide linkages;
each $Q^1$ is an independently selected first Attachment Group;
$Q^2$ is a second Attachment Group;
$X^1$ and $X^2$ are each an independently selected Attachment Group Linker;
$D^1$ is a first Drug Unit;
$D^2$ is a second Drug Unit;
each $L^1$ is an independently selected Optional Linking Group joining $D^1$ to $Q^1$;
$L^2$ is an Optional Linking Group joining $D^2$ to $Q^2$;
the subscripts $m^1$ and $m^2$ are each independently 0 or 1;
Y is a Partitioning Agent; and
subscript n is 0 or 1.

In still another group of embodiments, the MD-ADC is represented by the Formula (IV):

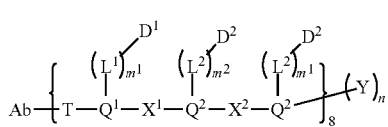

(IV)

wherein
Ab is an antibody that is a non-engineered antibody;
T is a Tethering Group attached to a sulfur atom of a thiol produced by reduction of the antibody's interchain disulfide linkages;
$Q^1$ is an first Attachment Group;
each $Q^2$ is an independently selected second Attachment Group;
$X^1$ and $X^2$ are each an independently selected Attachment Group Linker;
$D^1$ is a first Drug Unit;
$D^2$ is a second Drug Unit;
$L^1$ is an Optional Linking Group joining $D^1$ to $Q^1$;
each $L^2$ is an independently selected Optional Linking Group joining $D^2$ to $Q^2$;
subscripts $m^1$ and $m^2$ are each independently 0 or 1;
Y is a Partitioning Agent that is attached to a site on L, Q, $X^1$, $X^2$, $Q^2$, $L^1$ or $L^2$; and
subscript n is 0 or 1.

In each of the above described embodiments, L, Q, $Q^2$, $X^1$, $X^2$, $L^1$, $L^2$, $D^1$, $D^2$, and Y are as described in the preceding sections.

With reference to formulae (I), (II) (III), and (IV) above, suitable antibodies (Ab) are those that are intact or fully-reduced antibodies. The term 'fully-reduced' is meant to refer to antibodies in which all four inter-chain disulfide linkages have been reduced to provide eight thiols that can be attached to Tethering Groups (T).

In some embodiments, the Ab in formulae (I), (II) (III), and (IV) replaced with Ab*. Ab* is an antibody that comprises one or more engineered cysteine (eCys) residues, the eCys residues are free so that the thiols can be attached to the Tethering Group(s) (T). In such embodiments, T is a Tethering Group attached to a sulfur atom of an engineered cysteine or derivative thereof in an antibody's heavy chain or light chain, and in some embodiments is also attached to thiol(s) produced by reduction of interchain disulfide linkages in said antibody.

In one group of embodiments, the antibody is directed against a cancer cell antigen. In another group of embodiments, the antibody is directed against a bacteria-related antigen. In yet another group of embodiments, the antibody is directed against an autoimmune cell antigen.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA*. 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immunospecifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Additionally, recombinant antibodies, such as chimeric and humanized monoclonal antibodies, comprising both human and non-human portions, which are preferably made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies are preferably produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-1043; Liu et al., 1987, *Proc. Natl. Acad. Sci. USA* 84:3439-3443; Liu et al., 1987, *J Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies are particularly desirable and are preferably produced using transgenic mice that are incapable of expressing endogenous immunoglobulin heavy and light chains genes, which in some embodiments express human heavy and light chain genes.

Antibodies immunospecific for a cancer cell antigen are preferably obtained commercially or produced by any method known to one of skill in the art such as, e.g., chemical synthesis or recombinant expression techniques. The nucleotide sequence encoding antibodies immunospecific for a cancer cell antigen is sometimes obtained, e.g., from the GenBank database or a database like it, the literature publications, and othertimes obtained by routine cloning and sequencing.

In a specific embodiment, known antibodies for the treatment of cancer are used. Antibodies immunospecific for a cancer cell antigen are sometimes obtained commercially and othertimes produced by any method known to one of skill in the art such as, e.g., recombinant expression techniques. The nucleotide sequence encoding antibodies immunospecific for a cancer cell antigen is sometimes obtained, e.g., from the GenBank database or a database like it, the literature publications, and othertimes by routine cloning and sequencing.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In some aspects, the antibody will specifically bind CD19, CD20, CD30, CD33, CD70, alpha-v-beta-6, Liv-1 or Lewis Y antigen.

The anti-CD30 antibody can be, for example, the chimeric AC10 antibody, brentuximab. The anti-CD30 antibody can have a heavy chain variable region having the amino acid sequence set forth in SEQ ID NO: 1, a light chain variable region having the amino acid sequence set forth in SEQ ID NO:2, a human gamma I constant region having the amino acid sequence set forth in SEQ ID NO:7 and a human kappa constant region having the amino acid sequence set forth in SEQ ID NO:8.

The anti-CD30 antibody preferably is a humanized AC10 antibody or has a heavy chain variable region having the amino acid sequence set forth in SEQ ID NO:9, a light chain variable region having the amino acid sequence set forth in SEQ ID NO: 10. Preferably, that antibody further comprises a human gamma I constant region having the amino acid sequence set forth in SEQ ID NO:7 optionally having a serine to cysteine substitution at position 239 (according to the EU index) and a human kappa constant region having the amino acid sequence set forth in SEQ ID NO:8.

The anti-CD70 antibody is preferably a humanized antibody (see, e.g., US 2009/0148942). In an exemplary embodiment, the anti-CD70 antibody has a heavy chain variable region having the amino acid sequence set forth in SEQ ID NO:3, and a light chain variable region having the amino acid sequence set forth in SEQ ID NO:4.

The anti-CD19 antibody is preferably a humanized antibody (see, e.g., US 2009/0136526 incorporated by reference herein in its entirety and for all purposes). In an exemplary embodiment, the hBU12 antibody has a heavy chain variable region having the amino acid sequence set forth in SEQ ID NO:5, and a light chain variable region having the amino acid sequence set forth in SEQ ID NO:6.

Another preferred antibody is a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 antibody (see, e.g., U.S. Pat. No. 8,257,706 incorporated by reference herein in its entirety and for all purposes).

Exemplary attachments to the antibody is via thioether linkages.

Cancer Cell Antigen Sites

Examples of antibodies available for the treatment of cancer include, but are not limited to, humanized anti-HER2 monoclonal antibody, HERCEPTIN® (trastuzumab; Genentech) for the treatment of patients with metastatic breast cancer; RrrUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, N.C.) which is a murine $IgG_{2a}$ antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., N.J.) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC 1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., Willner, D., Lasch, S. J., Henderson, A. J., Hofstead, S. J., Casazza, A. M., Firestone, R. A., Hellström, I., Hellström, K. E., "Cure of Xenografted Human Carcinomas by BR96-Doxorubicin Immunoconjugates" Science 1993, 261, 212-215), BR64 (Trail, P. A., Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" Cancer Research 1997, 57, 100-105, mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" Cancer Res. 2000, 60, 3225-3231), mAbs against the CD70 antigen, such as 1F6 mAb and 2F2 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" J. Immunol., 151, 5896-5906, 1993: Wahl et al., 2002 Cancer Res. 62(13):3736-42). Many other internalizing antibodies that bind to tumor associated antigens can be used and have been reviewed (Franke, A. E., Sievers, E. L., and Scheinberg, D. A., "Cell surface receptor-targeted therapy of acute myeloid leukemia: a review" Cancer Biother Radiopharm. 2000, 15, 459-76; Murray, J. L., "Monoclonal antibody treatment of solid tumors: a coming of age" Semin Oncol. 2000, 27, 64-70; Breitling, F., and Dubel, S., Recombinant Antibodies, John Wiley, and Sons, New York, 1998).

Select Embodiments of Linking Assembly Units and MD-ADCs

The Drug Linking Assembly Unit represented by Formulas Ib, IIb, IIb, or IVb, wherein T comprises a maleimido group.

The Drug Linking Assembly Unit represented by Formulas Ib, IIb, IIb, or IVb, wherein T comprises a maleimido group, and each of X, $X^1$, $X^2$, $Q^1$, and $Q^2$ is an amino acid.

The Drug Linking Assembly Unit represented by Formulas Ib, IIb, IIb, or IVb, wherein n is 0 and Y is absent.

The Drug Linking Assembly Unit represented by Formulas Ia, IIa, IIa, or IVa, wherein n is 0, Y is absent, and each of $L^1$ and $L^2$ is independently selected from the group consisting of maleimido-caproyl (mc), maleimido-caproyl-valine-citrulline (mc-vc), and maleimido-caproyl-valine-citrulline-para-aminobenzyloxycarbonyl (mc-vc-PABC).

The Drug Linking Assembly Unit represented by Formulas Ia, IIa, IIa, or IVa, wherein T is a self-stabilizing linker.

The Drug Linking Assembly Unit represented by Formulas Ia, IIa, IIa, or IVa, wherein T is a MDPr-vc linker.

Exemplary Drug Linking Assembly Units provided herein are those units that contain two Drug Units ($D^1$ and $D^2$) and include those represented by the following structures:

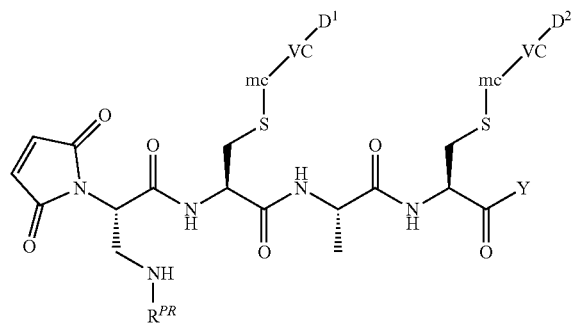
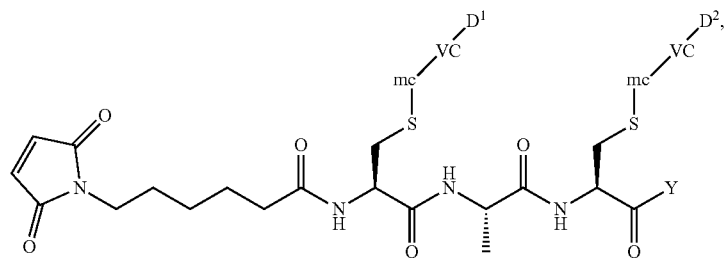
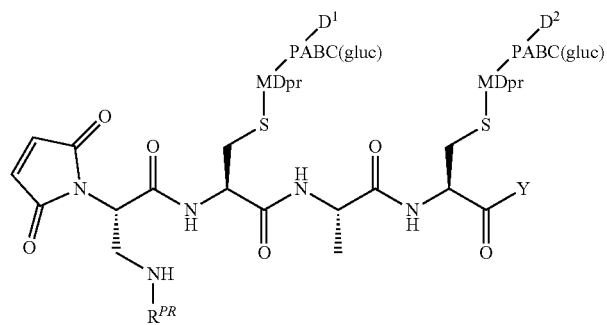
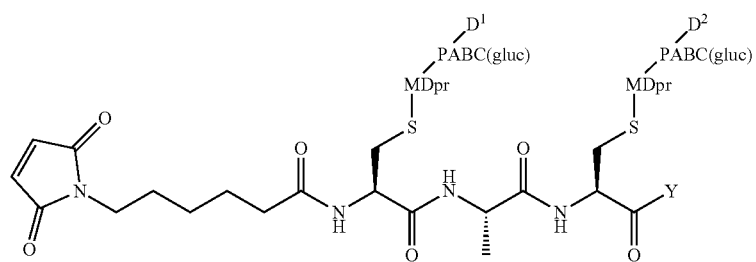

and those structures wherein mc-VC-PABC-$D^1$ is replaced with mc-VA-PABC-$D^1$ or mc-VA-$D^1$ or any other L-$D^1$ unit; and/or mc-VC-PABC-$D^2$ is replaced with mc-VA-PABC-$D^2$ or mc-VA-$D^2$ or any other $L^2$-$D^2$ unit;

and wherein RR is hydrogen or a protecting group, e.g., acid labile protecting group, e.g., BOC;

For ease of reference to the compounds and assemblies described herein, the component mc-VC-PABC-D has the structure of:

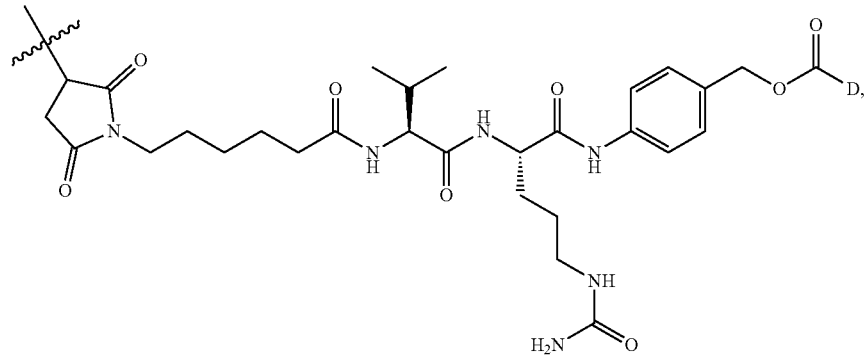

the component mc-VA-PABC-D has the structure of:

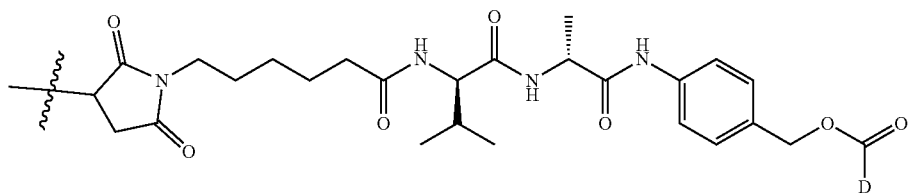 [SMILES: *C1CC(=O)N(CCCCCC(=O)N[C@@H](C(=O)N[C@H](C)C(=O)Nc2ccc(COC([2H])=O)cc2)C(C)C)C1=O]

the component mc-VA-D has the structure of:

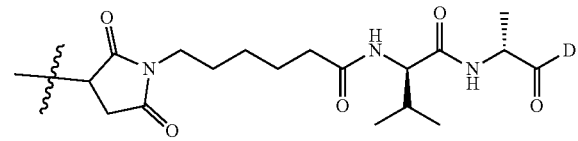 [SMILES: *C1CC(=O)N(CCCCCC(=O)N[C@@H](C(=O)N[C@H](C)C([2H])=O)C(C)C)C1=O]

and the component MDPr-PABC(gluc)-D has the structure of:

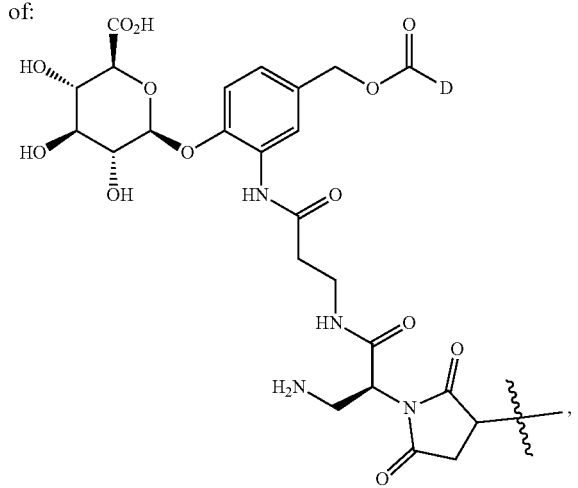

wherein mc-VC-PABC-D, mc-VA-PABC-D, mc-VA-D, and MDPr-PABC(gluc)-D are exemplary -$L^1$-$D^1$ or -$L^2$-$D^2$ moieties bonded to a Drug Linking Assembly Unit (DLA) by means of Attachment Groups ($Q^1$ and $Q^2$), and wherein the wavy line indicates covalent bonding of the succinimide ring of mc or MDPr to a thiol present on either of $Q^1$ or $Q^2$;

In some embodiments, an mc moiety in mc-VC-PABC-D, mc-VA-D, and mc-VA-PABC-D, wherein the mc moiety has the structure of

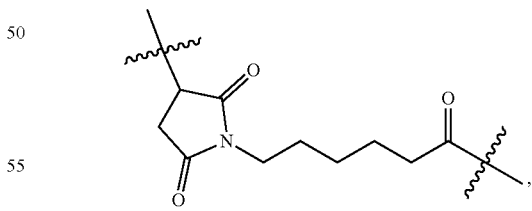

wherein the wavy line to the succinimide moiety indicates covalent bonding to the Drug Linking Assembly Unit (DLA) via Attachment groups $Q^1$ and $Q^2$), and wherein the wavy line adjacent to the carbonyl indicates covalent bonding to the remainder of -D or -$D^2$. In any of the above structures, the mc moiety may be replaced with the MDPr moiety, which has the structure of

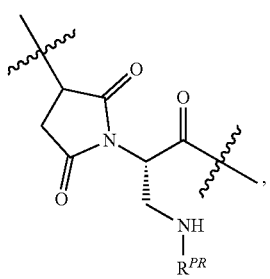

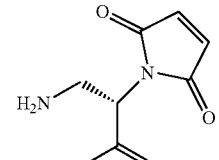

wherein $R^{PR}$ is hydrogen or a protecting group, to provide MDPr-VC-PABC-D, MDPr-VA-D and MDPr-VA-PABC-D, which are further exemplary -$L^1$-$D^1$ or -$L^2$-$D^2$ moieties.

In some embodiments, a Drug Linking Assembly Unit has the Formula (XIIIa):

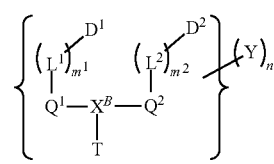

(XIIIa)

wherein

T is a Tethering Group that can be attached to a sulfur atom of an engineered cysteine in said antibody's heavy chain or light chain or to a thiol produced by reduction of an antibody's interchain disulfide linkage;

$Q^1$ is a first Attachment Group;

$Q^2$ is a second Attachment Group;

$X^B$ is a branched Attachment Group Linker;

$D^1$ is a first Drug Unit $D^2$ is a second Drug Unit;

$L^1$ is an Optional Linking Group joining $D^1$ to $Q^1$;

$L^2$ is an Optional Linking Group joining $D^2$ to $Q^2$;

subscripts $m^1$ and $m^2$ are each independently 0 or 1;

Y is a Partitioning Agent that is attached to a site on L, Q, $X^B$, $Q^2$, $L^1$ or $L^2$; and subscript n is 0, 1, or 2.

Other exemplary Drug Linker Assembly Units of the present invention that provide 2X the drug loading include the following

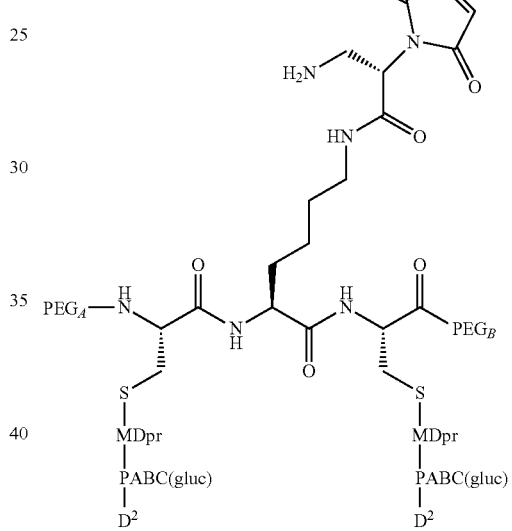

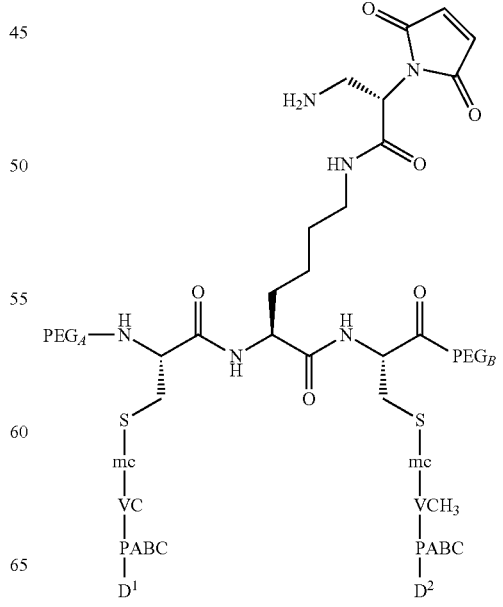

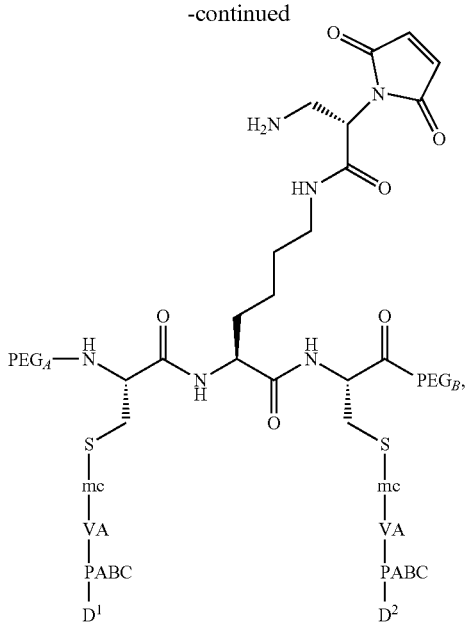

wherein mc-VA-D, mc-VC-PABC-D, mc-VA-PABC-D and MDPr-PABC(gluc)-D are exemplary -L¹-D¹ or -L²-D² moieties as described for the above 2X drug loading structures and wherein PEG$_A$ and PEG$_B$, independently selected, are as described in any of the embodiments for PEG Units provided herein. In some embodiments PEG$_A$ is a non-dispersive PEG Unit having the structure of

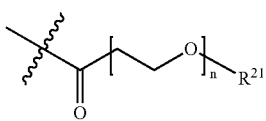

and/or PEG$_B$ is a nondispersive PEG Unit having the structure of

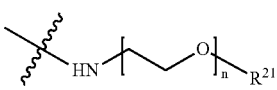

wherein each $R^{21}$ is an independently selected PEG capping unit, an each instance of n independently selected is an integer ranging from 8 to 24 or from 12 to 38. In preferred embodiment one $R^{21}$ is —CH$_3$ and the other is —CH$_2$CH$_2$CO$_2$H.

In some embodiments the mc moiety, which has the structure of

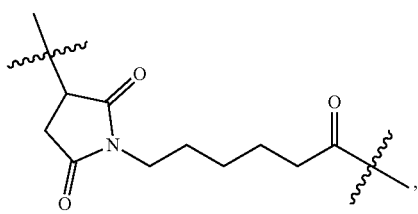 [SMILES: *C(=O)CCCCCN1C(=O)CC(*)C1=O]

in any of the above structures where that moiety is present is replaced with the MDPr moiety, which has the structure of

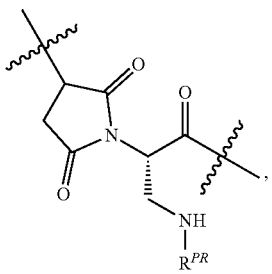

wherein RR is hydrogen or a protecting group, to provide MDPr-VC-PABC-D, MDPr-VA-D and MDPr-VA-PABC-D as -L¹-D¹ or -L²-D², In other embodiments the MDPr moiety in the above structure where that moiety is present is replaced with the mc moiety to provide mc-PABC(gluc)D as -L¹-D¹ or -L²-D².

It will be understood that the substituted succinimide in MDPr in any one of the MDPr-containing -L¹-D¹ or -L²-D² moieties may exist in hydrolyzed form (i.e., a water molecule is added across one and not both of the carbonyl-nitrogen bonds).

In some embodiments MDPr-PABC(gluc)-D as the -L¹-D¹ or -L²-D² moiety is replaced with mc-PABC(gluc)-D.

It will be understood that the substituted succinimide in MDPr in any one of the MDPr-containing -L¹-D¹ or -L²-D² moieties may exist in hydrolyzed form (i.e., a water molecule is added across one and not both of the carbonyl-nitrogen bonds). An -L¹-D¹ or -L²-D² moiety comprised of mc may also have its succinimide ring in hydrolyzed form.

Methods of Use

Treatment of Cancer

The MD-ADCs are useful for inhibiting the multiplication of a tumor cell or cancer cell, causing apoptosis in a tumor or cancer cell, or for treating cancer in a patient. The MD-ADCs can be used accordingly in a variety of settings for the treatment of cancers. The MD-ADCs can be used to deliver a drug to a tumor cell or cancer cell. Without being bound by theory, in one embodiment, the antibody of a MD-ADC binds to or associates with a cancer-cell or a tumor-cell-associated antigen, and the MD-ADC can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, via a cleavable mechanism, the drug is released within the cell. In an alternative embodiment, the Drug or Drug Unit is cleaved from the MD-ADC outside the tumor cell or cancer cell, and the Drug or Drug Unit subsequently penetrates the cell.

In one embodiment, the antibody binds to the tumor cell or cancer cell.

In another embodiment, the antibody binds to a tumor cell or cancer cell antigen which is on the surface of the tumor cell or cancer cell.

In another embodiment, the antibody binds to a tumor cell or cancer cell antigen which is an extracellular matrix protein associated with the tumor cell or cancer cell.

The specificity of the antibody for a particular tumor cell or cancer cell can be important for determining those tumors or cancers that are most effectively treated. For example, MD-ADCs that target a cancer cell antigen present in hematopoietic cancers can be useful treating hematologic malignancies (e.g., anti-CD30, anti-CD70, anti-CD19, anti-CD33 binding antibodies can be useful for treating hematologic malignancies). MD-ADCs that target an accessible cancer cell antigen present on solid tumors are useful treating such solid tumors.

Cancers treatable with a MD-ADC include, but are not limited to, hematopoietic cancers such as, for example, lymphomas (Hodgkin Lymphoma and Non-Hodgkin Lymphomas) and leukemias and solid tumors. Examples of hematopoietic cancers include, follicular lymphoma, anaplastic large cell lymphoma, mantle cell lymphoma, acute myeloblastic leukemia, chronic myelocytic leukemia, chronic lymphocytic leukemia, diffuse large B cell lymphoma, and multiple myeloma. Examples of solid tumors include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Multi-Modality Therapy for Cancer

Cancers, including, but not limited to, a tumor, metastasis, or other disease or disorder characterized by uncontrolled cell growth, can be treated or inhibited by administration of a MD-ADC.

In other embodiments, methods for treating cancer are provided, including administering to a patient in need thereof an effective amount of a MD-ADC and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. In some embodiments, an MD-ADC is administered to a patient that has also undergone surgery as treatment for the cancer.

In some embodiments, the patient also receives an additional treatment, such as radiation therapy. In a specific embodiment, the MD-ADC is administered concurrently with the chemotherapeutic agent or with radiation therapy. In another specific embodiment, the chemotherapeutic agent or radiation therapy is administered prior or subsequent to administration of a MD-ADC.

In other embodiments, the chemotherapeutic agent is administered over a series of sessions. Those embodiments include administration of any one or a combination of the chemotherapeutic agents, such a standard of care chemotherapeutic agent(s).

Additionally, methods of treatment of cancer with a MD-ADC are provided as an alternative to chemotherapy or radiation therapy where the chemotherapy or the radiation therapy has proven or can prove too toxic, e.g., results in unacceptable or unbearable side effects, for the subject being treated. The patient being treated is optionally treated with another cancer treatment such as surgery, radiation therapy or chemotherapy, depending on which treatment is found to be acceptable or bearable.

Treatment of Autoimmune Diseases

The MD-ADCs are useful for killing or inhibiting the replication of a cell that produces an autoimmune disease or for treating an autoimmune disease. The MD-ADCs can be used accordingly in a variety of settings for the treatment of an autoimmune disease in a patient. The MD-ADCs can be used to deliver a drug to a target cell. Without being bound by theory, in one embodiment, the MD-ADC associates with an antigen on the surface of a target cell, and the MD-ADC is then taken up inside a target-cell through receptor-mediated endocytosis. Once inside the cell, the Linker unit is cleaved, resulting in release of the Drug or Drug Unit. The released Drug is then free to migrate in the cytosol and induce cytotoxic or cytostatic activities. In an alternative embodiment, the Drug is cleaved from the MD-ADC outside the target cell, and the Drug or Drug Unit subsequently penetrates the cell.

In one embodiment, the antibody binds to an autoimmune antigen. In one aspect, the antigen is on the surface of a cell involved in an autoimmune condition.

In another embodiment, the antibody binds to an autoimmune antigen which is on the surface of a cell.

In one embodiment, the antibody binds to activated lymphocytes that are associated with the autoimmune disease state.

In a further embodiment, the MD-ADC kills or inhibit the multiplication of cells that produce an autoimmune antibody associated with a particular autoimmune disease.

Particular types of autoimmune diseases treatable with the MD-ADCs include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); and activated B lymphocyte-related disorders (e.g., systemic lupus erythematosus, Goodpasture's syndrome, rheumatoid arthritis, and type I diabetes).

Multi-Drug Therapy of Autoimmune Diseases

Methods for treating an autoimmune disease are also disclosed including administering to a patient in need thereof an effective amount of a MD-ADC and another therapeutic agent known for the treatment of an autoimmune disease.

Compositions and Methods of Administration

The present invention provides pharmaceutical compositions comprising the MD-ADCs described herein and a pharmaceutically acceptable carrier. The MD-ADCs are in any form that allows for the Conjugate to be administered to a patient for treatment of a disorder associated with expression of the antigen to which the antibody binds. For example, the Conjugates are preferably in the form of a liquid or solid. The preferred route of administration is parenteral. Parenteral administration includes subcutaneous injections, intravenous, intramuscular, intrasternal injection or infusion techniques. In one embodiment, the compositions are administered parenterally. In a preferred embodiment, the conjugates are administered intravenously. Administration is conducted by any convenient route, for example by infusion or bolus injection.

Pharmaceutical compositions are formulated so as to allow a compound to be bioavailable upon administration of the composition to a patient. Compositions will take the form of one or more dosage units, where for example, a tablet can be a single dosage unit.

Materials used in preparing the pharmaceutical compositions are non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The composition in some embodiments, is in the form of a liquid, preferably ones useful for delivery by injection. In a composition for administration by injection, one or more of a surfactant, preservative, wetting agent, dispersing agent, suspending agent, buffer, stabilizer and isotonic agent is optionally present.

The liquid compositions, whether they are solutions, suspensions or other like form, include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition is preferably enclosed in ampoule, a disposable syringe or a multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, and can be determined by standard clinical techniques. In addition, in vitro or in vivo assays are optionally employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition.

For intravenous administration, the composition preferably comprise from about 0.01 to about 100 mg of a MD-ADC per kg of the animal's body weight. In one embodiment, the composition includes from about 1 µg to about 100 mg of a MD-ADC per kg of the animal's body weight. In other embodiments, the amount administered will be in the range from about 0.1 to about 25 mg/kg of body weight of a compound.

Generally, the dosage of a conjugate administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The term "carrier" refers to a diluent, adjuvant or excipient, with which a compound is administered. Such pharmaceutical carriers include liquids, such as water and oils, including those of petroleum, animal, vegetable or synthetic origin, such as peanut oil, soybean oil, mineral oil, sesame oil. Other carriers include saline, gum acacia, gelatin, starch paste, talc, keratin, colloidal silica, urea. In addition, auxiliary, stabilizing, thickening, lubricating and coloring agents are optionally used. In one embodiment, when administered to a patient, the compound or compositions and pharmaceutically acceptable carriers are sterile. Water is an exemplary carrier when the compounds are administered intravenously. Saline solutions and aqueous dextrose and glycerol solutions are preferably employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Preferably, the carriers or vehicles for intravenous administration are sterile isotonic aqueous buffer solutions. Where necessary, the compositions can also include a solubilizing agent. Compositions for intravenous administration optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a conjugate is to be administered by infusion, it is dispensed, for example, with an infusion bottle containing sterile pharmaceutical grade water or saline. Where the conjugate is administered by injection, an ampoule of sterile water for injection or saline is provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Orthogonally Protected Antibody-Drug Conjugate Linkers

The present disclosure provides antibody-drug conjugate (ADC) linkers that are 'orthogonally' protected (i.e. protected to allow for selective deprotection when the attachment of a Drug Units is being carried out. Orthogonally protected antibody drug conjugated linkers are characterized as linking assembly (LA) units that include Protecting Groups on each Attachment Group (e.g. $Q^1$ and $Q^2$). As described in the Linking Assembly Unit section, Attachment Groups allow for the covalent attachment of the Drug Units; however, the Protecting Groups of the present disclosure block the covalent attachment of a Drug moiety to the linking assembly and are removable under specific conditions. Orthogonally protected Linking Assembly Unit are designed to incorporate different Protecting Groups allowing for selective deprotection and addition of a chosen Drug Unit.

In certain embodiments, orthogonally protected Linking Assembly Unit are characterized by the structure of Formula (Ib):

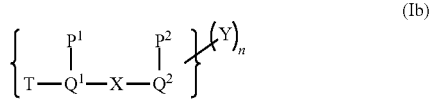

wherein

T is a Tethering Group which facilitates attachment to the antibody thiols produced by reduction of the antibody's interchain disulfide linkages;
$Q^1$ is a first Attachment Group that allows for covalent attachment of a first Drug Unit ($D^1$);
$Q^2$ is a second Attachment Group that allows for covalent attachment of a second Drug Unit ($D^2$);
$P^1$ is a first Protecting Group blocking the covalent attachment of first Drug Unit ($D^1$);
$P^2$ is a second Protecting Group blocking the covalent attachment of first Drug Unit ($D^1$), and $P^1$ and $P^2$ are different;
X is an Attachment Group Linker that provides a connection between two Attachment Groups;
Y is a Partitioning Agent; and
subscript n is 0 or 1.

In another group of embodiments, orthogonally protected Linking Assembly Unit are characterized by the structure of Formula (IIb):

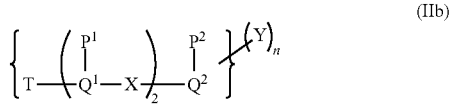

wherein

T is a Tethering Group which facilitates attachment to the antibody thiols produced by reduction of the antibody's interchain disulfide linkages;
each $Q^1$ is a first Attachment Group that allows for covalent attachment of a first Drug Unit ($D^1$);
$Q^2$ is a second Attachment Group that allows for covalent attachment of a second Drug Unit ($D^2$);
$P^1$ is a first Protecting Group blocking the covalent attachment of first Drug Unit ($D^1$);
$P^2$ is a second Protecting Group blocking the covalent attachment of first Drug Unit ($D^1$), and $P^1$ and $P^2$ are different;
X is an Attachment Group Linker;
Y is a partitioning group; and
subscript n is 0 or 1.

In yet another group of embodiments, orthogonally protected Linking Assembly Unit are characterized by the Formula (IIIb)

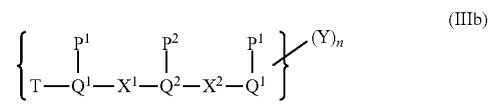

wherein

T is a Tethering Group which facilitates attachment to the antibody thiols produced by reduction of the antibody's interchain disulfide linkages;
each $Q^1$ is an independently selected a first Attachment Group that allow for covalent attachment of an independently selected first Drug Unit ($D^1$);
$Q^2$ is a second Attachment Group that allows for covalent attachment of a second Drug Unit ($D^2$);
$P^2$ is a first Protecting Group blocking the covalent attachment of first Drug Unit ($D^1$),
$P^2$ is a second Protecting Group blocking the covalent attachment of first Drug Unit ($D^1$), and $P^1$ and $P^2$ are different;
$X^1$ and $X^2$ are each an Attachment Group Linker;
Y is a partitioning group; and
subscript n is 0 or 1.

In still another group of embodiments, orthogonally protected Linking Assembly Unit are characterized by the Formula (IVb)

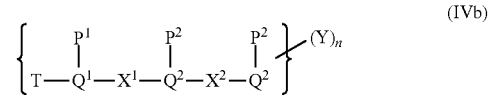

wherein

T is a Tethering Group having a terminal maleimido moiety;
$Q^1$ is a first Attachment Group comprising a first cysteine moiety or an analogue thereof;
$Q^2$ is a second Attachment Group comprising a second cysteine moiety or an analogue thereof;
$X^1$ and $X^2$ are each an Attachment Group Linker;
$P^1$ is a first thiol Protecting Group;
$P^2$ is a second thiol Protecting Group, and $P^1$ and $P^2$ are different;
Y is a Partitioning Agent attached to L, $Q^1$, X or $Q^2$; and
subscript n is 0 or 1.

In the orthogonally protected Linking Assembly Unit described herein, the Tethering Group (T), Attachment Groups ($Q^1$ and $Q^2$, Attachment Group Linkers (X, $X^1$, and $X^2$), optional Partitioning Agents (Y) are as defined in the preceding Linking Assembly Unit section. Once one or more Protecting Groups are selectively removed, a Drug Unit may be added to the selectively deprotected linker. As discussed in the Linking Assembly Unit section, Drug Units may include Optional Linking Groups $L^1$ and $L^2$.

In some embodiments of Formulas Ib, IIb, IIIb, and IVb, T is a Tethering Group having a terminal maleimido moiety.

In some embodiments of Formulas Ib, IIb, IIIb, and IVb, $Q^1$ is a first Attachment Group comprising a first cysteine moiety or an analogue thereof;

$Q^2$ is a second Attachment Group comprising a second cysteine moiety or an analogue thereof;

$P^1$ is a first thiol Protecting Group; and $P^2$ is a second thiol Protecting Group, and $P^1$ and $P^2$ are different.

Protecting Groups ($P^1$ and $P^2$)

'Orthogonal' deprotection (i.e. selective deprotection) of a Linker Assembly Unit having suitable protection allows for the synthesis of Drug Linker Assembly Units with a specifically desired ratio of $D^1$ to $D^2$ Drug Units and a mechanism to uniformly delivery this desired ratio of drugs to a target site. As such, Protecting Groups ($P^1$ and $P^2$) are selectively removable units which can attach to Attachment units ($Q^1$ and $Q^2$). In order for 'Orthogonal' deprotection, the identity of $P^1$ and $P^2$ are different.

In some embodiments $P^1$ and $P^2$ are thiol Protecting Groups. In some embodiments, $P^1$ is selected from the group consisting of —S-isopropyl (SiPr), —S-tert-butyl (StBu), and —S-methyl (SMe); and $P^2$ is —CH$_2$NH—C(O)CH$_3$ (acetamidomethyl).

In some embodiments, the orthogonally protected Linking Assembly Unit is represented by Formulas Ib, IIb, IIIb, or IVb, and T is MDPr-Val-Cit-; $P^1$ is selected from the group consisting of —S-isopropyl (SiPr), —S-tert-butyl (StBu), and —S-methyl (SMe); and $P^2$ is —CH$_2$NH—C(O)CH$_3$ (acetamidomethyl).

In some embodiments, the orthogonally protected Linking Assembly Unit is represented by Formulas Ib, IIb, IIIb, or IVb, and X is selected from the group consisting of glycine and alanine; T is MDPr-Val-Cit-; $P^1$ is selected from the group consisting of —S-isopropyl (SiPr), —S-tert-butyl (StBu), and —S-methyl (SMe); and $P^2$ is —CH$_2$NH—C(O)CH$_3$ (acetamidomethyl).

In some embodiments, the orthogonally protected Linking Assembly Unit is represented by Formulas Ib, IIb, IIIb, or IVb, and T is MDPr-Val-Cit-; $Q^1$ and $Q^2$ are each cysteine; X is glycine; $P^1$ is selected from the group consisting of —S-isopropyl (SiPr), —S-tert-butyl (StBu), and —S-methyl (SMe); and $P^2$ is —CH$_2$NH—C(O)CH$_3$ (acetamidomethyl).

In some embodiments, the orthogonally protected Linking Assembly Unit is represented by Formulas Ib, IIb, IIIb, or IVb, and T is MDPr-Val-Cit-; $Q^1$ and $Q^2$ are each cysteine; X is glycine; $P^1$ is selected from the group consisting of —S-isopropyl (SiPr), —S-tert-butyl (StBu), and —S-methyl (SMe); $P^2$ is —CH$_2$NH—C(O)CH$_3$ (acetamidomethyl); the subscript n is 1 and Y comprises a PEG or cyclodextrin group.

EXAMPLES

Unless otherwise noted, all solvents and reagents were purchased from commercial sources in the highest purity possible and not further purified prior to use. Anhydrous dimethylformamide (DMF) and CH$_2$Cl$_2$ were purchased from Aldrich. Fmoc-protected amino acids and 2-Cl-trityl-chloride resin (substitution 1 mmol/g, 200-300 mesh, 1% DVB) were purchased from Novabiochem. Fmoc-protected amino-dPEG$_{24}$-COOH was purchased from Quanta Biodesign. MDPr was prepared as described previously.[1] Maleimodocaproyl-MMAF (1), maleimidocaproyl-Val-Cit-PABC-MMAF (2), and maleimidocaproyl-Val-Cit-PABC-MMAE (3) were synthesized as previously described.[2] [3] Solid phase synthesis was performed in plastic syringes (National Scientific Company) fitted with a filter cut out of fritware PE medium grade porous sheet (Scienceware). Small molecule LC-MS was performed on a Waters Xevo G2 ToF mass spectrometer interfaced to a Waters Acquity H-Class Ultra Performance LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.7 mL/min). Preparative reverse-phase HPLC was performed on a Varian ProStar 210 solvent delivery system configured with a Varian ProStar 330 PDA detector. Products were purified over a Phenomenex Synergy MAX-RP 30.0×250 mm, 4 μm, 80 Å reverse phase column eluting with 0.05% trifluoroacetic acid in water (solvent A) and 0.0.5% trifluoroacetic acid in acetonitrile (solvent B). The purification methods generally consisted of linear gradients of solvent A to solvent B, ramping from 90% aqueous solvent A to 10% solvent A. The flow rate was 5.0 mL/min with monitoring at 220 nm.

(1)

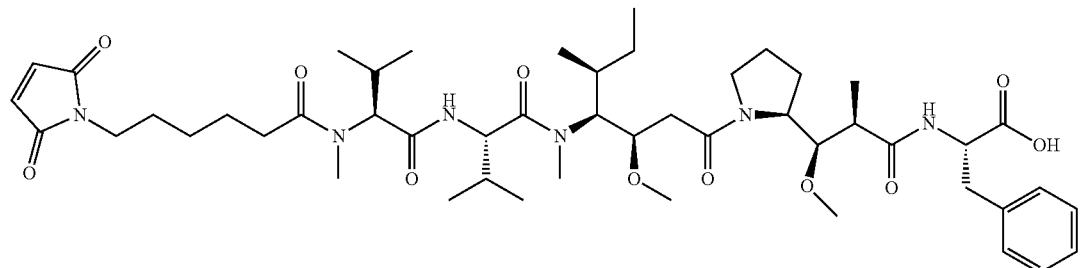

mc-MMAF

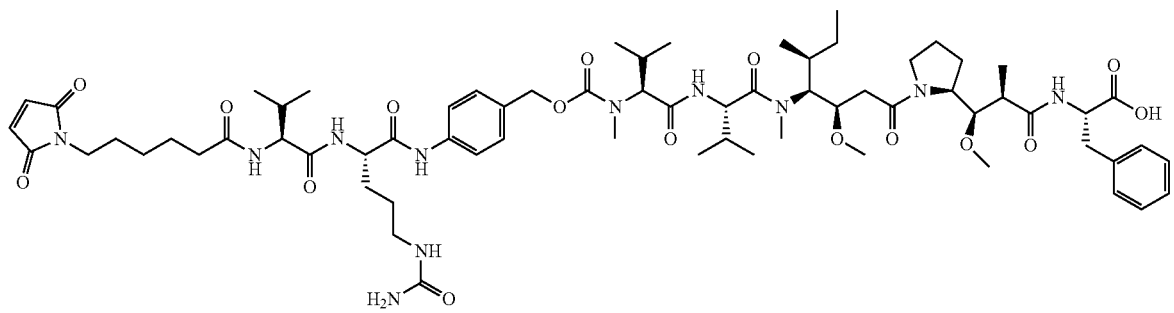

mc-vc-PABC-MMAF (2)

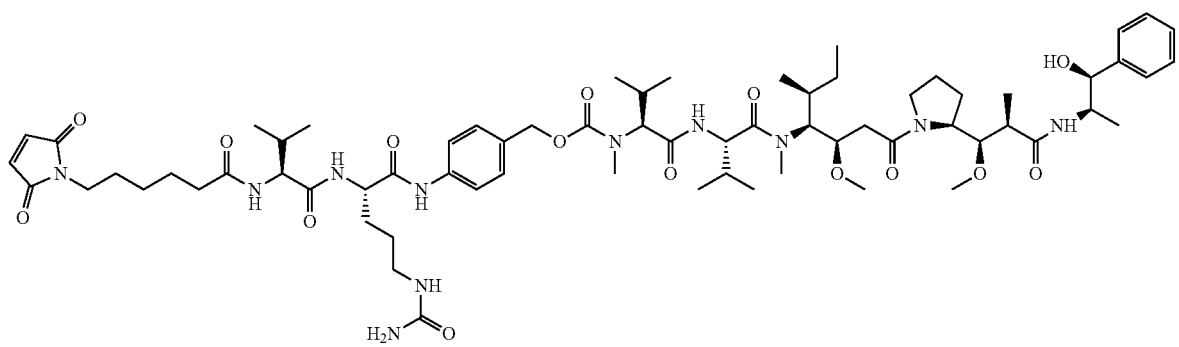

mc-vc-PABC-MMAE (3)

Example 1: Solid-Phase Peptide Synthesis

Both maleimidocaproyl-Cys(Acm) (mc-Cys(Acm)) and drug carrier 4 were synthesized on the solid phase using Fmoc chemistry.

General Procedure for Peptide Synthesis:

Resin loading: In a 10 mL solid phase reaction vessel (plastic syringe with PET frit) was added 0.15 g of 2-Cl-Tritylchloride resin (0.225 mmol) followed by a solution of Fmoc-amino acid or Fmoc-amino-PEG$_{24}$-COOH (0.225 mmol, 1.0 equiv) and N,N-diisopropylethylamine (DIPEA) (0.338 mmol, 1.5 equiv) in 3 mL of dry $CH_2Cl_2$. The vessel was shaken for 5 min, then more DIPEA (0.225 mmol, 1.0 equiv) was added, and the vessel was shaken for additional 30 min. Unreacted resin was quenched by adding MeOH (1.0 mL) for 5 min. Resin was then washed with DMF (5×5 mL), $CH_2Cl_2$ (5×5 mL), diethyl ether (5×5 mL) and dried in vacuo.

Fmoc removal procedure: Resin containing Fmoc-protected peptide was treated with 20% piperidine in DMF (5×3 mL) for 30 min total. The resin was then washed with DMF (5×5 mL) prior to further manipulation.

Standard coupling procedure: To the resin deprotected N-terminus amino acid (1 equiv), a solution containing Fmoc-amino acid or maleimido-acid (3 equiv), HATU (3 equiv), and DIPEA (6 equiv) in DMF (5 mL) was added. The reaction vessel was shaken for 1 hr. The resin was then washed with DMF (5×5 mL). Fmoc-Cys amino acids (1 equiv) were coupled by adding a solution containing Fmoc-Cys (4 equiv), hydroxybenzotriazole (HOBT) (4 equiv), and N,N'-diisopropylcarbodiimide (DIC) (4 equiv).

Cleavage from resin: To dried resin was added 2 mL of a solution of 10% trifluoroacetic acid(TFA) in $CH_2Cl_2$ that also contained 2.5% $H_2O$ and 2.5% triisopropyl silane in a 5 mL plastic syringe. After 1 min, the reaction mixture was transferred to a 20 mL borosilicate glass scintillation vial. This procedure was repeated three times. The cleavage solution was dried under a stream of $N_2$, washed 3× with 0.5 mL diethyl ether, then dried in vacuo. The crude products were either used without subsequent purification or purified by reverse-phase HPLC using the procedure described above.

Drug Carrier Characterization:

Maleimidocaproyl-Cys(Acm):

Expected exact mass: 385.13; observed m/z: 384.3 (M+H)$^+$, LC-MS $t_R$=0.66 min. The crude product was judged to be >95% pure and was used for antibody conjugation with no subsequent purification.

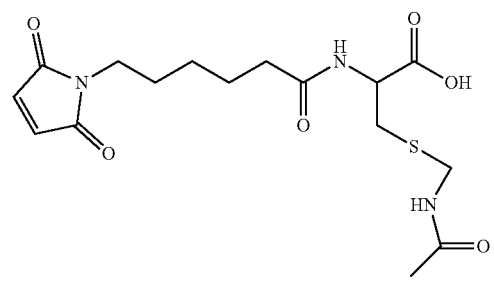 [SMILES: CC(=O)NCSCC(NC(=O)CCCCCN1C(=O)C=CC1=O)C(=O)O]

Drug Carrier 4:

Expected exact mass: 1833.9; observed m/z: 1835.1 (M+H)$^+$, LC-MS $t_R$=0.88 min, preparative LC $t_R$=24 min.

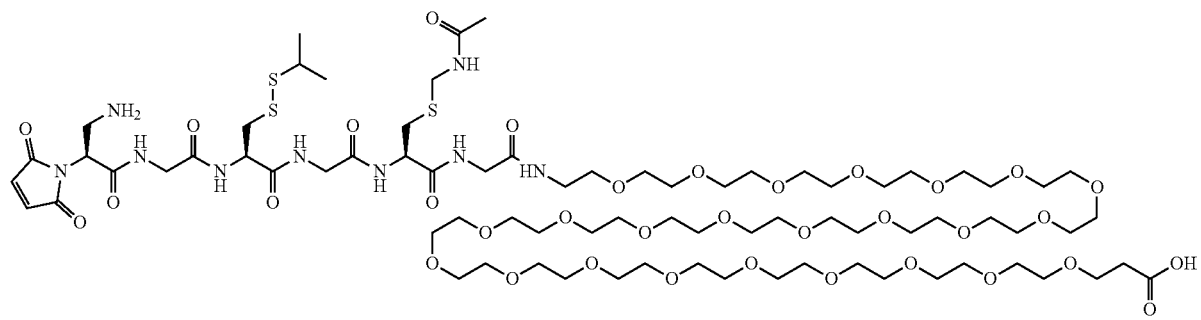 [SMILES: CC(=O)NCSC[C@H](NC(=O)CNC(=O)[C@H](CSSC(C)C)NC(=O)CNC(=O)[C@H](CN)N1C(=O)C=CC1=O)C(=O)NCC(=O)NCCOCCOCCOCCOCCOCCOCCOCCOCCOCCOCCOCCOCCOCCOCCOCCOCCOCCOCCOCCOCCOCCOCCOCCOCCC(=O)O]

Example 2: Conjugation Methods

Materials and General Methods

Chimeric anti-CD30 monoclonal antibody cAC10 was prepared as described previously.[4] Protein LC-MS data were acquired on a Waters Xevo GS-S QTOF coupled to a Waters Acquity H-Class UPLC system. Samples were reduced with 10 mM dithiothreitol (DTT) for 10 min at 37° C. and then chromatographed over an analytical reversed-phase column (Agilent Technologies, PLRP-S, 300Å, 2.1 mm ID×50 mm, 3 m) at 80° C. and eluted with a linear gradient of 0.01% TFA in acetonitrile from 25% to 65% in 0.05% aqueous TFA over 5 minutes, followed by isocratic 65% 0.01% TFA in acetonitrile for 0.5 min at a flow rate of 1.0 mL/min. Mass spectrometry data was acquired in ESI+ mode using a mass range of 500-4000 m/z and were deconvoluted using MaxEnt1 to determine masses of the resulting conjugates. The extent of aggregation of the conjugates was determined by size-exclusion chromatography (SEC) using an analytical SEC column (Sepax SRT-C 300 7.8 mm ID×30 cm, 5 μm) on a Waters 2695 HPLC system. The injected material was eluted using an isocratic mixture of 92.5% 25 mM sodium phosphate (pH 6.8), 350 mM NaCl, and 7.5% isopropyl alcohol at a flow rate of 1 mL/min.

ADCs were prepared by reduction of antibody interchain disulfides followed by addition of a 25-100% excess maleimide as described previously.[5] Full reduction of 8 thiols per antibody was accomplished by addition of 12 equivalents of tris(2-carboxyethyl)-phosphine (TCEP) to an antibody solution (1-10 mg/mL in PBS, pH 7.4). The extent of antibody reduction was monitored by reverse-phase LC-MS and additional TCEP was added as needed to complete the reaction. TCEP was then removed by ultrafiltration (3×, 10-fold dilution into PBS, pH 7.4 containing 1 mM EDTA, centrifugation at 4000×g through a 30-kDa MWCO filter). Fully reduced antibodies in PBS-EDTA were conjugated with 10-16 molar equivalents (25-100% excess) of drug-linker or drug-carrier as a 10 mM DMSO stock. The resulting solution was vortexed and left at room temperature for 10-20 minutes. The extent of conjugation was assessed by reverse-phase LC-MS as described above, and additional drug-linker or drug-carrier was added as needed. Once all available Cys thiols were alkylated, the crude ADC solution was purified by buffer exchange into PBS using either a Nap-5 desalting column (GE Healthcare) or through 3-5 rounds of ultrafiltration. The final ADC concentration was determined spectrophotometrically.

Conjugation and Trial Deprotection of Mc-Cys (ACm):

To fully reduced cAC10 antibody in PBS-EDTA was added 10 equiv. of mc-Cys(Acm) from a 100 mM DMSO stock. The resulting solution was vortexed and left at room temperature for 15 min. At this time, reverse-phase LC-MS indicated full alkylation of antibody thiols with no loss of fidelity of the Acm protecting group. The conjugate was purified by ultrafiltration according to the procedures described above, and the chromatography and mass spectrometric characterization of the conjugate is shown in FIG. 1A. The resulting conjugate cAC10-mc-Cys(Acm) with 8 carriers per antibody was then subjected to deprotection conditions. To the conjugate in PBS, pH 7.4 was added 50 equiv. of aqueous mercury acetate (Hg(OAc)$_2$) as a 10 mM stock. The reaction mixture was incubated for 45 min at room temperature. To the reaction mixture was added an aqueous slurry of Quadrasil MP resin (Sigma Aldrich, 0.025 mmol/g thiol capacity, 1 equiv. of resin to 1 equiv. mercury acetate added), and the mixture vortexed vigorously for 15 min. At this time, the mixture was centrifuged at 13,200×g for 2 min and the supernatant removed. To the supernatant was added 10-20 equiv. of N-ethylmaleimide (NEM) to cap the liberated cysteine thiols. The extent of modification was observed by LC-MS. As shown in FIG. 1B, a conjugate was produced where all 8 Acm groups had been removed and each liberated thiol was capped with NEM.

Example 3: General Procedure for Dual-Modified Antibody Conjugates

Carrier 4 Conjugation:

To fully reduced cAC10 antibody in PBS-EDTA was added 16 equiv. of carrier 4 from a 10 mM DMSO stock. The resulting solution was vortexed and left at room temperature for 15 min. At this time, reverse-phase LC-MS indicated full alkylation of antibody thiols with no loss of fidelity of the Acm protecting group. The conjugate was purified by ultrafiltration according to the procedures described above.

Figure 2:
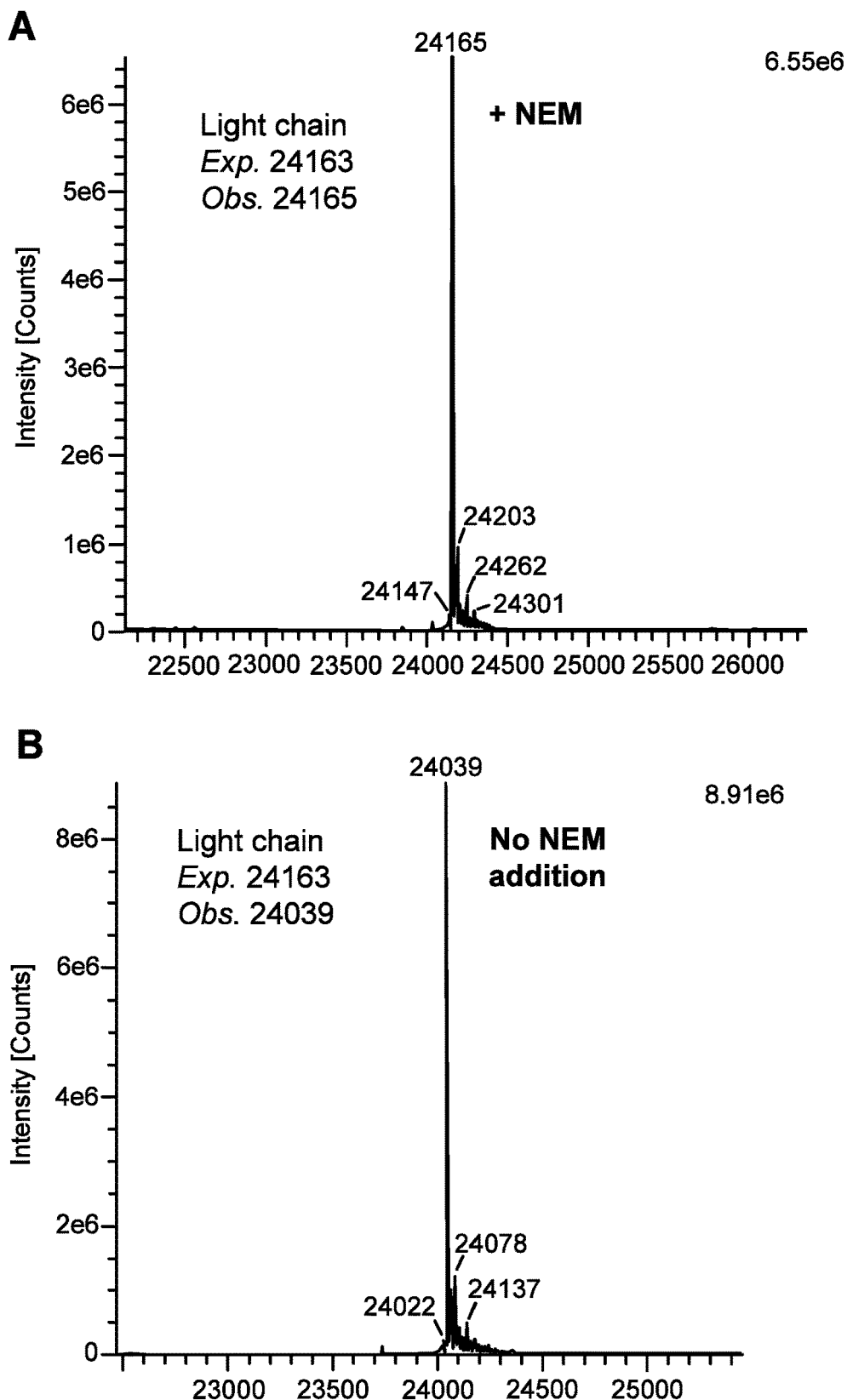
FIGS. 2A and 2B shows the deconvoluted light chain mass of cAC10-mc-Cys after acetamidomethyl (Acm) deprotection and subsequent N-ethyl maleimide (NEM) addition, which either included prior treatment with QMP resin (A) or did not (B). Addition of NEM to the liberated thiol was only observed in (A).
Figure 3:
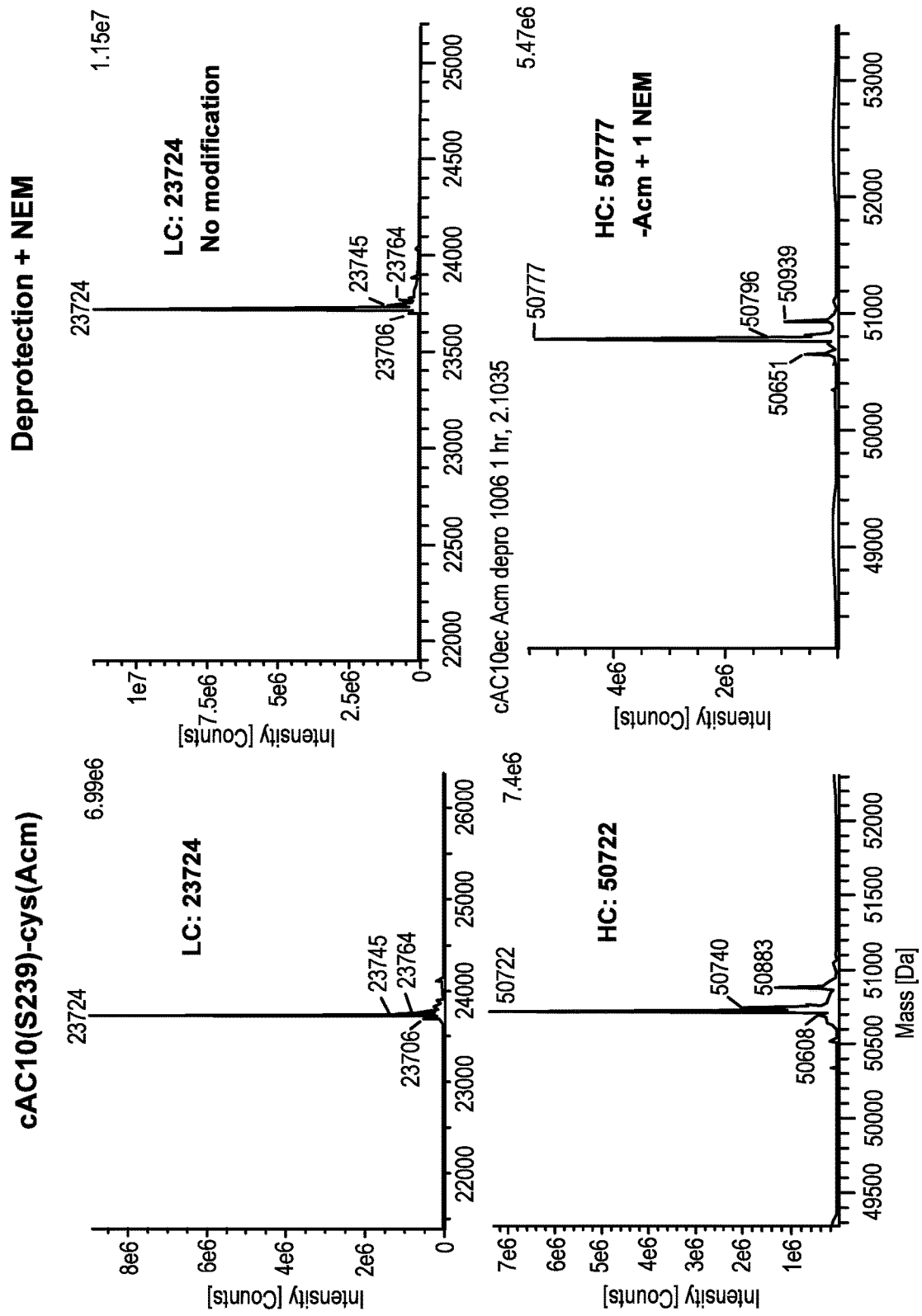
FIG. 3 shows that mercury-mediated Acm deprotection does not affect antibody interchain disulfide integrity. Maleimidocaproyl-Cys(Acm) was conjugated to cAC10(S239C) at 2 carriers per antibody. This conjugate had all interchain disulfide bonds intact. The conjugate was subjected to mercury-mediated Acm deprotection conditions and subsequent N-ethyl maleimide (NEM) conjugation (ca. 20 molar equivalents). Shown are the deconvoluted light and heavy chain mass spectra following reverse-phase separation of light and heavy chains. This analysis demonstrates that only a single NEM molecule was added to the heavy chain and no modification of the light chain occurred. This indicates that mercury treatment does not affect antibody interchain disulfides. If mercury treatment disrupted the disulfide bonds, multiple NEM additions would be expected. Note that multiple heavy chain mass species are present due to heterogeneity in the N-linked glycan. Only the G0 glycoform mass is noted for the heavy chain. LC=light chain, HC=heavy chain
Figure 4:
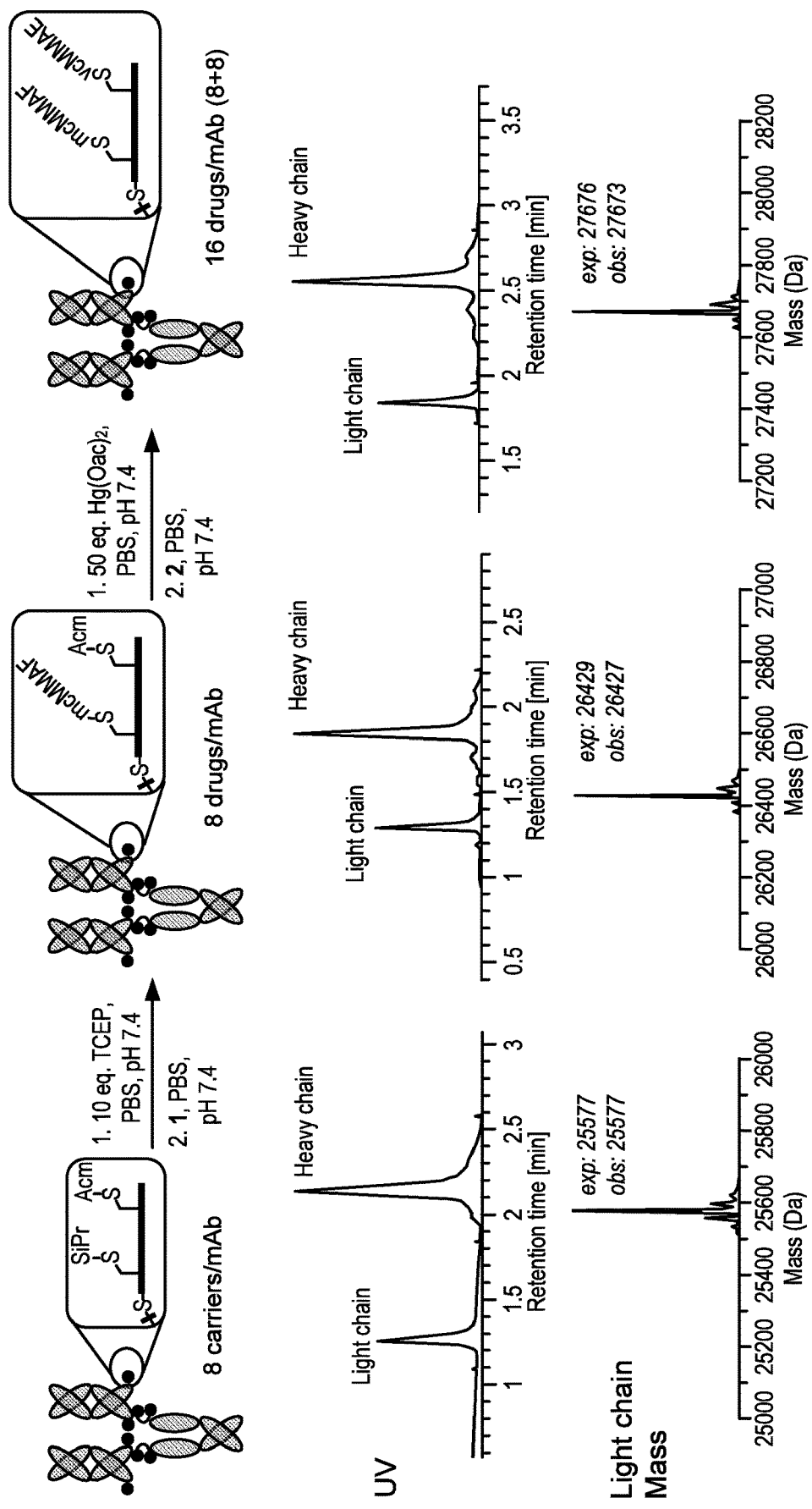
FIG. 4 shows a reaction schematic that includes the conditions for sequential unmasking of Cys(SiPr) and Cys (Acm) residues on carrier 4 and the resulting site-specific drug-linker conjugation. Each conjugate was analyzed by reverse-phase UPLC-MS. Shown below each intermediate is the UV chromatogram following reverse-phase separation, and the de-convoluted light chain mass. Each step proceeded with near quantitative conversion, yielding largely a single light and heavy chain species. The de-convoluted heavy chain mass for each conjugate is provided in FIG. 6.
Figure 5:
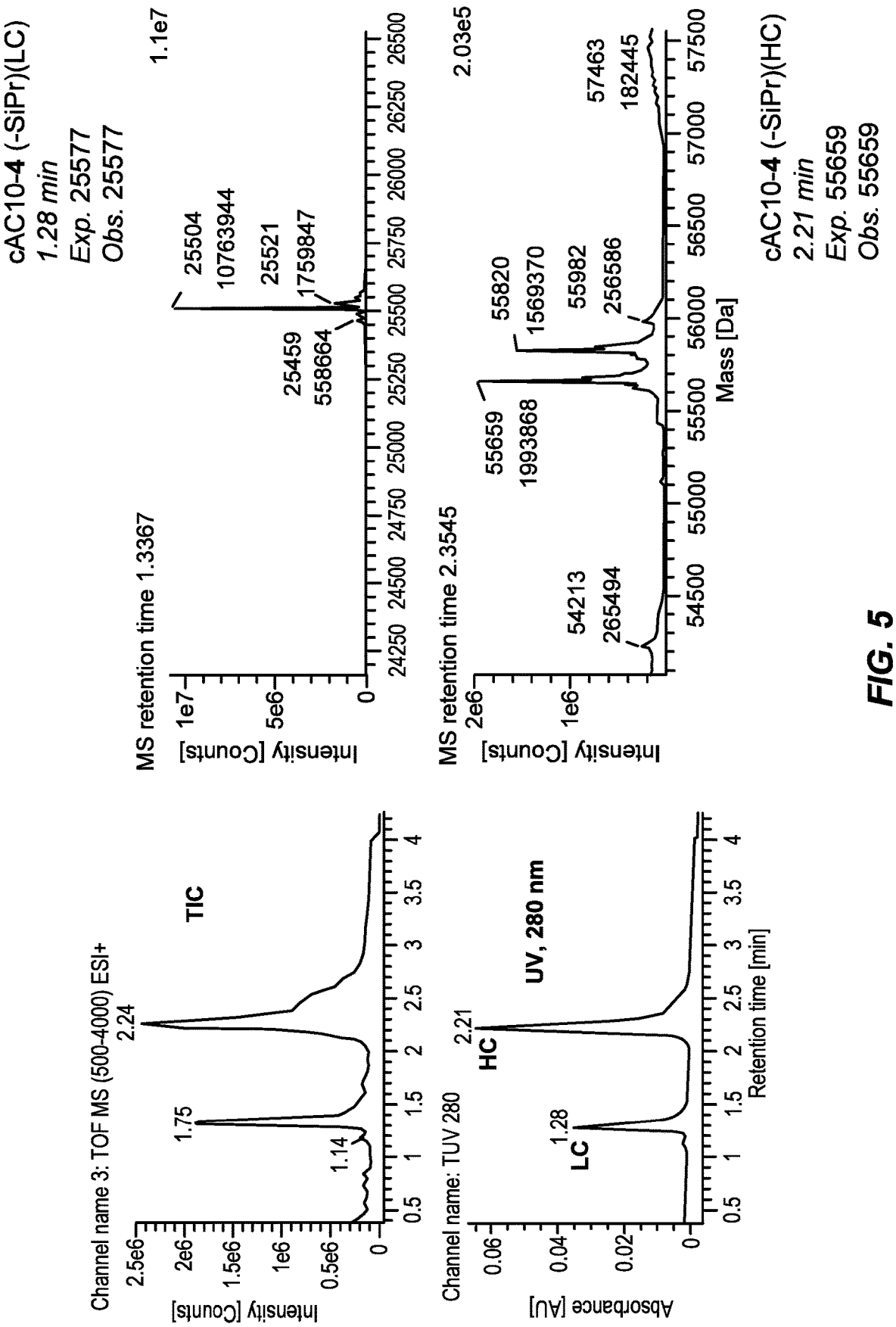
FIG. 5 shows the total ion chromatogram (TIC) and UV chromatogram (280 nm) after reverse-phase separation of light and heavy chain. The deconvoluted mass spectra for light and heavy chain species are shown to the right of the chromatograph, with the expected and observed masses shown. Note that multiple heavy chain mass species are present due to heterogeneity in the N-linked glycan. Only the G0 glycoform mass is noted for the heavy chain. LC=light chain, HC=heavy chain
Figure 6:
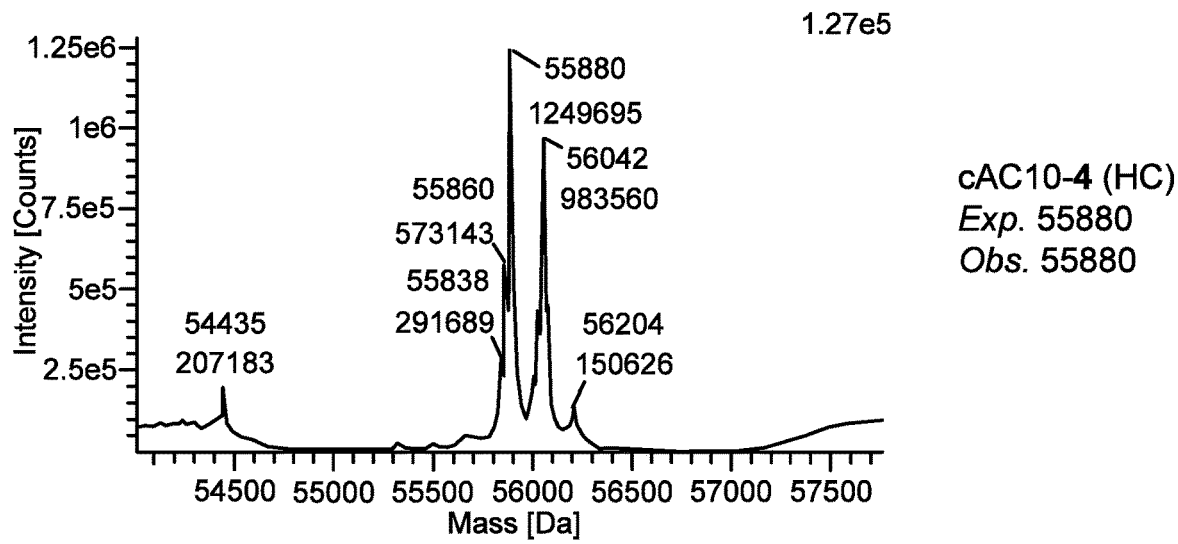
FIG. 6 shows the deconvoluted heavy chain mass of drug-carrier conjugate cAC10-4 before (top) and after —SiPr removal and conjugation of 1 (middle), and -Acm removal and conjugation of 3. The UV chromatograph for each intermediate in shown in FIG. 4. Note that multiple heavy chain mass species are present due to heterogeneity in the N-linked glycan. Only the G0 glycoform mass is noted for the heavy chain.
Figure 6:
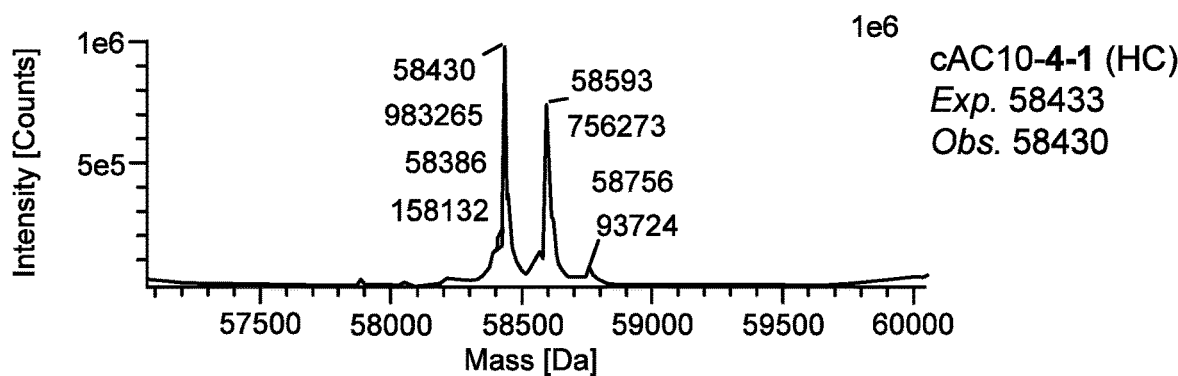
Figure 6:
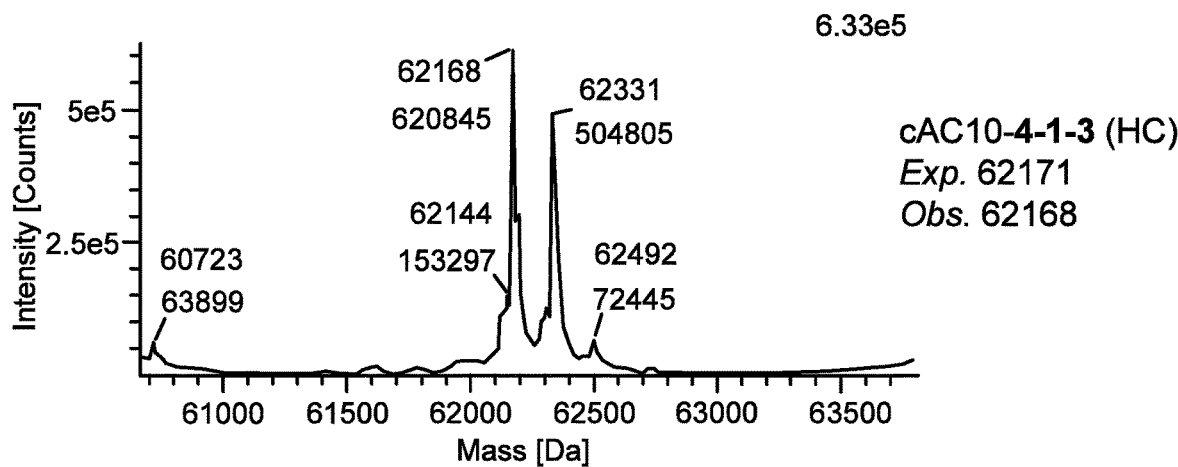
Figure 7:
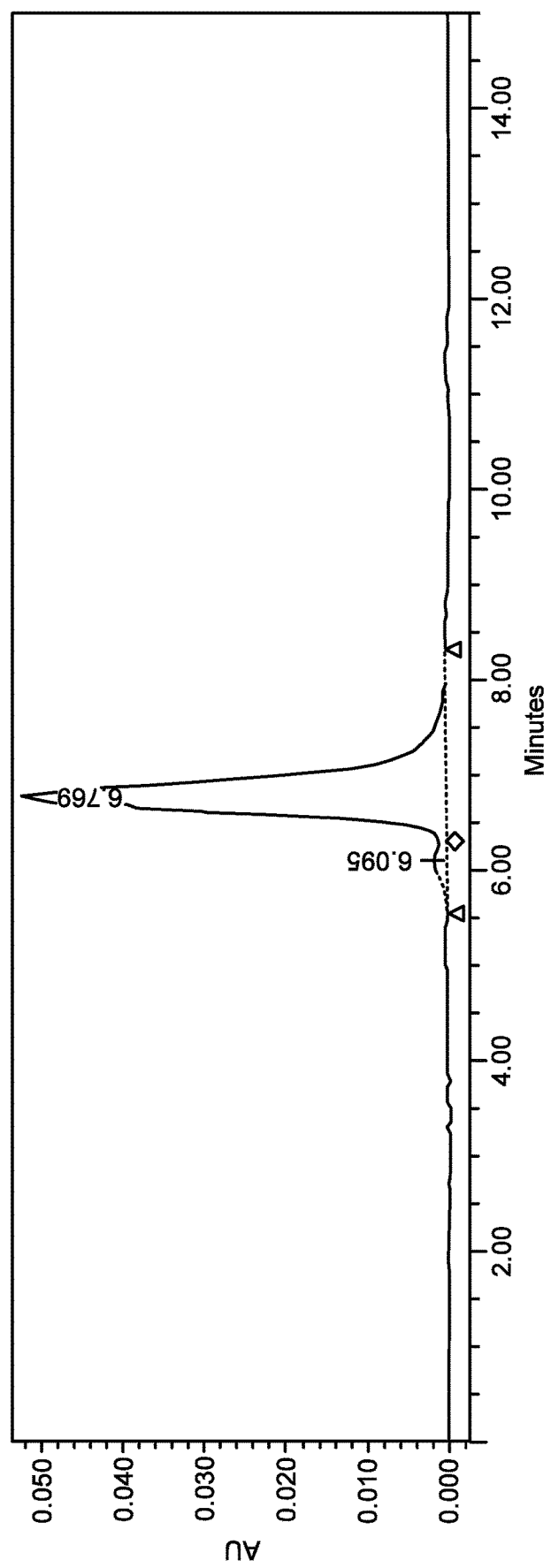
FIG. 7 shows SEC characterization of the MD-ADC cAC10-1-3 prepared using drug carrier 4. The conjugate was 98% monomeric (6.77 min).

Deprotection of Cys(SiPr):

To cAC10-4 (8 carriers/antibody) was added 10-12 equiv. of TCEP. The reaction mixture was incubated at 37° C. for 45 min, at which time reverse-phase LC-MS indicated that reduction was complete (by evaluation of the deconvoluted light and heavy chain masses, see FIG. 2 for an example). Upon completion of the reaction, excess TCEP and liberated isopropyl thiol was removed by 3 rounds of ultrafiltration into PBS-EDTA as described above.

First Conjugation:

To fully reduced cAC10-4 was added 50% molar excess of maleimide drug-linker from a 10 mM DMSO stock. The resulting solution was vortexed and left at room temperature for 15 min. At this time, reverse-phase LC-MS was used to judge reaction progress, and additional drug-linker or NEM was added as needed until all thiols had been alkylated. The conjugate was purified by gel filtration or ultrafiltration according to the procedures described above.

Acm Deprotection:

To a solution containing cAC10-4-drug/NEM was added 50 equiv. of aqueous $Hg(OAc)_2$. The resulting solution was vortexed and left at room temperature for 45 min. To the reaction mixture was added an aqueous slurry of Quadrasil MP resin (0.025 mmol/g thiol capacity, 1 equiv. of resin to 1 equiv. mercury acetate added), and the mixture vortexed vigorously for 15 min. At this time, the mixture was centrifuged at 13,200×g for 2 min and the supernatant removed. The conjugate bearing 8 free thiols was either used without subsequent purification, or purified by three rounds of ultrafiltration into PBS-EDTA as described above.

Second Conjugation:

To a solution containing cAC10-4-drug/NEM with 8 free thiols was added 50-100% molar excess of maleimide drug-linker or NEM from a 10 mM DMSO stock. The resulting solution was vortexed and left at room temperature for 15 min. At this time, reverse-phase LC-MS was used to judge reaction progress, and additional drug-linker or NEM was added as needed until all thiols had been alkylated. The conjugate was purified by gel filtration or ultrafiltration according to the procedures described above.

The average drugs per antibody during each step of the conjugation process was within 2.5% of complete drug loading (8 drugs/mAb), as determined by reverse-phase HPLC.

The conjugation and deprotection steps and analytical characterization described herein are summarized in FIGS. 4-7.

Analytical Characterization of Conjugates and Conjugate Intermediates:

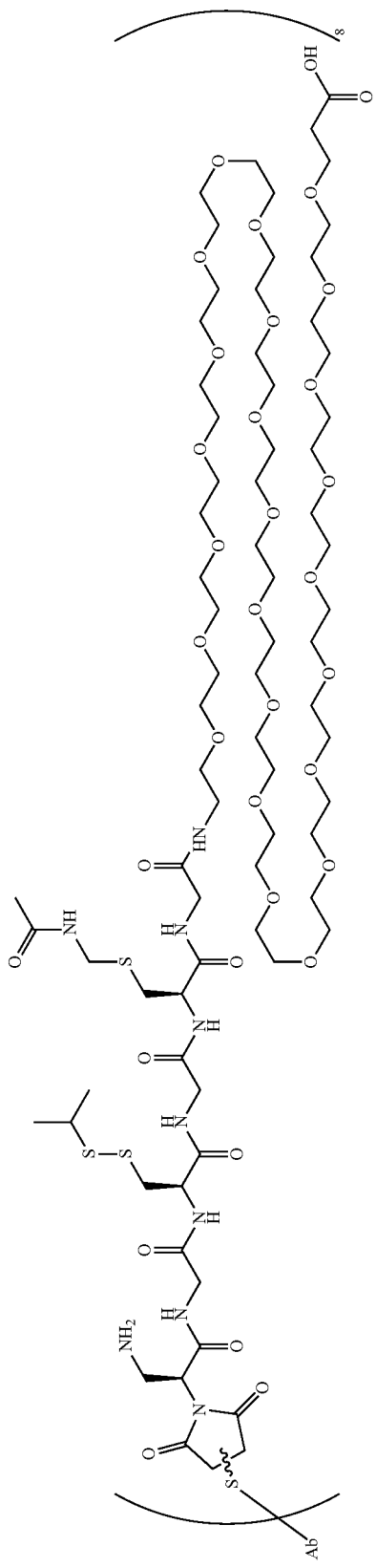
cAC10-4
Light chain: $t_R$ = 1.41 min; expected mass: 25577, observed 25577
Heavy chain: $t_R$ = 2.34 min; expected mass: 55880 (heavy chain + 3 carriers), observed 55880
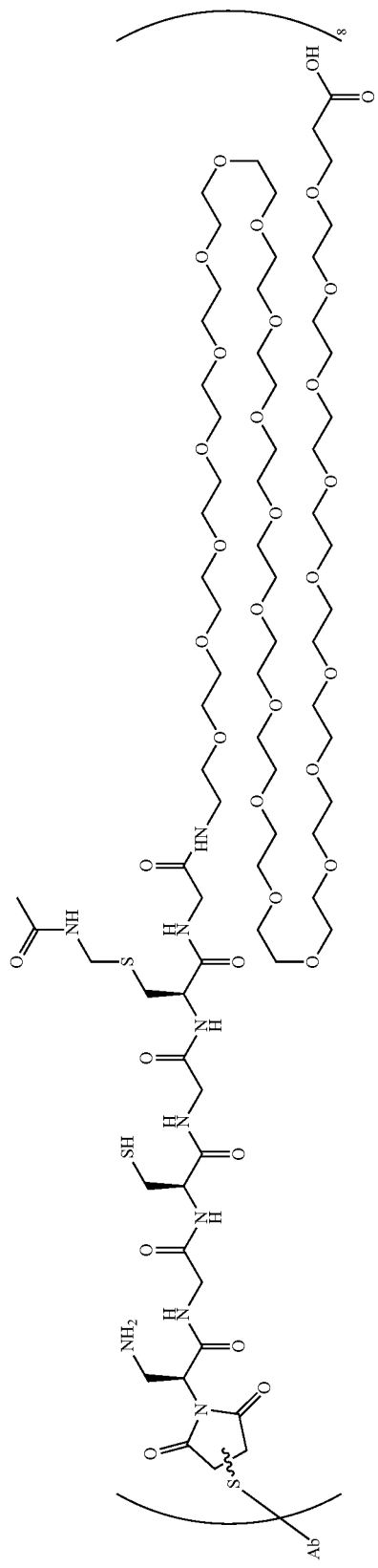
cAC10-4(-SiPr)
Light chain: $t_R$ = 1.38 min; expected mass: 25503, observed 25504
Heavy chain: $t_R$ = 2.34 min; expected mass: 55658 (heavy chain - 3 -SiPr), observed 55659

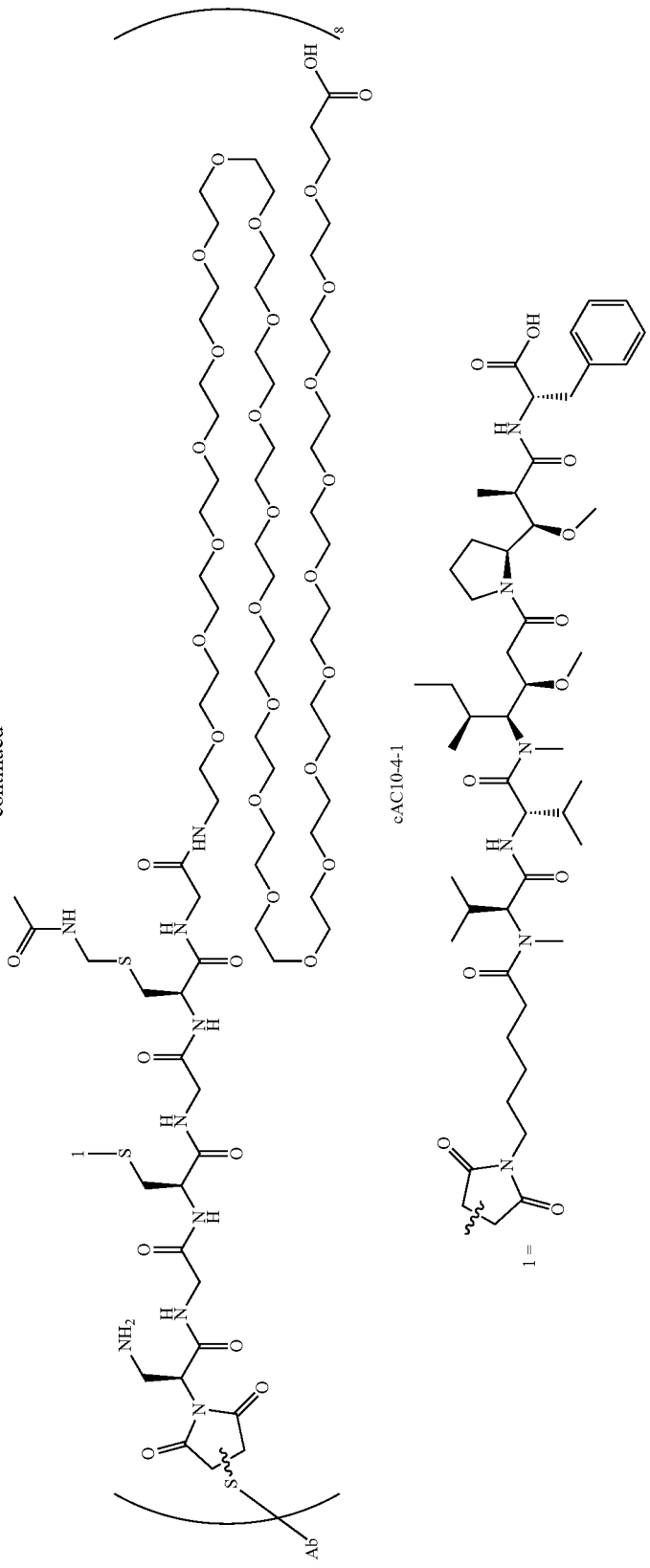

-continued
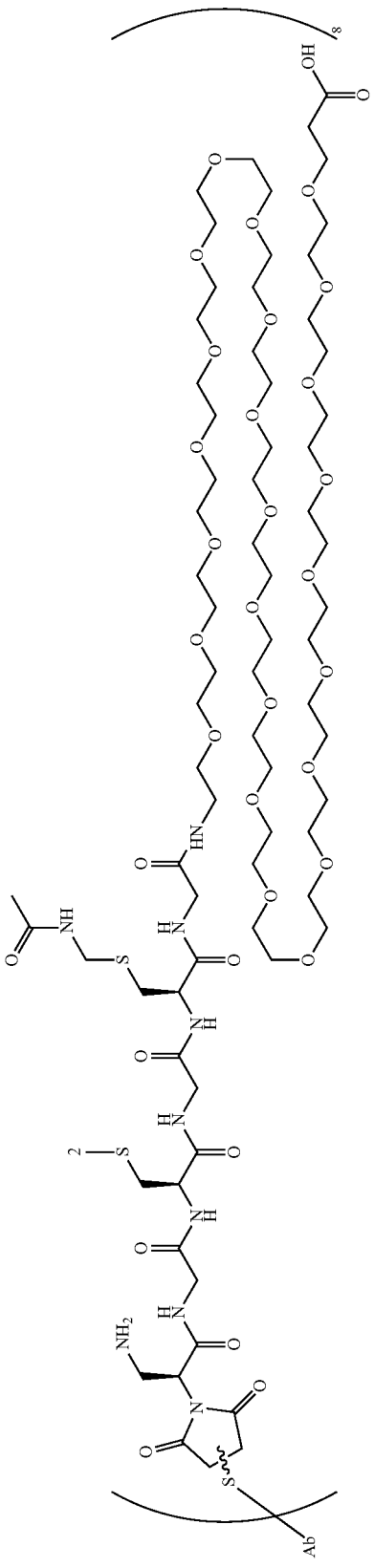
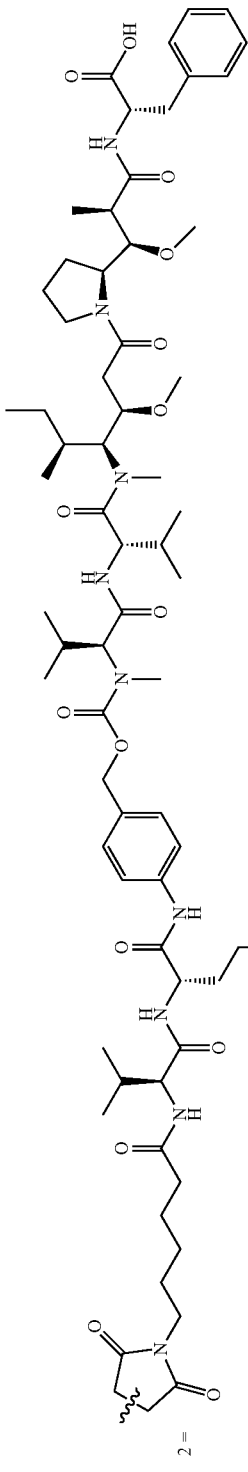
cAC10-4-2
Light chain: $t_R$ = 1.49 min; expected mass: 26834, observed 26382
Heavy chain: $t_R$ = 2.09 min; expected mass: 59651 (heavy chain + 3 drugs), observed 59646

-continued
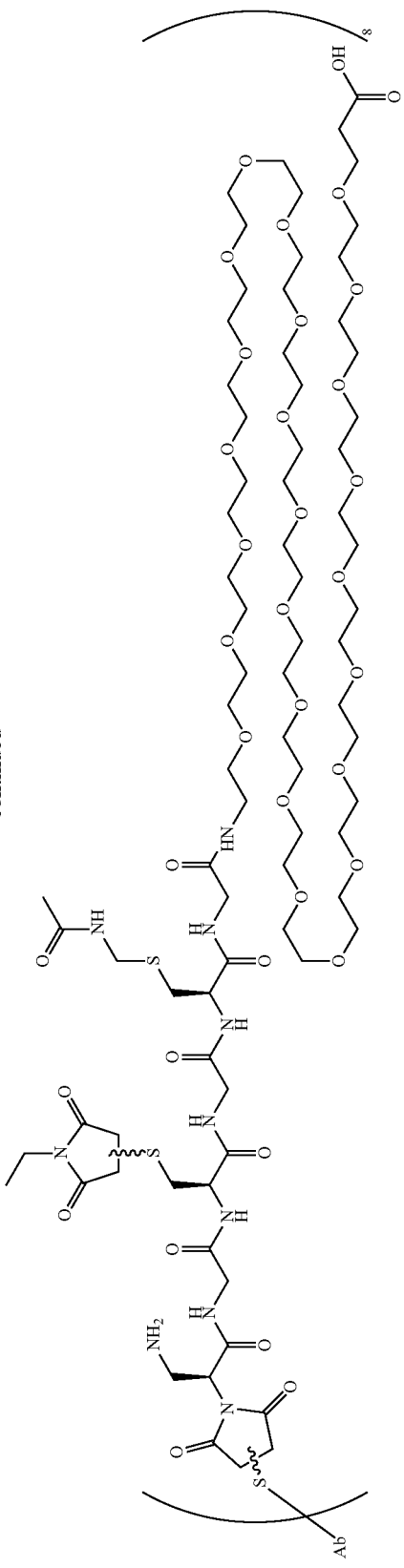
cAC10-4-NEM
Light chain: $t_R$ = 0.98 min; expected mass: 25629, observed 25627
Heavy chain: $t_R$ = 1.38 min; expected mass: 56034 (heavy chain + 3 NEM), observed 56031
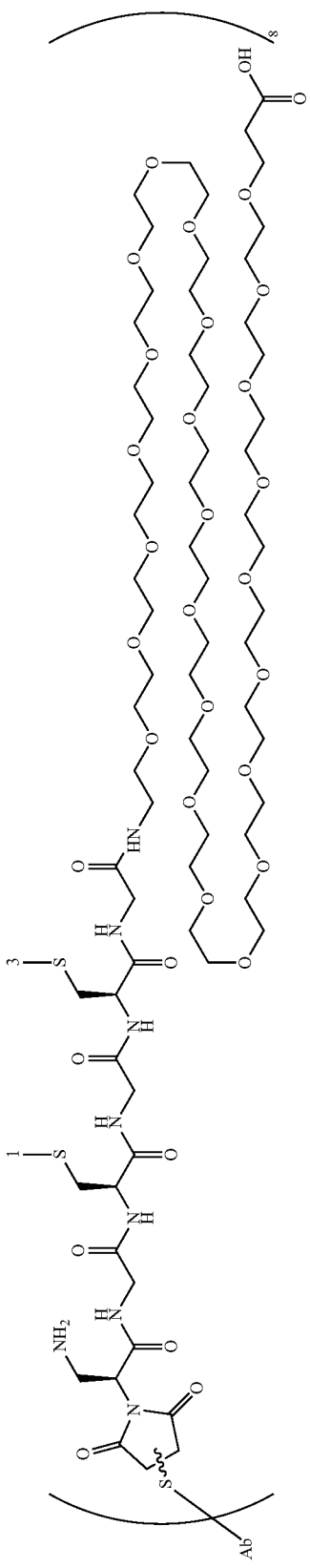
cAC10-4-1-3

-continued
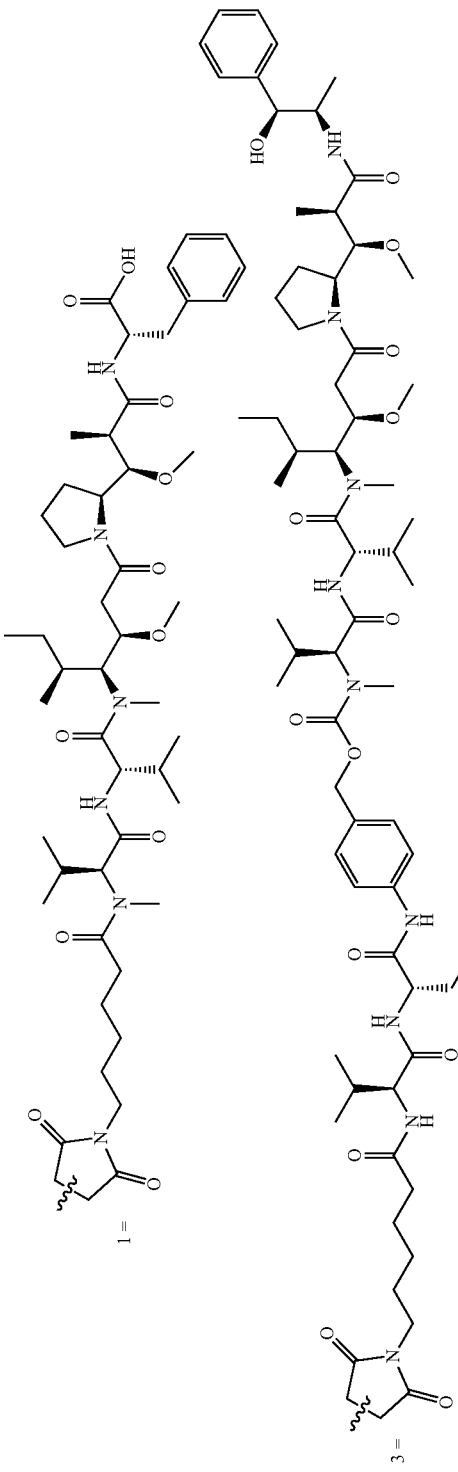
Light chain: $t_R$ = 1.83 min; expected mass: 26675, observed 27673
Heavy chain: $t_R$ = 2.56 min; expected mass: 62172 (heavy chain + 3 drugs), observed 62170
SEC $t_R$ = 6.77 min, 98.0% monomeric

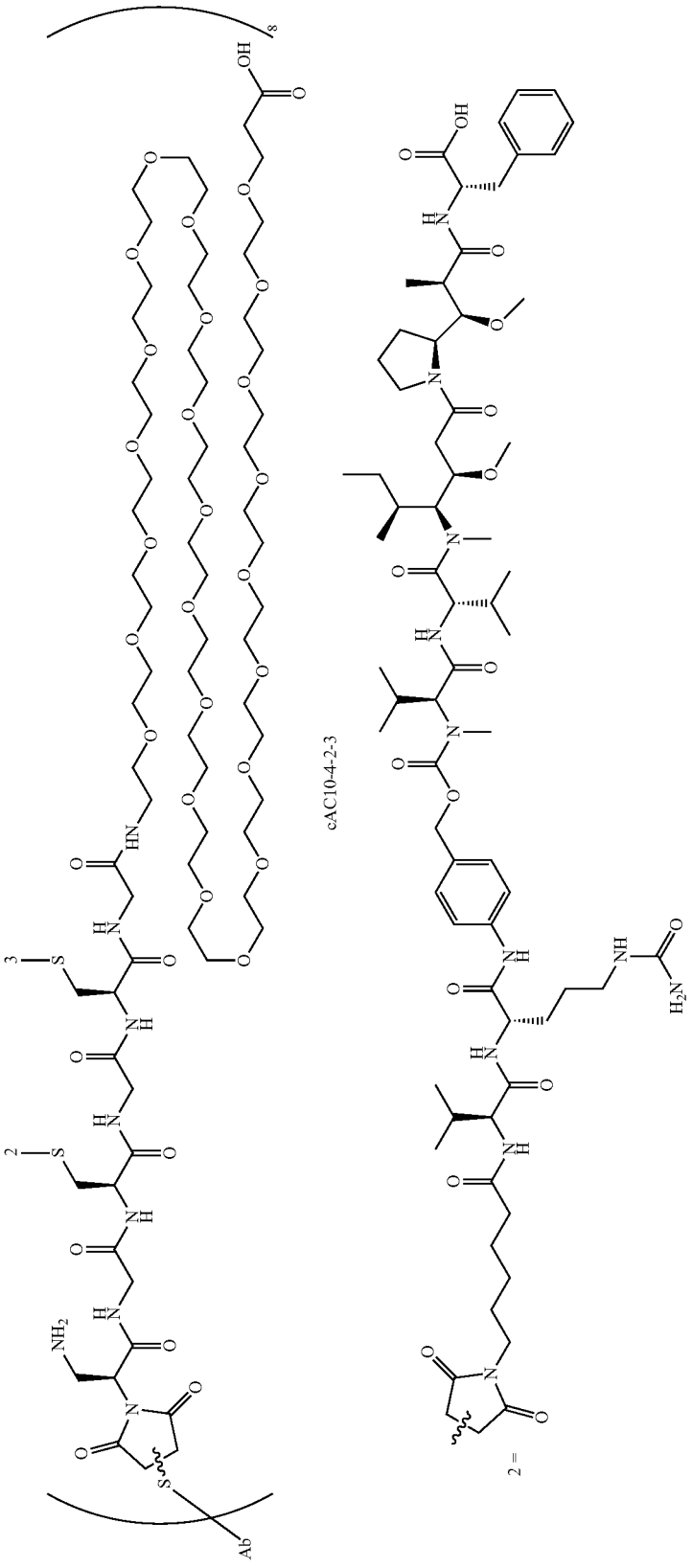

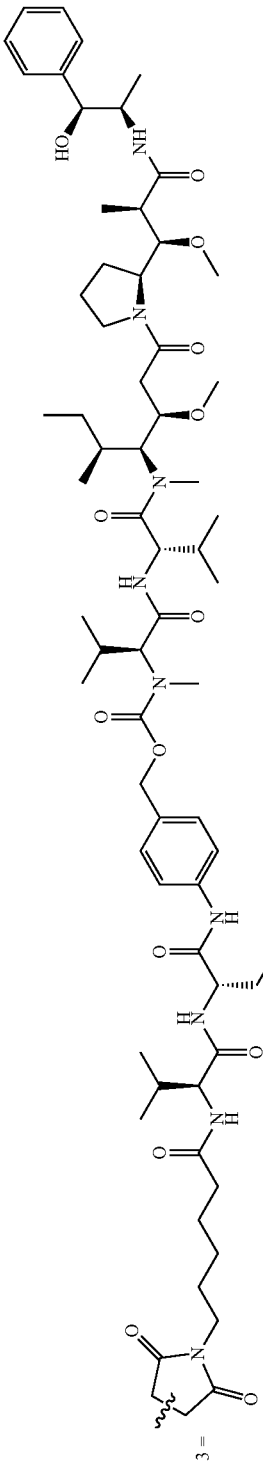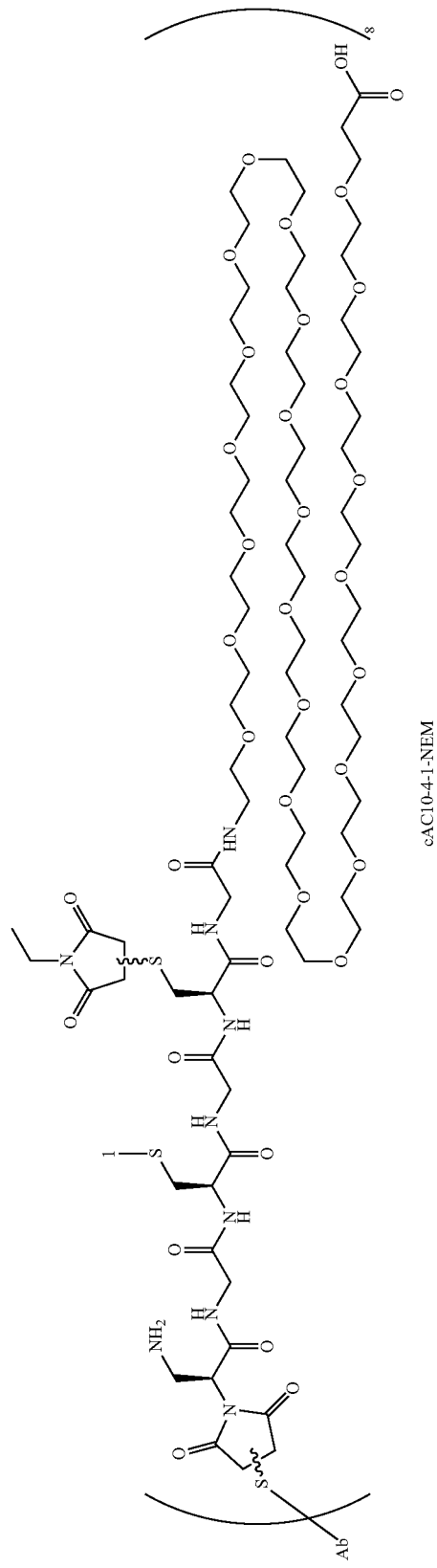

-continued
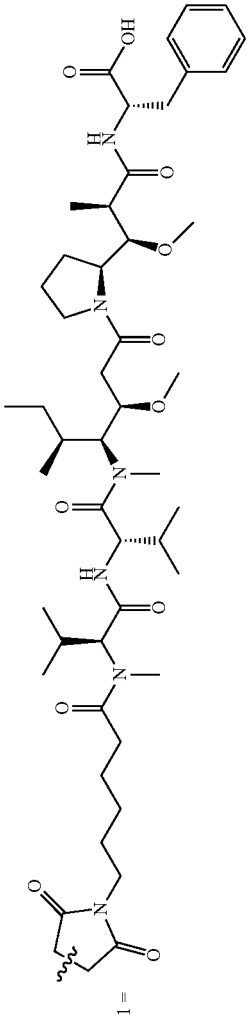
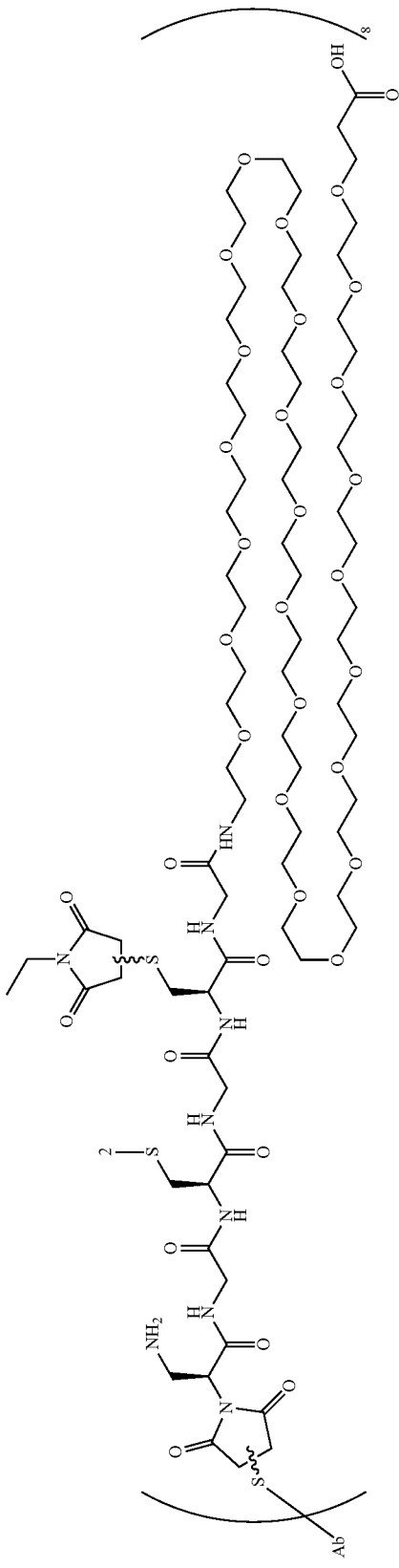
Light chain: $t_R$ = 1.33 min; expected mass: 26483, observed 26482
Heavy chain: $t_R$ = 1.90 min; expected mass: 58596 (heavy chain + 3 NEM), observed 58598
SEC $t_R$ = 6.91 min, 97.5% monomeric
cAC10-4-2-NEM -continued
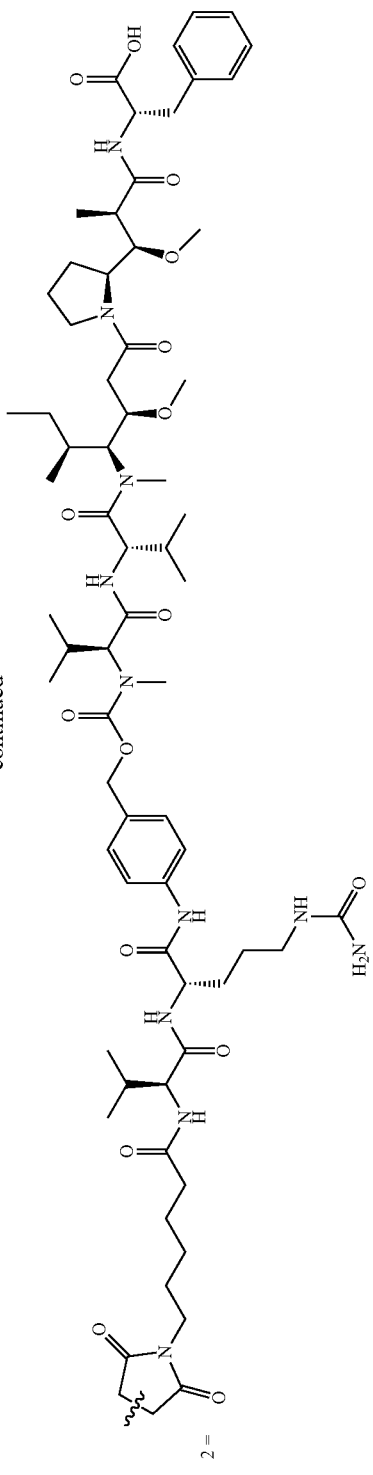
Light chain: $t_R$ = 1.53 min; expected mass: 26888, observed 26889
Heavy chain: $t_R$ = 2.14 min; expected mass: 59813 (heavy chain +3 NEM), observed 59815
SEC $t_R$ = 6.74 min, 97.4% monomeric
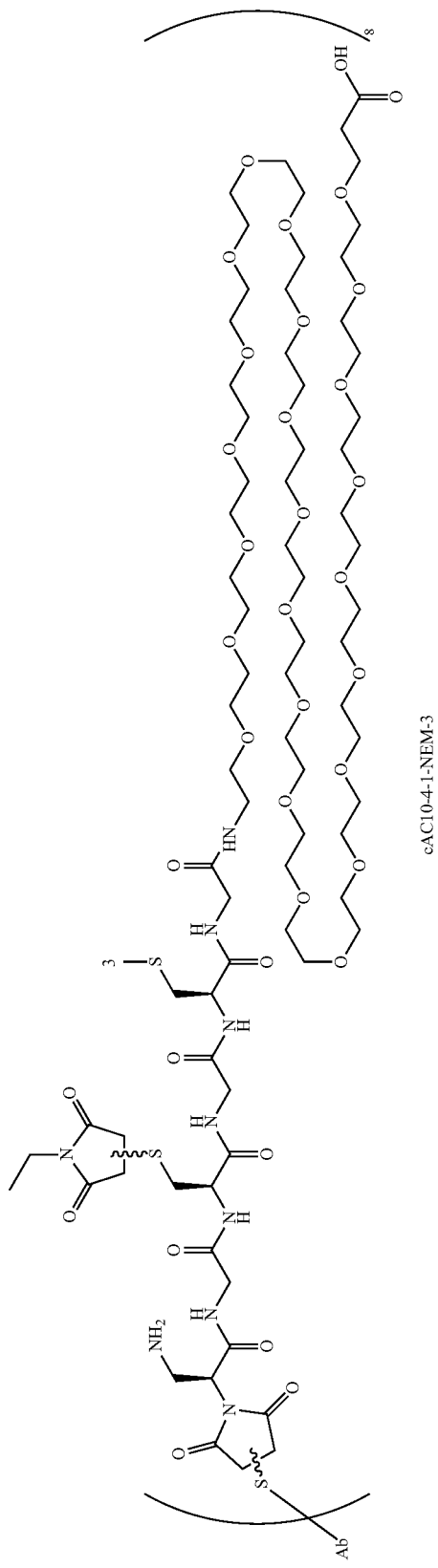
cAC10-4-1-NEM-3

-continued
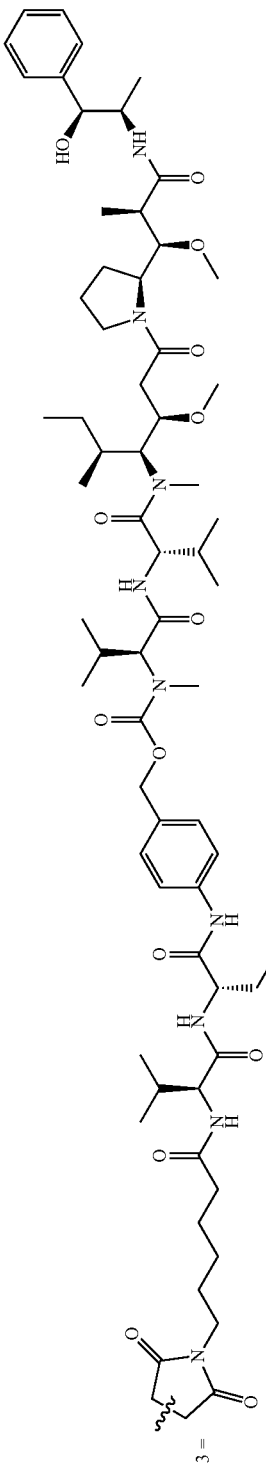
3 =
Light chain: $t_R$ = 1.55 min; expected mass: 26875, observed 26875
Heavy chain: $t_R$ = 2.19 min; expected mass: 59772 (heavy chain + 3 drugs), observed 59772
SEC $t_R$ = 7.03 min; 97.8% monomeric

Example 4: Cell Binding Analysis

Figure 8:
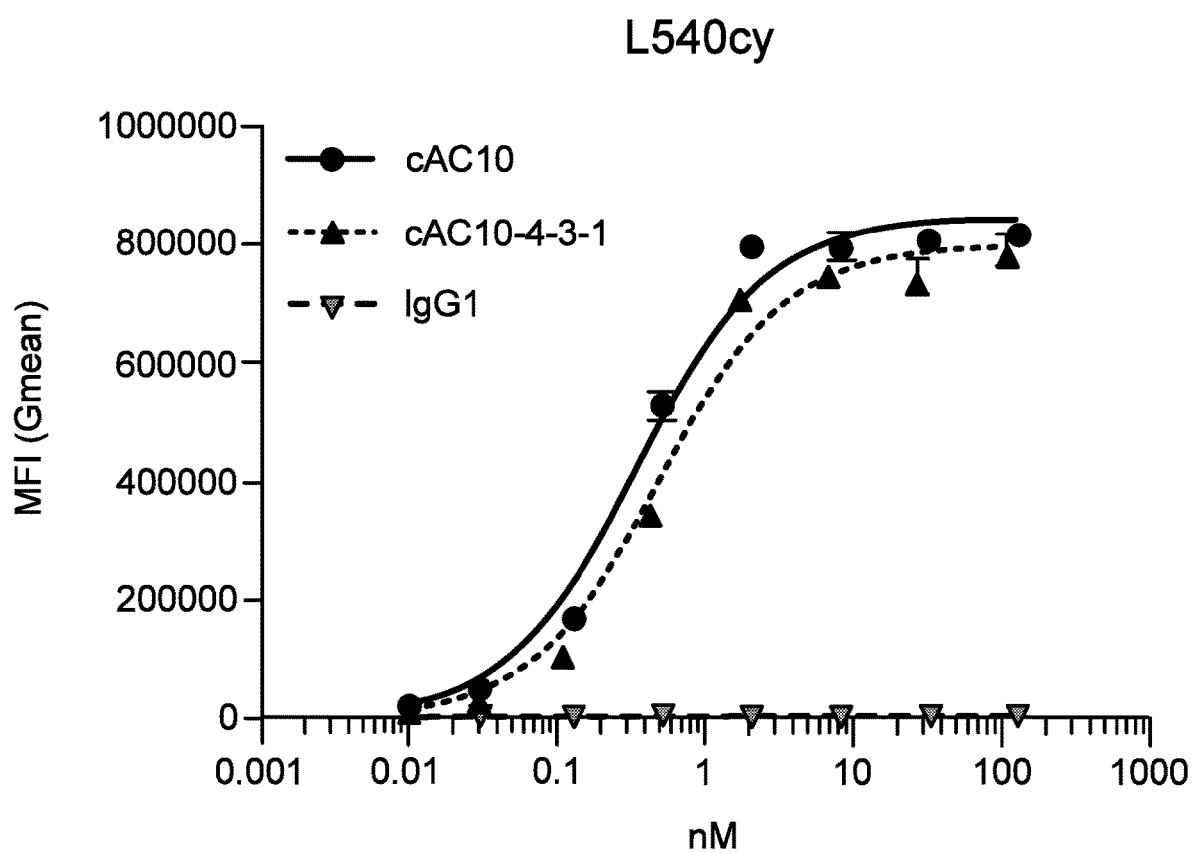
FIG. 8 shows saturation binding of cAC10 antibody, cAC10-4-(3-1) ADC, or non-binding IgG$_1$ isotype control on CD30(+) L540cy cells. The calculated $K_D$ values for cAC10 naked antibody and cAC10-4-(3-1) were 0.35 nM and 0.50 nM, respectively. Neither cAC10 or cAC10-4-(3-1) bound to CD30(-) U-266 cells (not shown).

Binding of antibody or ADC to cell-surface CD30 was assessed by flow cytometry on CD30(+) L540cy Hodgkin lymphoma cells. Cells ($2 \times 10^5$) were combined with 4-fold serial dilutions of each antibody treatment in flow buffer (PBS, 2% fetal bovine serum, 0.2% $NaN_3$) in a total volume of 100 µL. The cells were incubated on ice for 30 min, and then washed twice with ice-cold flow buffer. At this time a FITC-labeled goat anti-human Fc secondary antibody (109-095-098, Jackson ImmunoResearch) was added at the recommended dilution in a total volume of 100 µL flow buffer. The cells were incubated on ice for 30 min, and then washed twice with ice-cold flow buffer. Labeled cells were examined by flow cytometry on an Attune NxT flow cytometer (Thermo Fisher Scientific). Data was analyzed using FlowJo software and plotted using GraphPad Prism 6. Binding constants were determined by nonlinear regression using a one site binding model. Results are shown in FIG. 8.

Example 5: In Vitro Cytotoxicity Experiments

Figure 9:
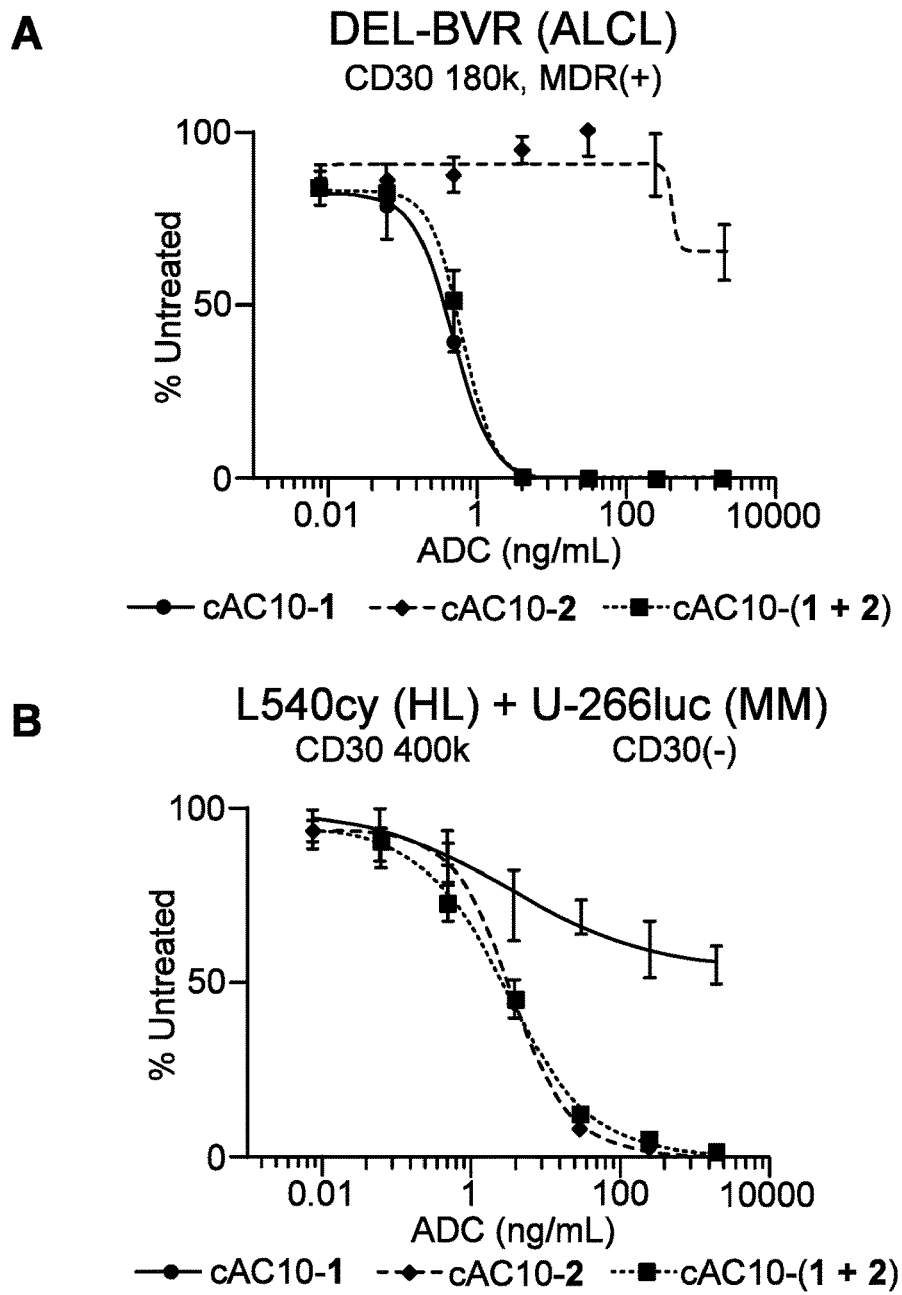
FIGS. 9A and 9B show in vitro activity of cAC10 ADCs against a panel of cell lines. All three ADCs utilize the multiplexing drug carrier 4. For single drug loaded ADCs, the second Cys residue was capped with 8 copies of N-ethyl maleimide. Activity is reported as $IC_{50}$ in ng/mL of ADC. In panel A, cells were treated with ADCs for 96 hours, and cell viability was determined using Cell TiterGlo (Promega), while in panel B cell viability was determined using the Bright-Glo luciferase assay system (Promega). HL=Hodgkin lymphoma, ALCL=anaplastic large cell lymphoma.
Figure 10:
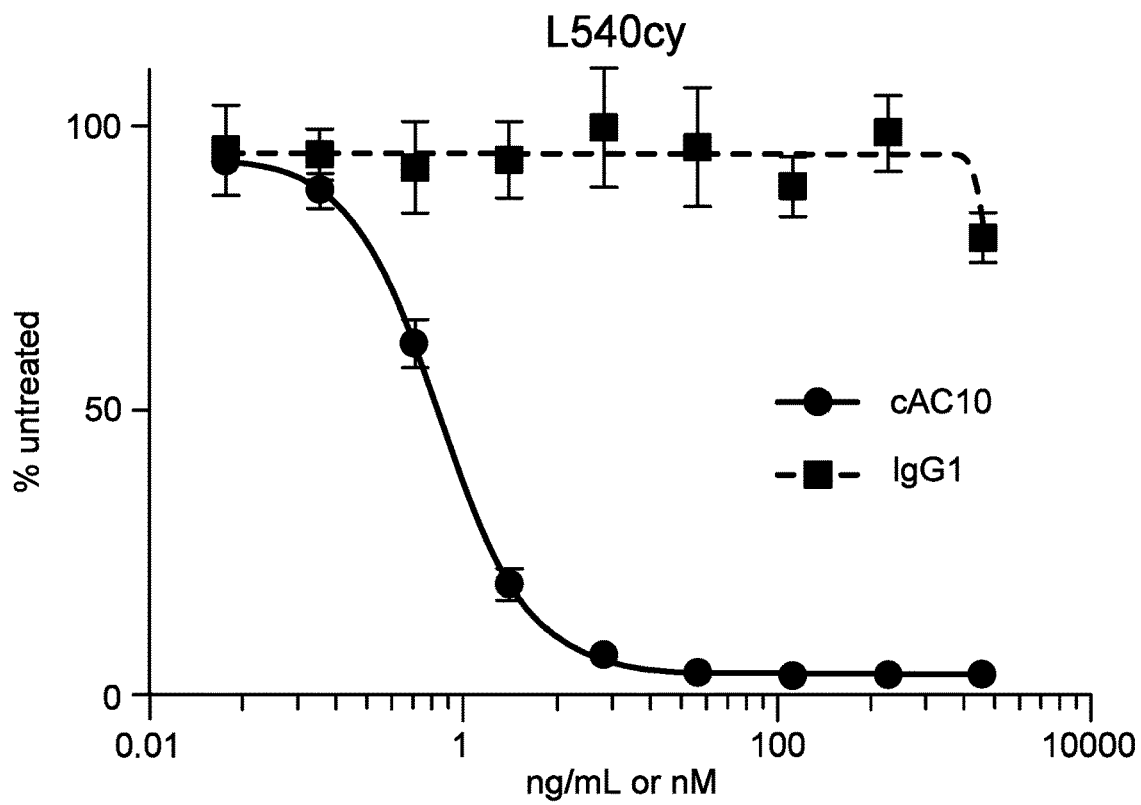
FIG. 10 shows an isotype control ADC (IgG1-4-(1-3)) was inactive on CD30(+) L540cy cells whereas cAC10-4-(1-3) was highly active.

In vitro potency was assessed on multiple cancer cell lines: L540cy (Hodgkin lymphoma) and DEL, and DEL-BVR[6] (anaplastic large cell lymphomas), U-266 (multiple myeloma). L540cy and DEL were obtained from DSMZ and U-266 was obtained from ATCC. Authenticity of cell lines was confirmed using the Cell Check 16 panel (IDEXX Bioresearch). U-266 cells stably expressing firefly luciferase were generated using in vivo ready lentiviral particles from GenTarget, Inc. (San Diego, Calif.). U-266 cells were grown to $1 \times 10^6$ cells/mL (>90% viable) and transduced with lentiviral particles for 72 hours in RPMI 1640 media+10% FBS. Cells were placed under selection in neomycin and stable clones were produced by dilution cloning into 96 well plates. A stable U-266luc cell line was selected using the Bright-Glo Luciferase Assay System (Promega) using an EnVision Multilabel Plate Reader (Perkin Elmer). For all cytotoxicity experiments, cells were cultured in log-phase growth, then seeded for 24 hours in 96-well plates containing 150 µL RPMI-1640 supplemented with 10-20% FBS. Serial dilutions of ADCs in cell culture media were prepared at 4× working concentrations, and 50 µL of each dilution was added to the 96-well plates. Following addition of ADCs, cells were incubated for 4 days at 37° C. After 96 hours, growth inhibition was assessed by CellTiter-Glo (Promega) and luminescence was measured on an Envision plate reader. The $IC_{50}$ value determined in triplicate is defined here as the concentration that results in half maximal growth inhibition over the course of the titration curve. For the in vitro bystander assay, L540cy and luciferase(+) U-266 cells (U-266luc) were seeded in 96-well plates at a 1:1 ratio. Test article dilutions were added to the cells as outlined above. After 96 hours, growth inhibition of the U-266luc cells was assessed by BrightGlo and luminescence was measured on an Envision plate reader. Results are shown in FIGS. 9 and 10.

Example 6: Comparison of Co-Administration of 2 ADCs Versus Co-Conjugation of 2 Drugs on 1 ADC ADCs were added to cells at the same total antibody concentration and cytotoxicity was measured as outlined above. Competition for receptor binding leads to decreased activity (on an antibody basis) for co-administration. On cell lines with low receptor copy number, the effect can be more pronounced.

| Cell line | | Antigen # | Co-Conjugate $IC_{50}$ (ng/mL) | Co-Administration $IC_{50}$ (ng/mL) | Fold difference |
|---|---|---|---|---|---|
| CD30 (cAC10) | L540cy | 400,000 | 0.3 | 1.3 | 4 |
| | Karpas 299 | 320,000 | 0.5 | 1.5 | 3 |
| CD19 (hBU12) | SU-DHL-16 | 10,000 | 0.2 | 0.5 | 2.5 |
| | Granta-519 | 10,000 | 3 | 124.5 | 41.5 |

Example 7: In Vivo Xenograft Experiments

Figure 11:
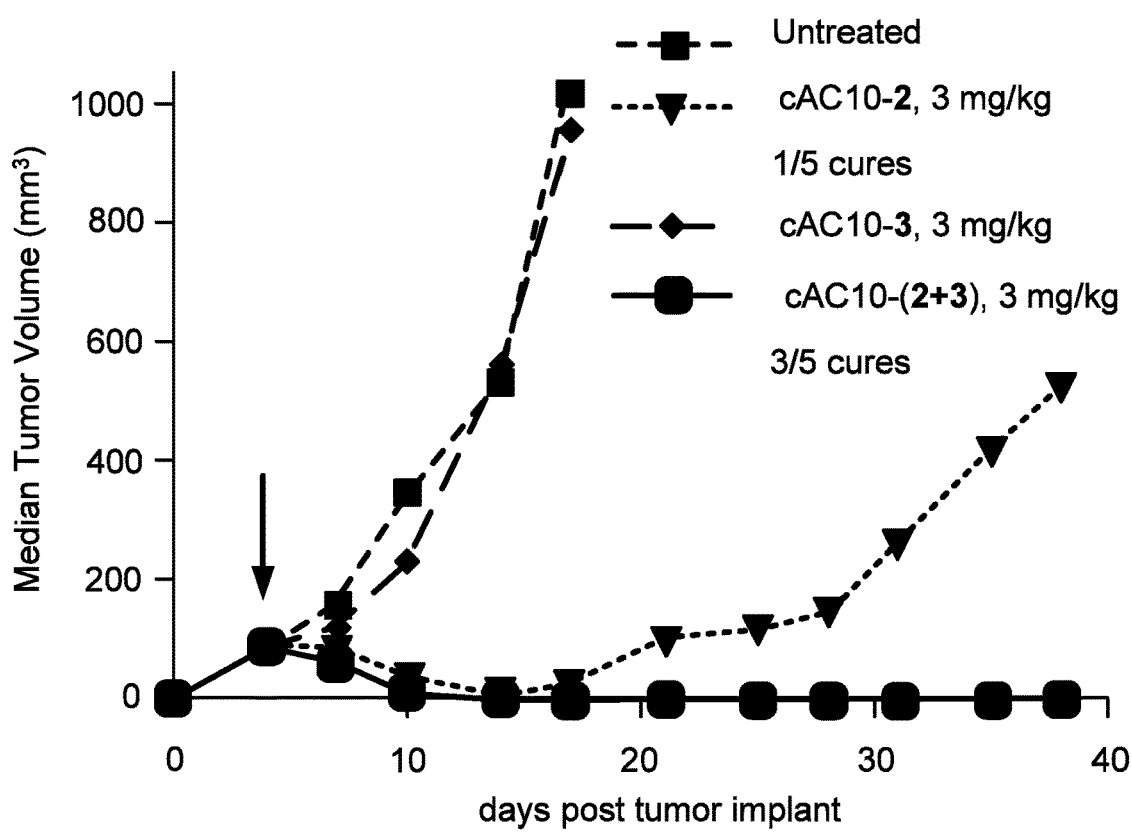
FIG. 11 shows Dual-drug ADC activity on MDR(+) DEL-BVR xenograft model in vivo. Each MD-ADC was prepared using drug carrier 4. For single-drug conjugates, the second Cys residue was capped with 8 copies of N-ethyl maleimide.
Figure 12:
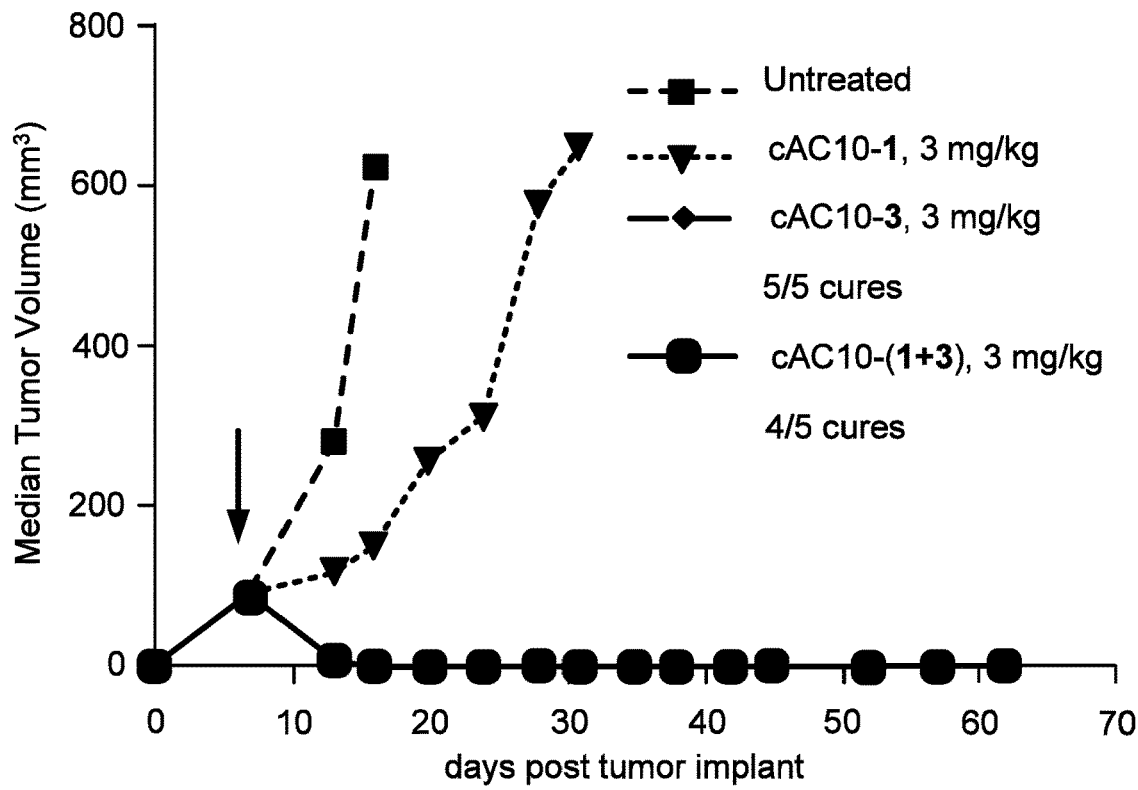
FIG. 12 shows MD-ADC activity on an in vivo xenograft model with heterogeneous CD30 expression. The xenograft model consisted of a 1:1 mixture of Karpas 299 (CD30+) and Karpas 35R (CD30-) cells. Each MD-ADC was prepared using drug carrier 4. For single-drug conjugates, the second Cys residue was capped with 8 copies of N-ethyl maleimide.

All experiments were conducted in concordance with the Institutional Animal Care and Use Committee in a facility fully accredited by the Association and Accreditation of Laboratory Animal Care. Therapy experiments were conducted using DEL-BVR, Karpas 299, or Karpas-35R cells that were implanted subcutaneously into severe combined immunodeficiency (SCID) mice (Harlan, Indianapolis, Ind.). The admixed tumor model was implanted with a mixture containing 2.5 million Karpas 299 and 2.5 Karpas-35R cells.[7] Upon tumor engraftment, mice were randomized to study groups when the average tumor volume reached approximately 100 $mm^3$. The ADCs were dosed once by intraperitoneal injection. Animals were euthanized when tumor volumes reached 1000 $mm^3$. Tumor volume was calculated with the formula (volume=½×length×width×width). Mice showing durable regressions were terminated around day 40-65 after implant. Results are shown in FIGS. 11 and 12.

Example 8: Dual ADCs Compared to 8- and/or 16-Load Single Drug ADCs

ADCs having either mcMMAF (Comp. Aa) or mc-vc-MMAE (Comp. Ab) were compared to a dual-auristatin ADC bearing Comp. Aa/Comp. Ab at matched drug loads of 16 drugs per antibody. On most cell lines and with different antibodies, the co-conjugate (having Comp. Aa and Comp Ab) had equivalent ADC activity compared to hBU12-Linking Assembly Unit Aa (8)-Comp. Aa (16) (a single-drug 16-load ADC with only Comp. Aa as the drug unit). This was despite the hBU12-Linking Assembly Unit Aa (8)-Comp. Ab (16) ADC (a single-drug 16-load ADC with only Comp. Ab as the drug unit) having significantly lower activity. A dual-auristatin ADC targeting LIV-1 with the hLIV22 antibody had significantly higher in vitro activity compared to either single-drug 16-load ADC. This data demonstrates that the co-conjugated auristatin ADCs demonstrate improved cytotoxic activity independent of antibody or cell line.

In addition to showing that co-conjugated ADCs with auristatin drugs are broadly active, the tables below also show that co-conjugated ADCs delivering other payloads can have high activity. For example, camptothectin, dolastatin, and vinblastine can be incorporated into co-conjugated ADCs to provide enhanced activity.

Linking Assembly Unit Aa, referred to above as drug carrier 4:

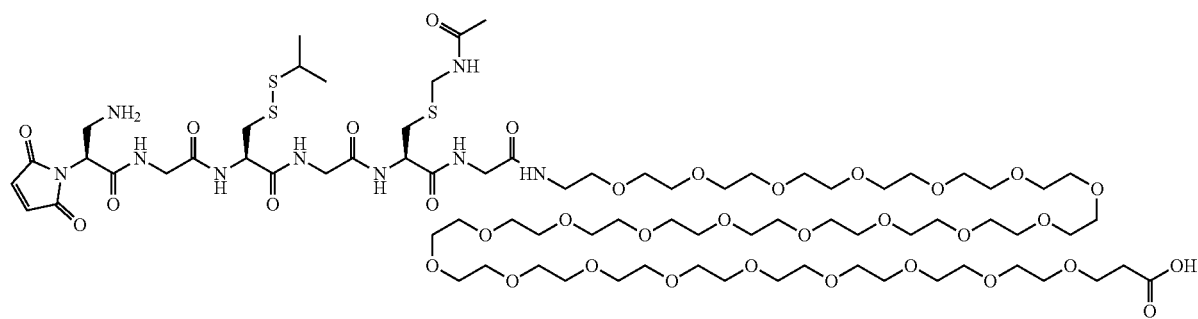 [SMILES: CC(=O)NCSC[C@H](NC(=O)CNC(=O)[C@H](CSSC(C)C)NC(=O)CNC(=O)[C@H](CN)N1C(=O)C=CC1=O)C(=O)NCC(=O)NCCOCCOCCOCCOCCOCCOCCOCCOCCOCCOCCOCCOCCOCCOCCOCCOCCOCCOCCOCCOCCOCCOCCOCCOCCC(=O)O]

Linking Assembly Unit Aa comprises MDPr, PEG24, 1 SiPr, and 1 Acm protected Cys residue.
Protecting groups (—S-iPr and —CH$_2$NH—C(=O)CH$_3$) are removed individually and desired drug groups are attached in the above shown Linking Assembly Unit.

Targeting CD19:

| | hBU12- Linking Assembly Unit Aa-conjugates (IC$_{50}$ in ng/mL) | | | | |
|---|---|---|---|---|---|
| Cell line | Comp. Ab (8) | Comp. Aa (8) | Comp. Ab (8) Comp. Aa (8) | Comp. Ab (16) | Comp. Aa (16) |
| Raji | 11.3 | 8.8 | 1.6 | 6.9 | 2.1 |
| WSU-DLCL2 | 72.0 | 13.3 | 1.3 | 8.6 | 1.5 |

Targeting β6 Integrin:

| | h2A2- Linking Assembly Unit Aa - conjugates (IC$_{50}$ in ng/mL) | | | | |
|---|---|---|---|---|---|
| Cell line | Comp. Ab (8) | Comp. Aa (8) | Comp. Ab (8) Comp. Aa (8) | Comp. Ab (16) | Comp. Aa (16) |
| BxPC3 | 21.8 | 24.8 | 6.6 | 6.9 | 10.8 |
| SW780 | 51.5 | 3.1 | 1.8 | 5.5 | 1.7 |

Targeting Hepatocarcinoma:

| | h25G5- Linking Assembly Unit Aa - conjugates (IC$_{50}$ in ng/mL) | | | | |
|---|---|---|---|---|---|
| Cell line | Comp. Ab (8) | Comp. Aa (8) | Comp. Ab (8) Comp. Aa (8) | Comp. Ab (16) | Comp. Aa (16) |
| JHH-7 | >2000 | 45.0 | 16.7 | 125.9 | 13.7 |
| Hep3B | 45.1 | 36.4 | 8.0 | 40.4 | 9.4 |

Targeting LIV-1:

| | hLIV22- Linking Assembly Unit Aa - conjugates (IC$_{50}$ in ng/mL) | | | | |
|---|---|---|---|---|---|
| Cell line | Comp. Ac (8) | Comp. Aa (8) | Comp. Ac (8) Comp. Aa (8) | Comp. Ac (16) | Comp. Aa (16) |
| SK-MEL-5 | 173.5 | 21.6 | 0.6 | 2.8 | 5.5 |

Comp. Ac (MDPr-vc-PABC-MMAE)

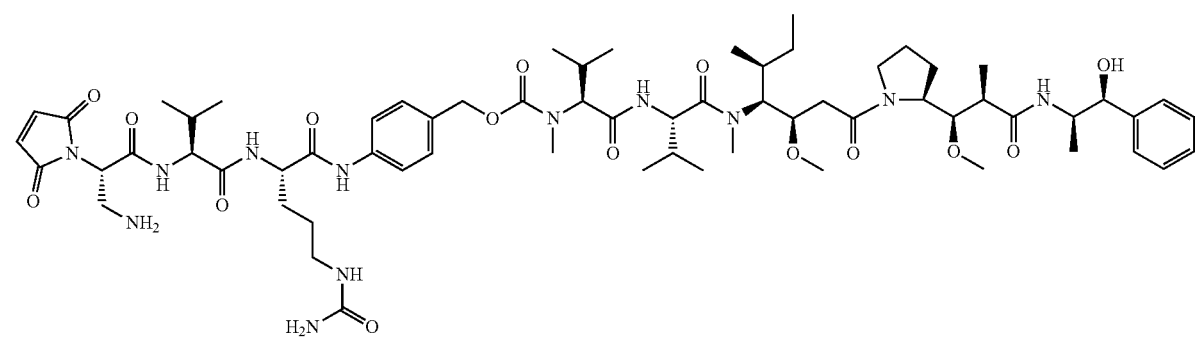 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](CN)N2C(=O)C=CC2=O)C(C)C)cc1)C(C)C]

Camptothecin- and Superdox-Based Co-Conjugates
1. MMAE/Campthothecin Conjugate Targeting CD30
2. Superdox/Camptothecin Conjugate Targeting Antigen 1
Comp. Ae:
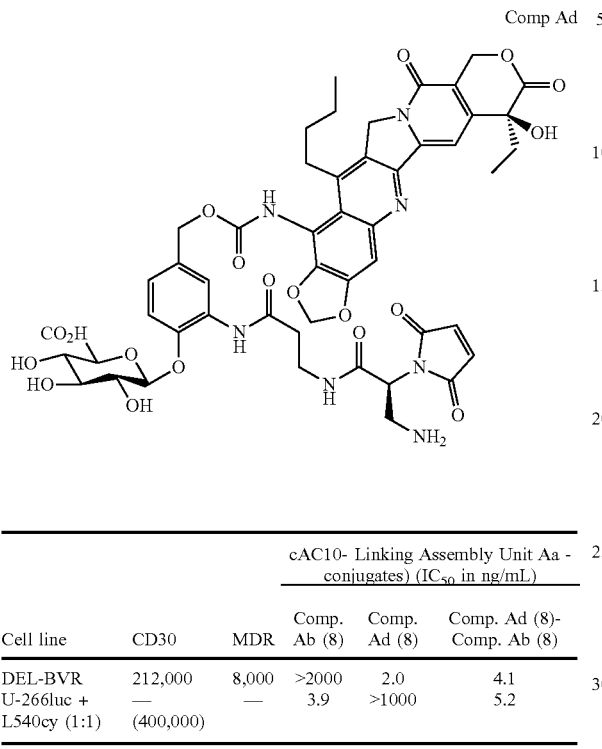
Comp Ad
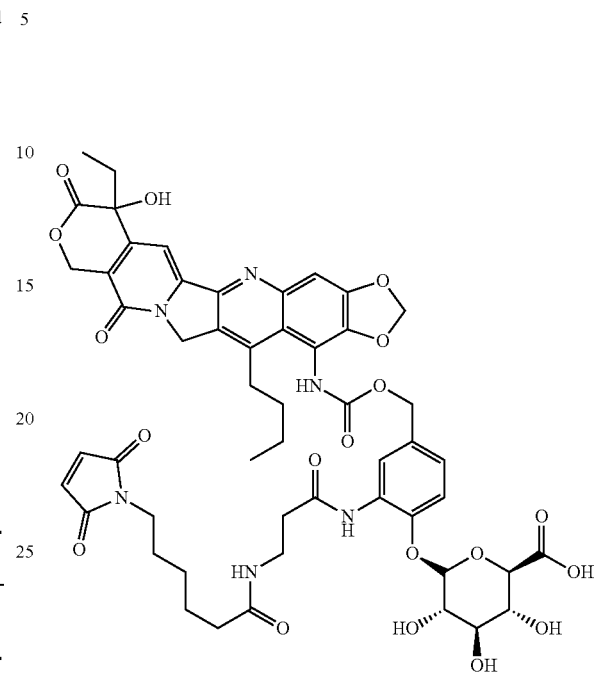
| Cell line | CD30 | MDR | cAC10- Linking Assembly Unit Aa - conjugates) (IC$_{50}$ in ng/mL) | | |
|---|---|---|---|---|---|
| | | | Comp. Ab (8) | Comp. Ad (8) | Comp. Ad (8)-Comp. Ab (8) |
| DEL-BVR | 212,000 | 8,000 | >2000 | 2.0 | 4.1 |
| U-266luc + L540cy (1:1) | — (400,000) | — | 3.9 | >1000 | 5.2 |
Comp. Af:
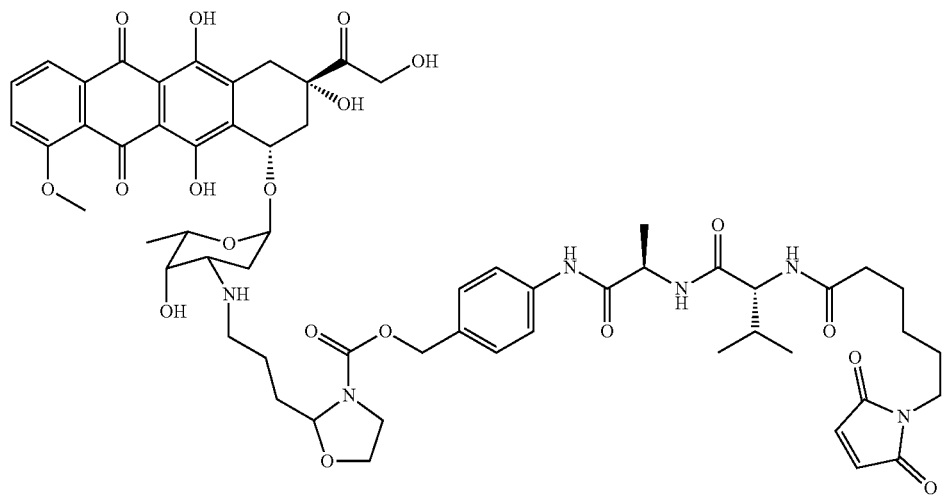 [SMILES: COc1cccc2c1C(=O)c1c(O)c3c(c(O)c1C2=O)C[C@@](O)(C(=O)CO)C[C@@H]3OC1CC(NCCCC2OCCN2C(=O)OCc2ccc(NC(=O)[C@@H](C)NC(=O)[C@H](NC(=O)CCCCCN3C(=O)C=CC3=O)C(C)C)cc2)C(O)C(C)O1]

3. Superdox Combined with MMAE:

| | Antibody1-Linking Assembly Unit Aa - conjugates (IC$_{50}$ in ng/mL) | | |
|---|---|---|---|
| Cell line | Comp. Ae (8) | Comp. Af(8) | Comp. Ae (8)-Comp. Af(8) |
| L428 | 649 | 280 | 49 |
| L540cy | 73 | 54 | 20 |
| Raji | 74 | 52 | 11 |

| | Antibody 1-Linking Assembly Unit Aa - conjugates (IC$_{50}$ in ng/mL) | | |
|---|---|---|---|
| Cell line | MMAE (8) | Comp. Af (8) | MMAE (8)-Comp. Af(8) |
| L428 | 456 | 280 | 62 |
| HuH-7 | 131 | 173 | 28 |

Dolastatin 10 Combined with Auristatins
Comp. Ag:

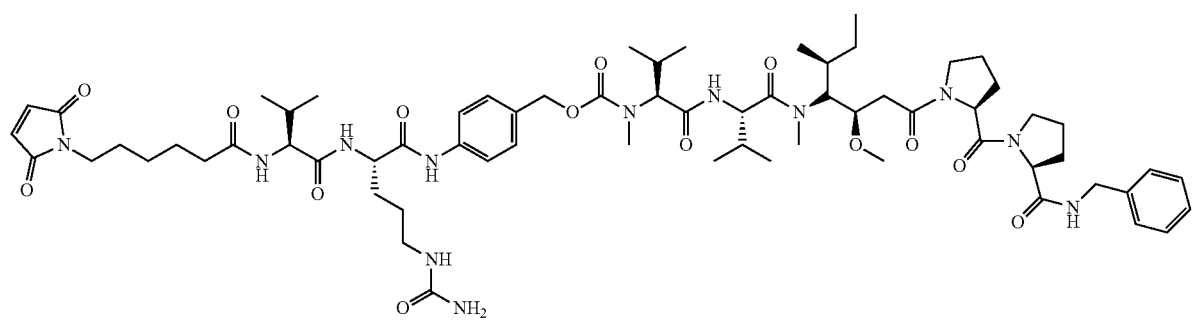

| | Antibody 1-Linking Assembly Unit Aa - conjugates (IC$_{50}$ in ng/mL) | | |
|---|---|---|---|
| Cell line | Comp. Ag (8) | Comp. Aa (8) | Comp. Ag (8)-Comp. Aa (8) |
| MDA-MIB-231 | >2000 | 20 | 7 |

| | Antibody 1- Linking Assembly Unit Aa - conjugates (IC$_{50}$ in ng/mL) | | |
|---|---|---|---|
| Cell line | Comp. Ag (8) | MMAE (8) | Comp. Ag (8)-MMAE (8) |
| L428 | >2000 | 456 | 32 |

Vinblastine/Auristatin Co-Conjugates
Targeting CD19
Comp. Ah:

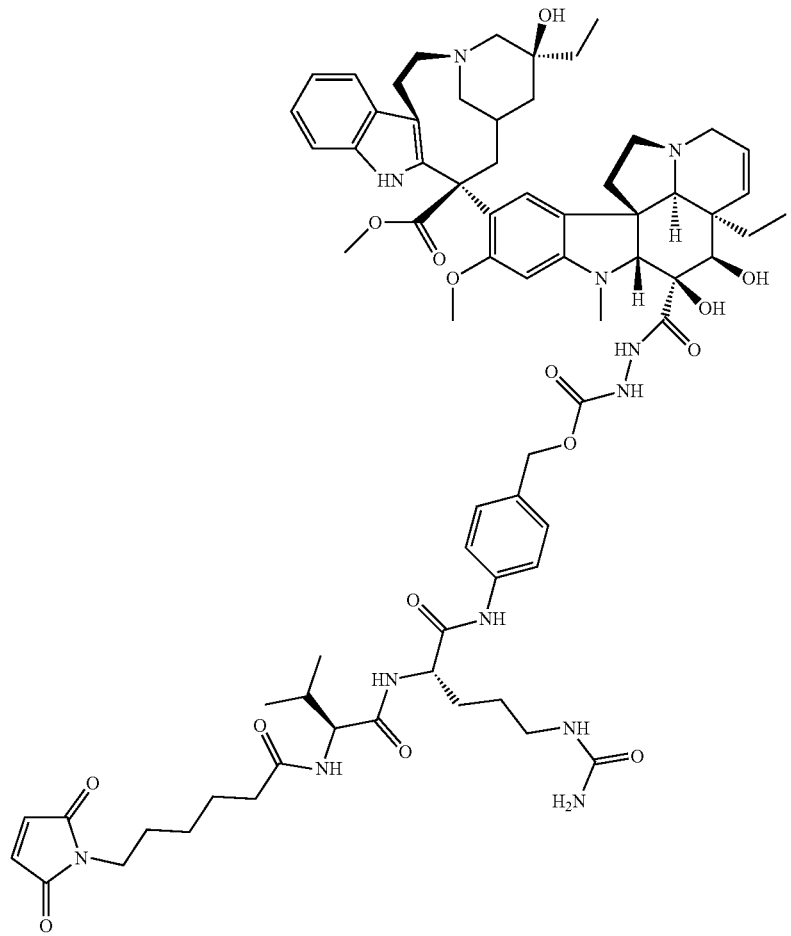

| Cell line | CD19 | Comp. Aa (8) | Comp. Ab (8) | Comp. Ah (8) | Comp. Aa (8) Comp. Ab (8) | Comp. Aa (8)-Comp. Ah (8) |
|---|---|---|---|---|---|---|
| Raji | 100k | 33 | 80 | 97 | 3 | 5 |
| RL | 27k | 4 | 340 | 60 | 1 | 2 |
| Nalm-6 | 70k | 8 | 5 | 9 | 2 | 3 |
| WSU-DLCL2 | 30k | 6 | 10 | 7 | 1 | 2 | hBU12 - Linking Assembly Unit Aa - conjugates (×50 in ng/mL)

Targeting Antigen 1

Antibody 1-Linking Assembly Unit Aa - conjugates ($1C_{50}$ in ng/mL)

| Cell line | Comp. Aa (8) | Comp. Ah (8) | Comp. Aa (8)-Comp. Ah (8) |
|---|---|---|---|
| HuH-7 | 8 | >2000 | 3 |
| MDA-MB-231 | 20 | 1860 | 11 |

Example 9: In Vitro Resistance Assays

Two different assays were used to evaluate whether dual-auristatin ADCs were more effective at limiting outgrowth of ADC-resistant cells: chronic exposure assays or colony forming assays. This analysis was conducted on either JHH-7 (hepatocarcinoma cells) or MCF-7 (LIV-1positive) cells using antigen specific dual-auristatin ADCs. Despite providing similar $IC_{50}$ values using a Cell Titer Glo cell proliferation assay to a 16-load mcMMAF ADC, a dual-auristatin conjugate targeting hepatocarcinoma cells was more effective at limiting outgrowth of resistant cells. A dual-auristatin ADC targeting the LIV-1antigen on MCF-7 cells also allowed for less outgrowth of resistant colonies compared to single-drug ADCs.

Chronic Exposure Assay

For chronic exposure assays, 10 million cells were plated in a T225 flask in the appropriate cell media. ADC was added at a concentration of 100 ng/mL. Media was replaced every four days containing fresh ADC. After 15 days, the cells were washed with PBS, fixed with 3.7% paraformaldehyde, and then stained with a 0.5% solution of crystal violet. The number of remaining cell colonies (>5 cells) was then counted.

Results for h25G5 ADCs:

| Treatment<br>h25G5- Linking<br>Assembly Unit Aa (8) | Cell Titer<br>Glo-IC$_{50}$ | Colonies |
|---|---|---|
| -Comp. Ab (16) | 124 | ≈5800 |
| -Comp. Aa (16) | 14 | ≈2500 |
| -Comp. Aa (8)-Comp. Ab (8) | 17 | ≈650 |

Figure 13:
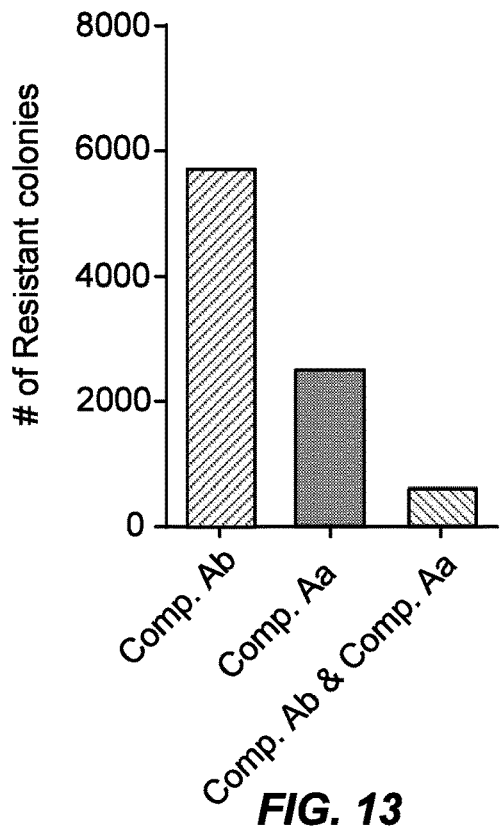
FIG. 13 shows that the multi-drug ADC comprising Comp. Aa and Comp. Ab limits the outgrowth of ADC-resistant cells as compared to ADCs with single-drug loading (just Comp. Aa or just Comp. Ab) in the chronic treatment assay. This experiment was performed with JHH-7 cells.

The data in the table provided above is shown graphically in FIG. 13.

Colony Forming Assays:

For testing hepatocarcinoma cells targeted ADCs, JHH-7 hepatocellular carcinoma cells (were plated in 6-well tissue culture plates at a density of 1000 cells per well. ADCs were added to cells at a concentration of 50 ng/mL for 48 hours. At this time, media was removed and cells were washed with PBS. Fresh media was added and the cells allowed to recover for 7-9 days. Cells were then washed with PBS, fixed with 3.7% paraformaldehyde, stained with 0.5% crystal violet, and then counted. Each condition was conducted with N=2.

For testing of LIV-1 targeted ADCs, MCF-7 breast carcinoma cells (ATCC) were plated in 6-well tissue culture plates at a density of 10,000 cells per well. ADCs were added to cells at a concentration of 100 ng/mL for 48 hours. At this time, media was removed and cells were washed with PBS. Fresh media was added and the cells allowed to recover for 7-9 days. Cells were then washed with PBS, fixed with 3.7% paraformaldehyde, stained with 0.5% crystal violet, and then counted. Each condition was conducted with N=2.

| Treatment<br>h25G5- Linking<br>Assembly Unit Aa (8) | Cell Titer<br>Glo-IC$_{50}$ | Colony<br>forming<br>units |
|---|---|---|
| Untreated | — | 178.5 |
| -Comp. Ab (16) | 124 | 118.5 |
| -Comp. Aa (16) | 14 | 48 |
| -Comp. Aa (8)-Comp. Ab (8) | 17 | 14.5 |

| Treatment<br>hLIV22- Linking<br>Assembly Unit Aa (8) | Colony<br>forming<br>units |
|---|---|
| Untreated | 91 |
| -MMAE (16) | 42.5 |
| -Comp. Aa (16) | 26 |
| -Comp. Aa (8)-MMAE (8) | 19.5 |

Figure 14:
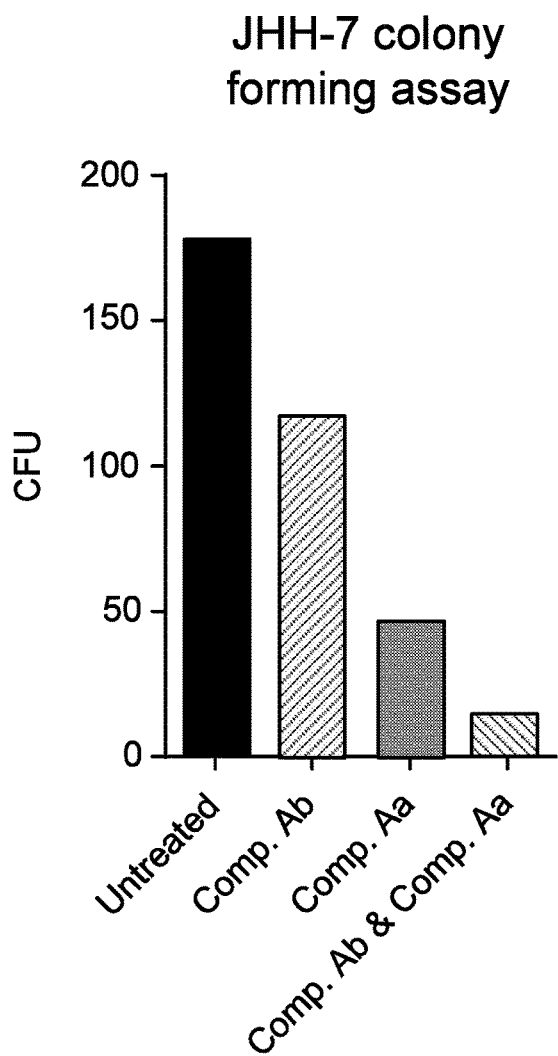
FIG. 14 shows that the multi-drug ADC comprising Comp. Aa and Comp. Ab limits the outgrowth of ADC-resistant cells as compared to ADCs with single-drug loading (just Comp. Aa or just Comp Ab) or untreated cells in the colony forming assay. This experiment was performed with JHH-7 cells.
Figure 15:
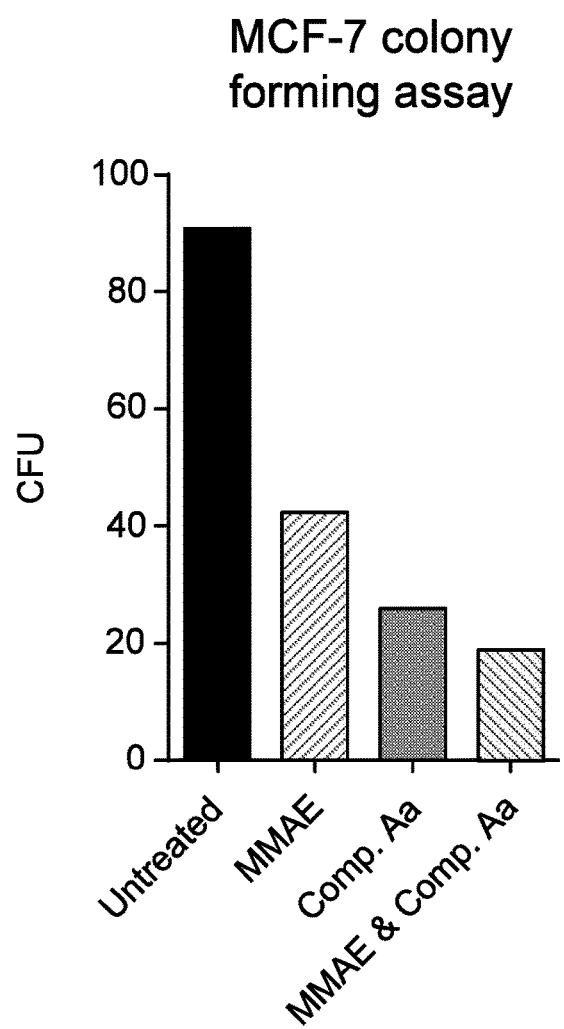
FIG. 15 shows that the multi-drug ADC comprising Comp. Aa and MMAE limits the outgrowth of ADC-resistant cells as compared to ADCs with single-drug loading (just Comp. Aa or just MMAE) or untreated cells in the colony forming assay. This experiment was performed with MCF-7 cells.

The data provided in the Tables above are shown graphically in FIGS. 14 and 15, respectively.

Example 10: Drug Carrier Bearing 3 Cysteines for 16+8 Drug Loading

Linking Assembly Unit Ac:

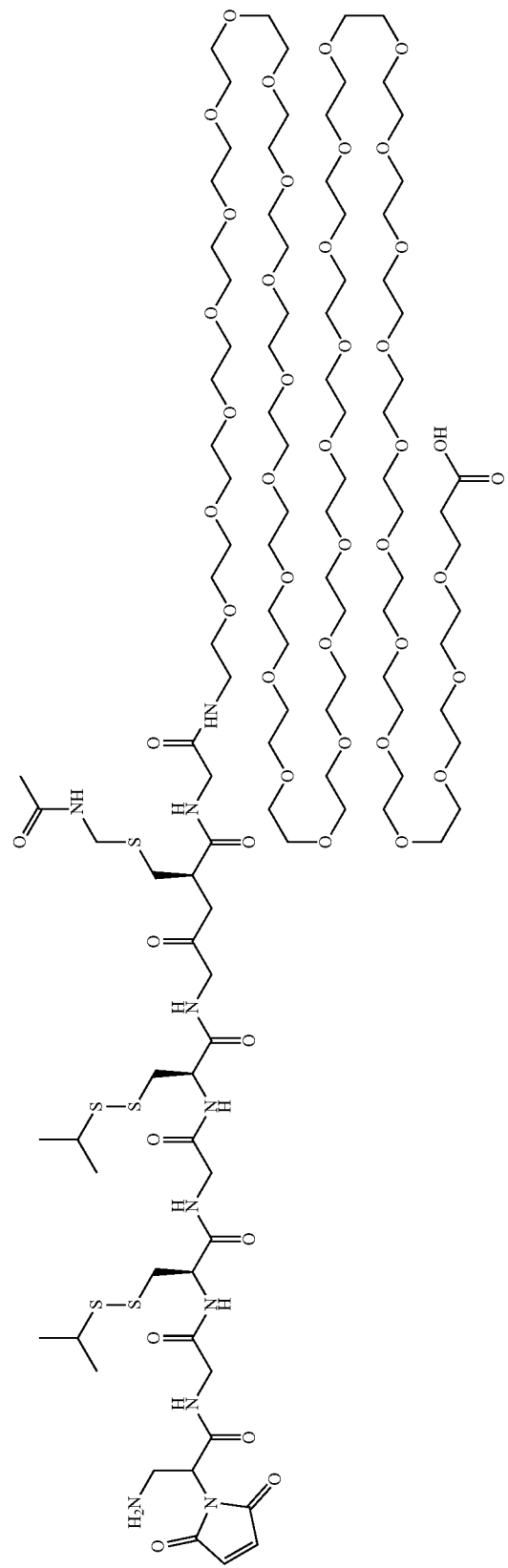

Figure 16A:
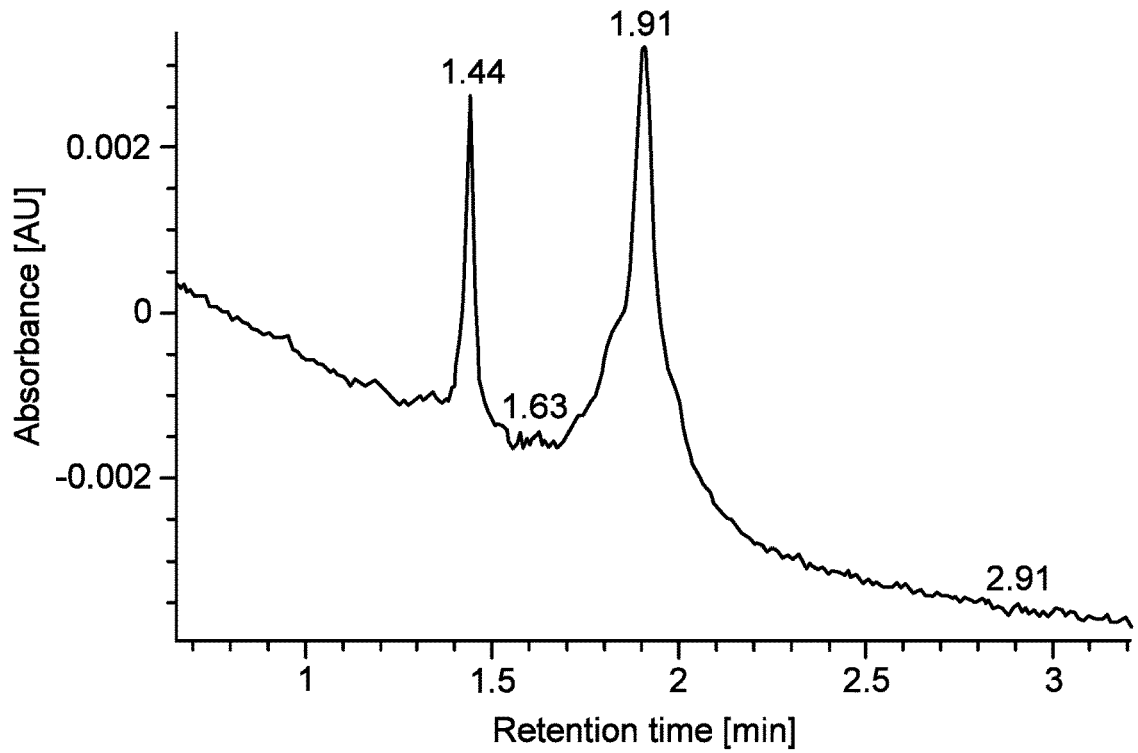
FIG. 16A-B show analytical data for preparing a drug carrier bearing 3 cysteines for 16+8 drug loading. (A) UV chromatogram (280 nm) after reverse-phase separation of light and heavy chain of the 24-load MD ADC. Note that a single light and heavy chain peak are present. The peak eluting at 1.44 min is fully loaded light chain (LC). The peak eluting at 1.91 min is fully loaded heavy chain (HC); (B) Deconvoluted light chain mass of a 24-load (16+8) MD ADC using drug carrier 3 on cAC10 antibody The observed m/z corresponds to a fully conjugated light chain bearing carrier 3, and 3 total drug units (split 2+1).
Figure 16B:
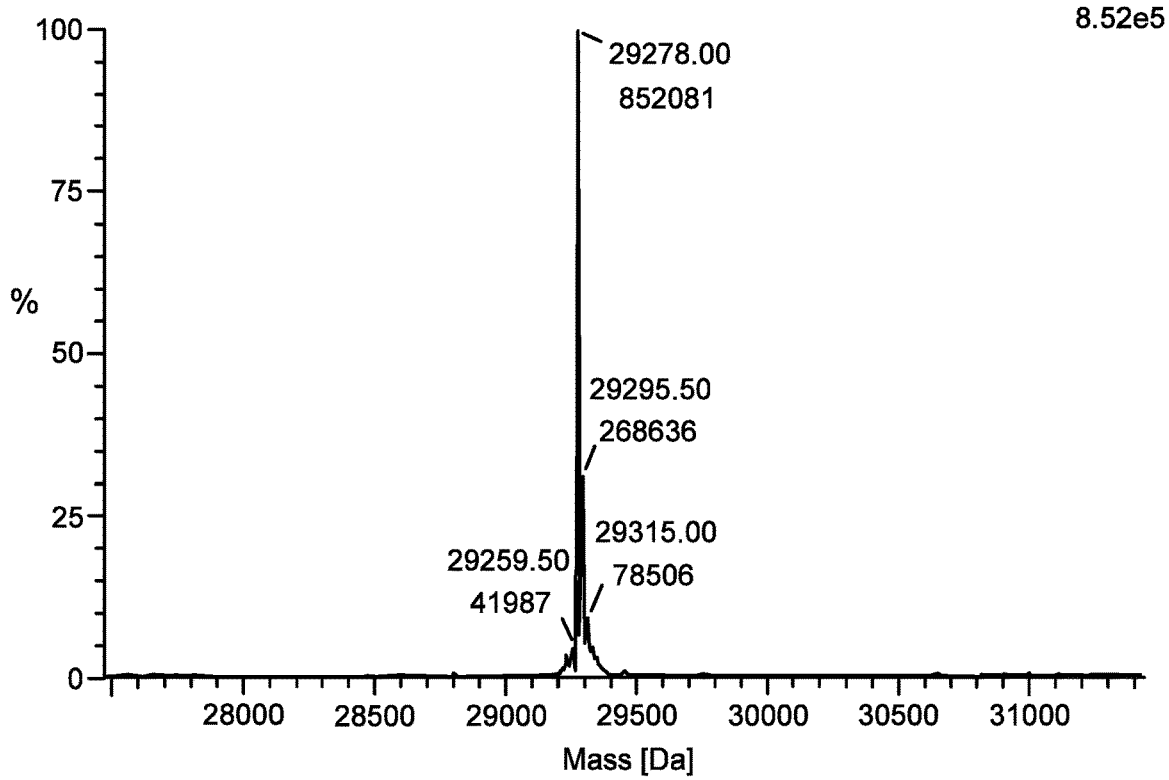
Figure 17A:
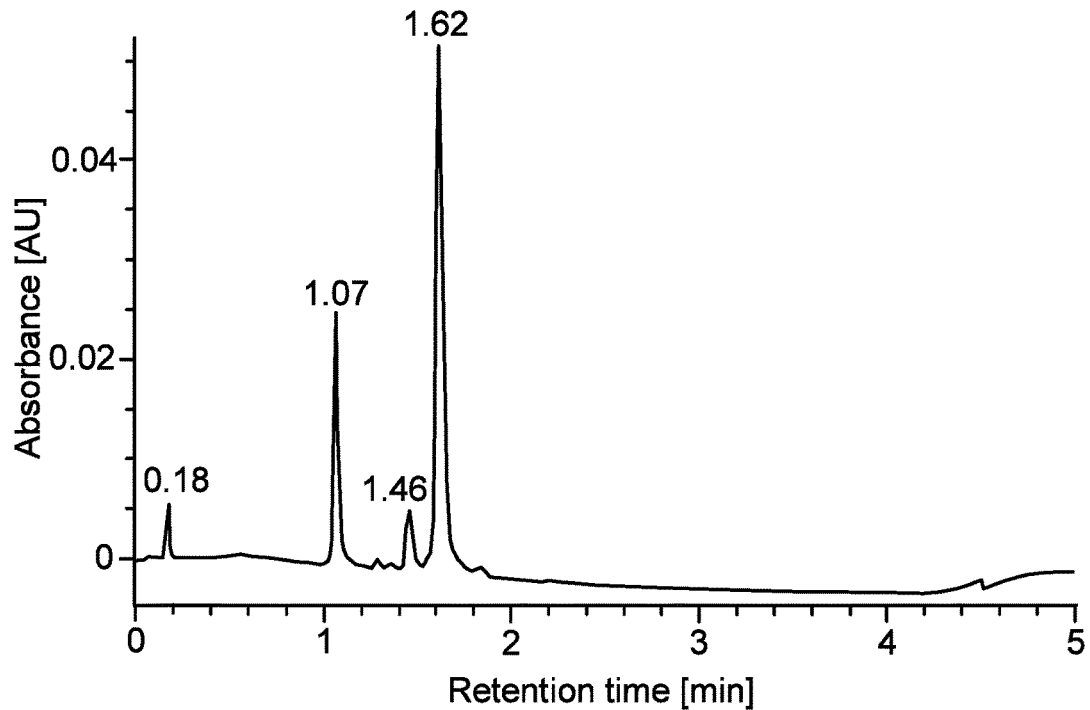
FIG. 17A-E show analytical data for preparing a dual loaded L49-Linking Assembly Unit Ab (8)-Comp. Aj(8)-Comp. Ak (8) without a PEG group. (A) UV chromatogram (280 nm) after reverse-phase separation of light and heavy chain of the MD ADC. The peak eluting at 1.07 min is fully loaded LC. The peak eluting at 1.62 min is fully loaded HC. The peak eluting at 1.46 min is under-loaded for the second conjugated drug (2 drugs per HC instead of 3); (B) Deconvoluted light chain mass of a 16-load (8+8) MD ADC using a drug carrier without a PEG arm; (C) Deconvoluted heavy chain mass of a fully-conjugated 16-load (8+8) MD ADC using a drug carrier without a PEG arm; (D) Size-exclusion chromatography of L49-Linking Assembly Unit Ab (8)-Comp. Aj(8)-Comp. Ak (8) without a PEG group. Co-conjugates on non-pegylated scaffolds have minimal aggregation; (E) L49-Linking Assembly Unit Ab (8)-Comp. Aa(8)-Comp. Ak (8) without a PEG group. Co-conjugates on non-pegylated scaffolds have minimal aggregation.
Figure 17B:
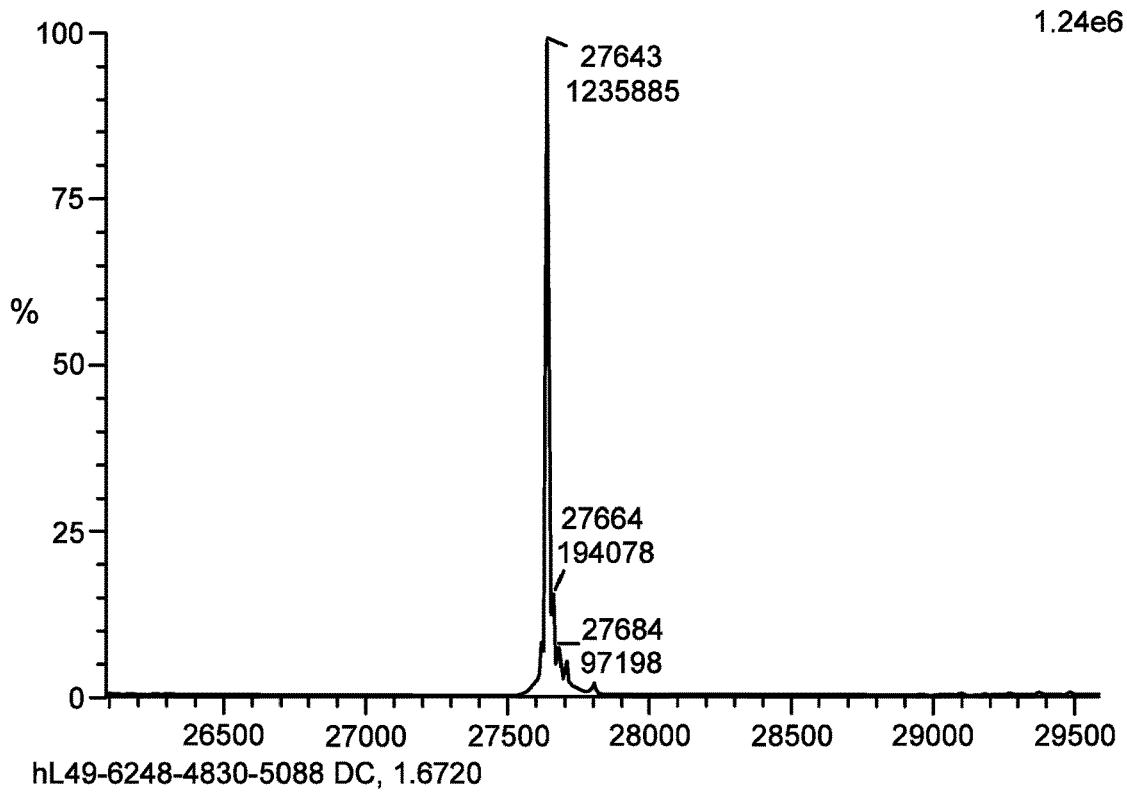
Figure 17C:
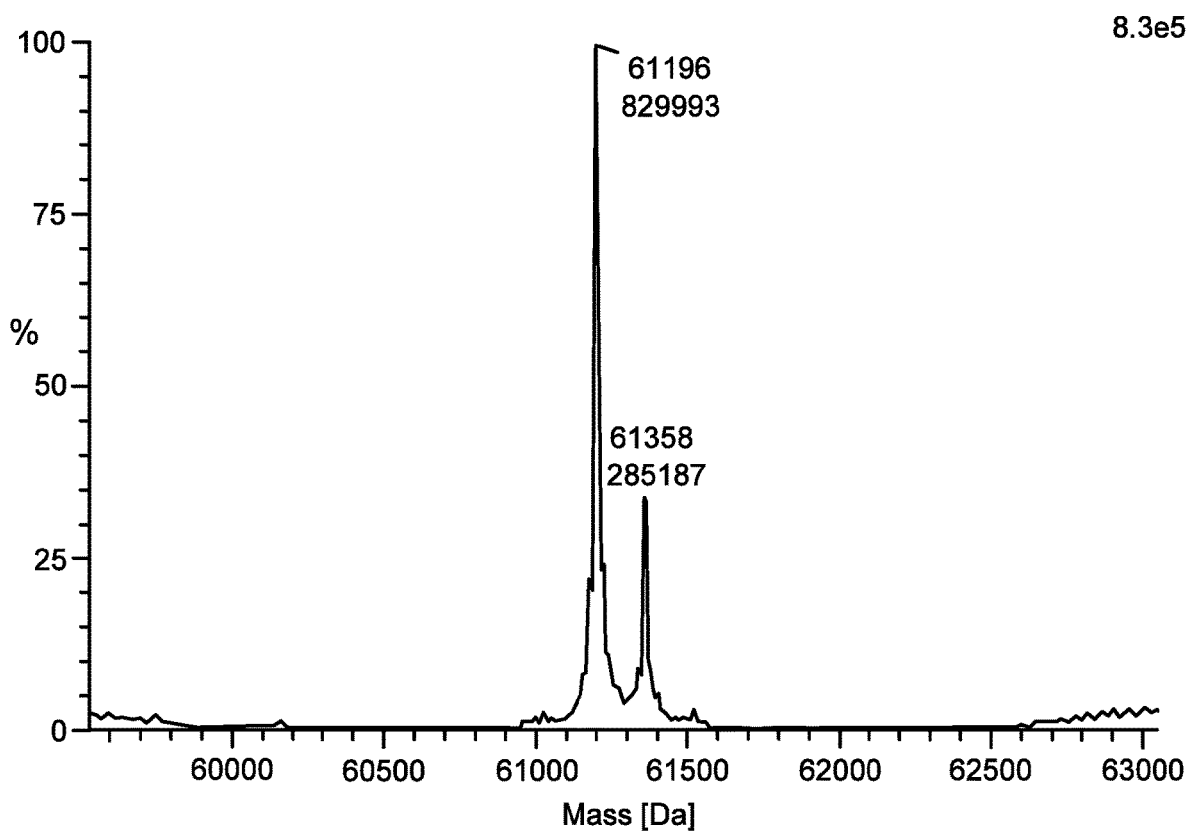
Figure 17D:
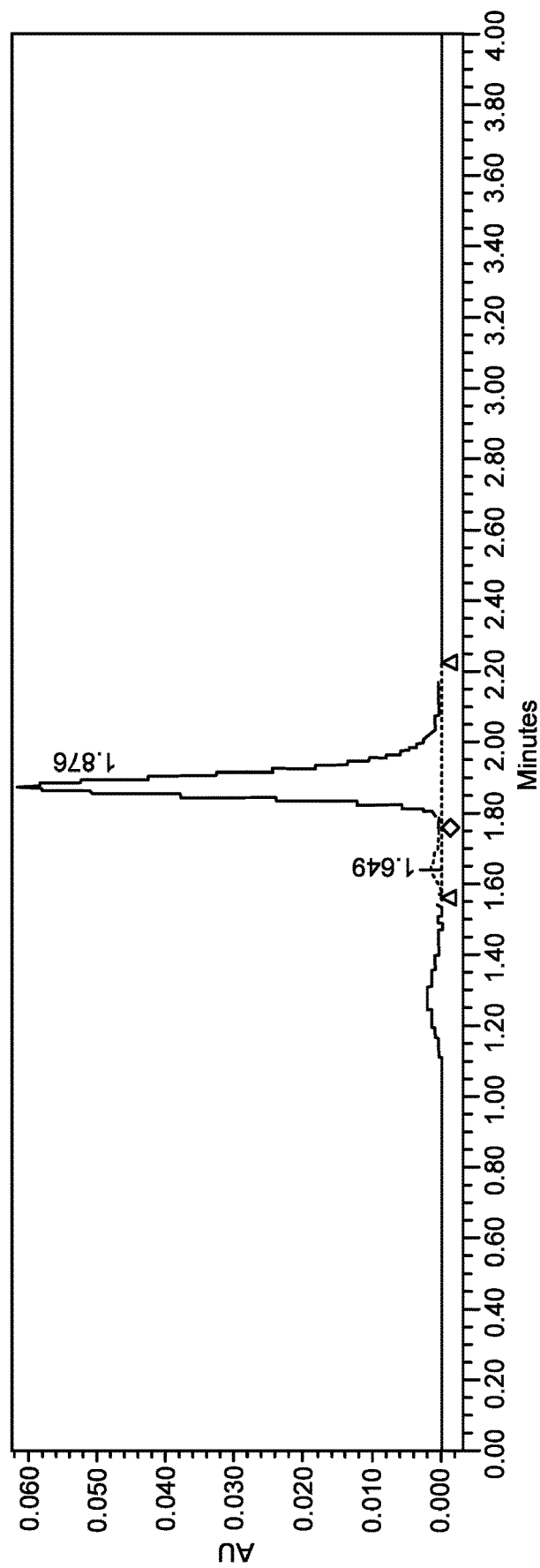
Figure 17E:
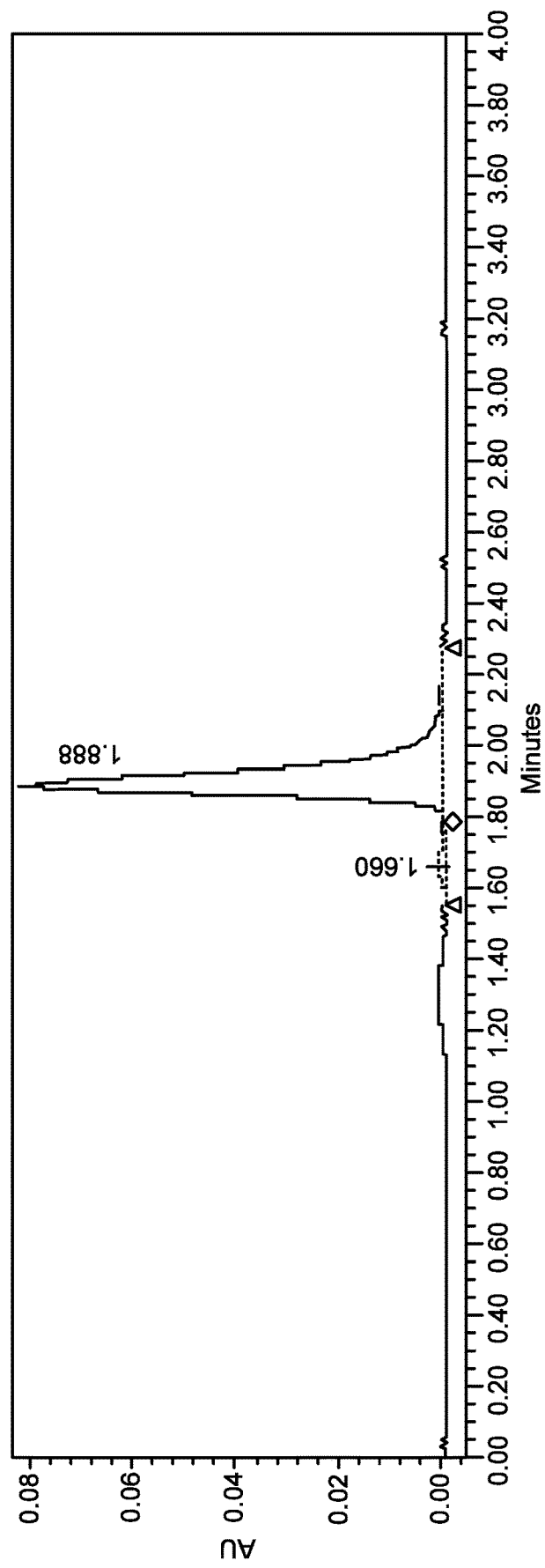

Preparation of cAC0-Linking Assembly Unit Ac (8)-Comp. Ai(16)-Comp. Ah(8):

The same procedure was followed as for dual conjugation using a carrier bearing a single Cys(SiPr) residue, except that 25 equiv. of TCEP were used for reduction of the —SiPr groups. Characterization data is shown in FIGS. 16A and 16B.

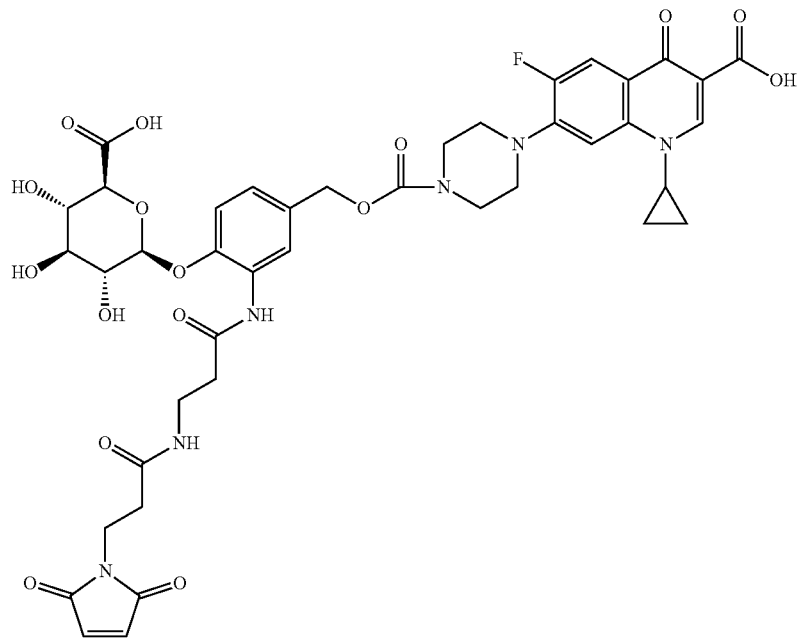 [SMILES: O=C(CCN1C(=O)C=CC1=O)NCCC(=O)Nc1cc(COC(=O)N2CCN(c3cc4c(cc3F)c(=O)c(C(=O)O)cn4C3CC3)CC2)ccc1O[C@@H]1O[C@H](C(=O)O)[C@@H](O)[C@H](O)[C@H]1O]

Comp. Ai (ciprofloxacin)

Example 11: A PEG Arm is not Required for Dual-Conjugates Bearing Hydrophilic Drugs

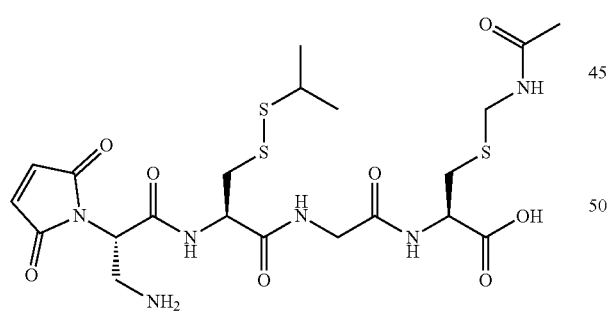

Linking Assembly Unit Ab:

Expected exact mass: 593.1; observed m/z: 593.2 (M+H)$^+$, LC-MS $t_R$=0.68 min.

Protecting groups (—S-iPr and —CH$_2$—NH—C(=O) CH$_3$) are removed individually and desired drug groups are attached in the above shown Linking Assembly Unit. The same procedure was followed for preparing dual conjugates as discussed above. Analytic data for preparing a co-conjugate incorporating Comp. Aj and Comp. Ak to Linking Assembly Unit Ab and antibody L49 is shown in FIG. 17A-E.

Comp. Aj (Auristatin T):

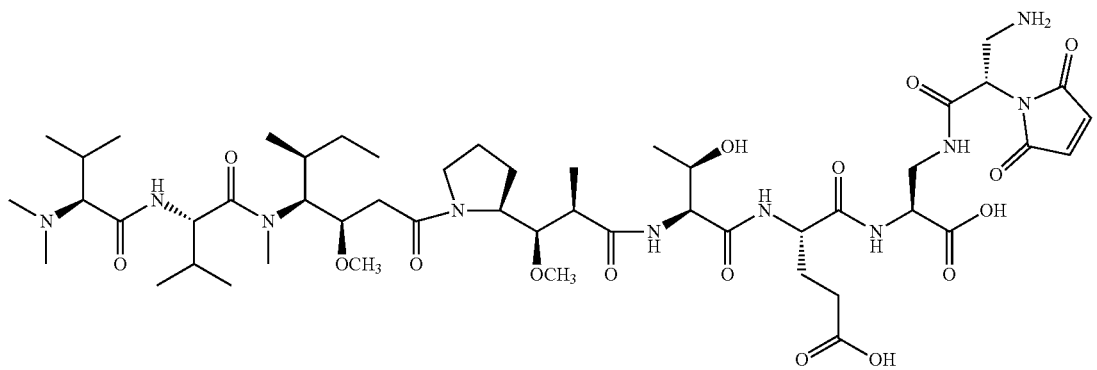 [SMILES: CC[C@H](C)[C@@H]([C@@H](CC(=O)N1CCC[C@H]1[C@H](OC)[C@@H](C)C(=O)N[C@H](C(=O)N[C@@H](CCC(=O)O)C(=O)N[C@@H](CNC(=O)[C@H](CN)N1C(=O)C=CC1=O)C(=O)O)[C@@H](C)O)OC)N(C)C(=O)[C@@H](NC(=O)[C@H](C(C)C)N(C)C)C(C)C]

Comp. Ak (MMAE):

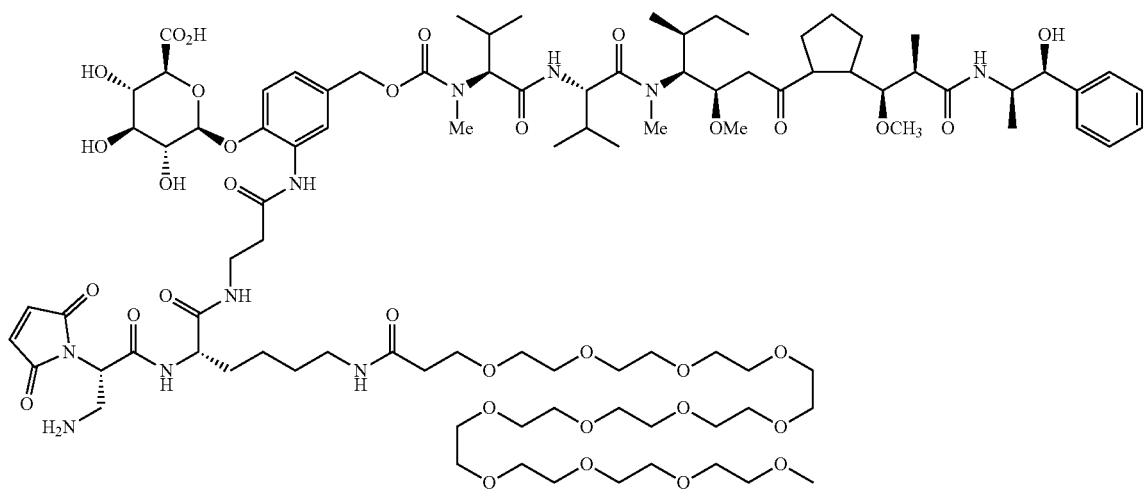 [SMILES: CC[C@H](C)[C@@H]([C@@H](CC(=O)C1CCCC1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c(NC(=O)CCNC(=O)[C@H](CCCCNC(=O)CCOCCOCCOCCOCCOCCOCCOCCOCCOCCOCCOCCOC)NC(=O)[C@H](CN)N2C(=O)C=CC2=O)c1)C(C)C]

Example 12: In Vitro Cytotoxicity of Dual-Auristatin ADCs on L49 Antibody Targeting MFI2 (p97)

The in vitro cytotoxic activity of various dual-auristatin ADCs were tested using methods similar to those described above. The results are presented in the table below.
L49-Linking Assembly Unit Ab (8)-ADCS

| Cell line | L49 - Linking Assembly Unit Ab - conjugates ($IC_{50}$ in ng/mL) | | | | | | | |
|---|---|---|---|---|---|---|---|---|
| | Comp. Ak (8) | Comp. Ak (16) | Comp. Aj (8) | Comp. Aj (16) | Comp. Aa (8) | Comp. Aa (16) | Comp. Aj (8)-Comp. Ak (8) | Comp. Aa(8)-Comp. Ak (8) |
| A375 | 43.9 | 13.5 | 7.7 | 2.4 | 9.7 | 2.5 | 1.3 | 2.4 |
| IGR37 | 2.2 | 0.9 | 1.5 | 0.5 | 2.5 | 1.5 | 0.06 | 0.8 |
| Colo-853 | 27.4 | 13.3 | 5.2 | 1.6 | 7.8 | 5.2 | 3.5 | 4.8 |

REFERENCES

[1] R. P. Lyon, J. R. Setter, T. D. Bovee, S. O. Doronina, J. H. Hunter, M. E. Anderson, C. L. Balasubramanian, S. M. Duniho, C. I. Leiske, F. Li, P. D. Senter, *Nat. Biotechnol.* 2014, 32, 1059-1062.

[2] S. O. Doronina, B. E. Toki, M. Y. Torgov, B. A. Mendelsohn, C. G. Cerveny, D. F. Chace, R. L. DeBlanc, R. P. Gearing, T. D. Bovee, C. B. Siegall, J. A. Francisco, A. F. Wahl, D. L. Meyer, P. D. Senter, *Nat. Biotechnol.* 2003, 21, 778-784.

[3] S. O. Doronina, B. A. Mendelsohn, T. D. Bovee, C. G. Cerveny, S. C. Alley, D. L. Meyer, E. Oflazoglu, B. E. Toki, R. J. Sanderson, R. F. Zabinski, A. F. Wahl, P. D. Senter, *Bioconjug. Chem.* 2006, 17, 114-124.

[4] A. F. Wahl, K. Klussman, J. D. Thompson, J. H. Chen, L. V. Francisco, G. Risdon, D. F. Chace, C. B. Siegall, J. A. Francisco, *Cancer Res.* 2002, 62, 3736-3742.

[5] R. P. Lyon, D. L. Meyer, J. R. Setter, P. D. Senter, Methods Enzymol. 2012, 502, 123-138.

[6] T. S. Lewis, K. Gordon, F. Li, A. Weimann, R. Bruders, J. Miyamoto, N. M. Okeley, X. Zhang, D. Chace, C.-L. Law, Cancer Res. 2014, 74, 688-688.

[7] F. Li, K. K. Emmerton, M. Jonas, X. Zhang, J. B. Miyamoto, J. R. Setter, N. D. Nicholas, N. M. Okeley, R. P. Lyon, D. R. Benjamin, C. L. Law, Cancer Res. 2016.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A multi-drug antibody drug conjugate having the structure:

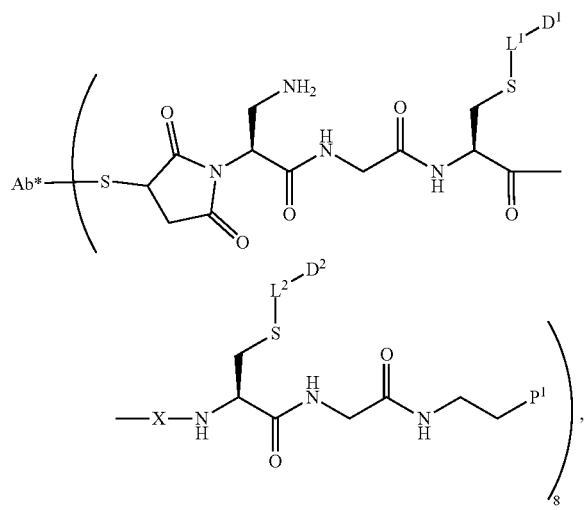

or in a hydrolyzed form wherein the succinimide is hydrolyzed, wherein

Ab* is an antibody comprising one or more engineered cysteine residues;

X is an Attachment Group Linker;

$D^1$ is a first Drug Unit;

$D^2$ is a second Drug Unit, wherein $D^1$ and $D^2$ are different Drug Units;

$L^1$ is an Optional Linking Group;

$L^2$ is an Optional Linking Group; and $P^1$ is a polyethylene glycol group.

2. The antibody drug conjugate of claim 1, wherein each of $L^1$ and $L^2$ is independently selected from the group consisting of maleimido-caproyl (mc), maleimido-caproyl-valine-citrulline (mc-vc), and maleimido-caproyl-valine-citrulline-paraaminobenzyloxycarbonyl (mc-vc-PABC), wherein the maleimido group is replaced by a succinimido group, optionally in a hydrolyzed form.

3. The antibody drug conjugate of claim 1, wherein $D^1$ and $D^2$ are independently selected from: the group consisting of MMAE, Auristatin T, MMAF and Dolastatin 10; or the group consisting of MMAE, camptothecin, Superdox, Dolastatin 10, Vinblastine and Ciprofloxacin.

4. The antibody drug conjugate of claim 1, wherein $D^1$ and $D^2$ are a drug pair selected from the group consisting of MMAE/MMAF, MMAE/camptothecin, Superdox/camptothecin, Superdox/MMAE, Dolastatin 10/MMAE, Dolastatin 10/MMAF, Vinblastine/MMAE, and Vinblastine/MMAF.

5. The antibody drug conjugate of claim 1, wherein $D^1$ and $D^2$ are a first anticancer agent and a second anticancer agent, respectively.

6. The antibody drug conjugate of claim 5, wherein the first anticancer agent and the second anticancer agent have complementary activity profiles.

7. The antibody drug conjugate of claim 5, wherein the first anticancer agent and the second anticancer agent are MMAE and MMAF or camptothecin and doxorubicin.

8. The antibody drug conjugate of claim 1, wherein the two Drug Units attached to the Linking Assembly Units are produced by thiol/maleimide coupling.

9. The antibody drug conjugate of claim 1, wherein X is an amino acid or a di- or tri-peptide.

10. The antibody drug conjugate of claim 9, wherein each amino acid present in X is selected from the group consisting of glycine and alanine.

11. A multi-drug antibody drug conjugate having the structure:

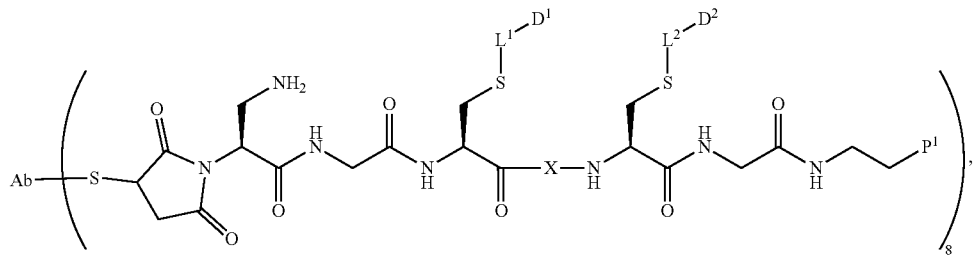

wherein

Ab is an antibody that is a non-engineered antibody;

$D^1$ is a first Drug Unit;

$D^2$ is a second Drug Unit, wherein $D^1$ and $D^2$ are different Drug Units;

$L^1$ is an Optional Linking Group;

$L^2$ is an Optional Linking Group; and $P^1$ is a polyethylene glycol group.

12. The antibody drug conjugate of claim 11, wherein each of $L^1$ and $L^2$ is independently selected from the group consisting of maleimido-caproyl (mc), maleimido-caproyl-valine-citrulline (mc-vc), and maleimido-caproyl-valine-citrulline-paraaminobenzyloxycarbonyl (mc-vc-PABC), wherein the maleimido group is replaced by a succinimido group, optionally in a hydrolyzed form.

13. The antibody drug conjugate of claim 11, wherein $D^1$ and $D^2$ are independently selected from: the group consisting of MMAE, Auristatin T, MMAF and Dolastatin 10; or the group consisting of MMAE, camptothecin, Superdox, Dolastatin 10, Vinblastine and Ciprofloxacin.

14. The antibody drug conjugate of claim 11, wherein $D^1$ and $D^2$ are a drug pair selected from the group consisting of MMAE/MMAF, MMAE/camptothecin, Superdox/camptothecin, Superdox/MMAE, Dolastatin 10/MMAE, Dolastatin 10/MMAF, Vinblastine/MMAE, and Vinblastine/MMAF.

15. A multi-drug antibody drug conjugate having a structure selected from the group consisting of:

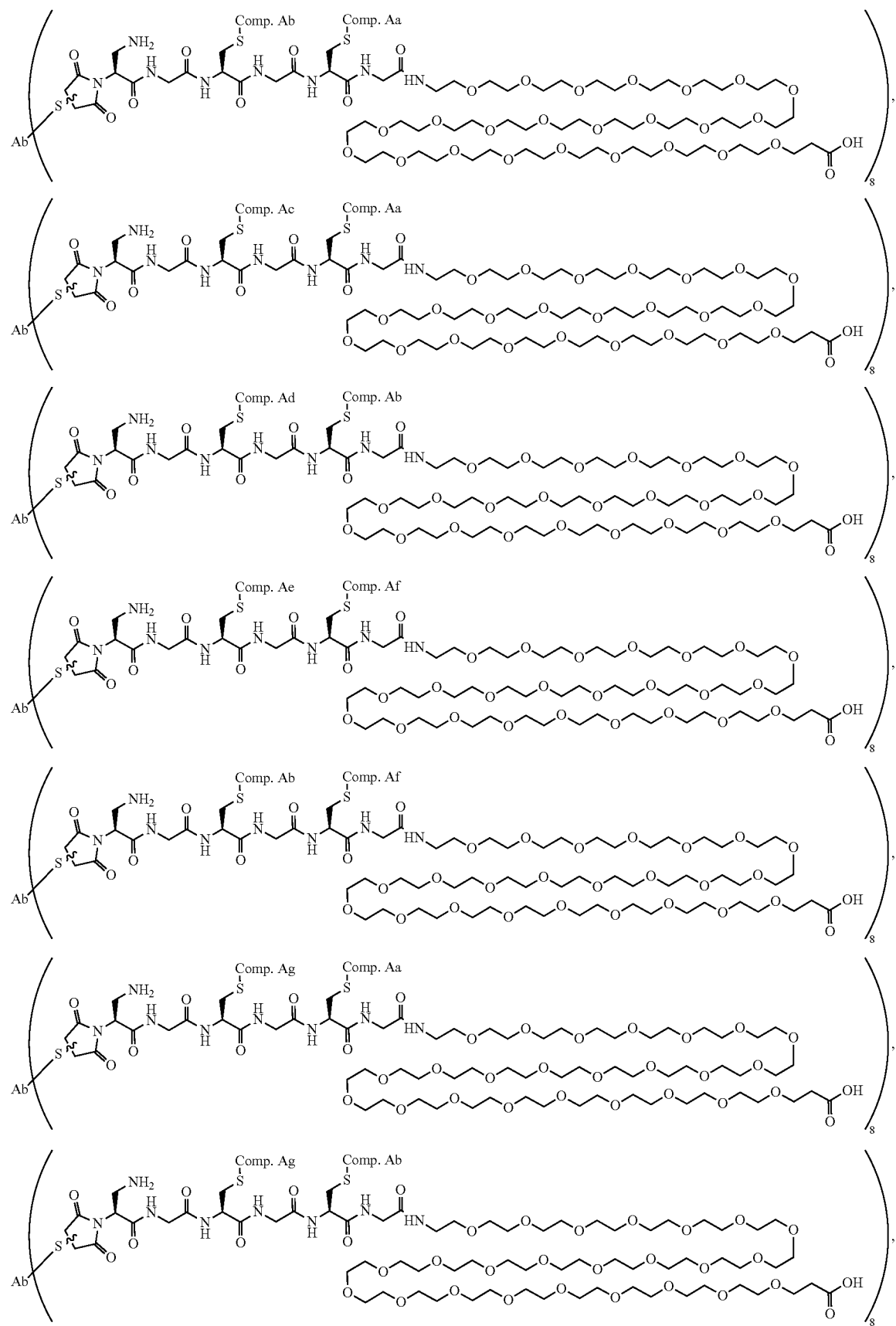

-continued
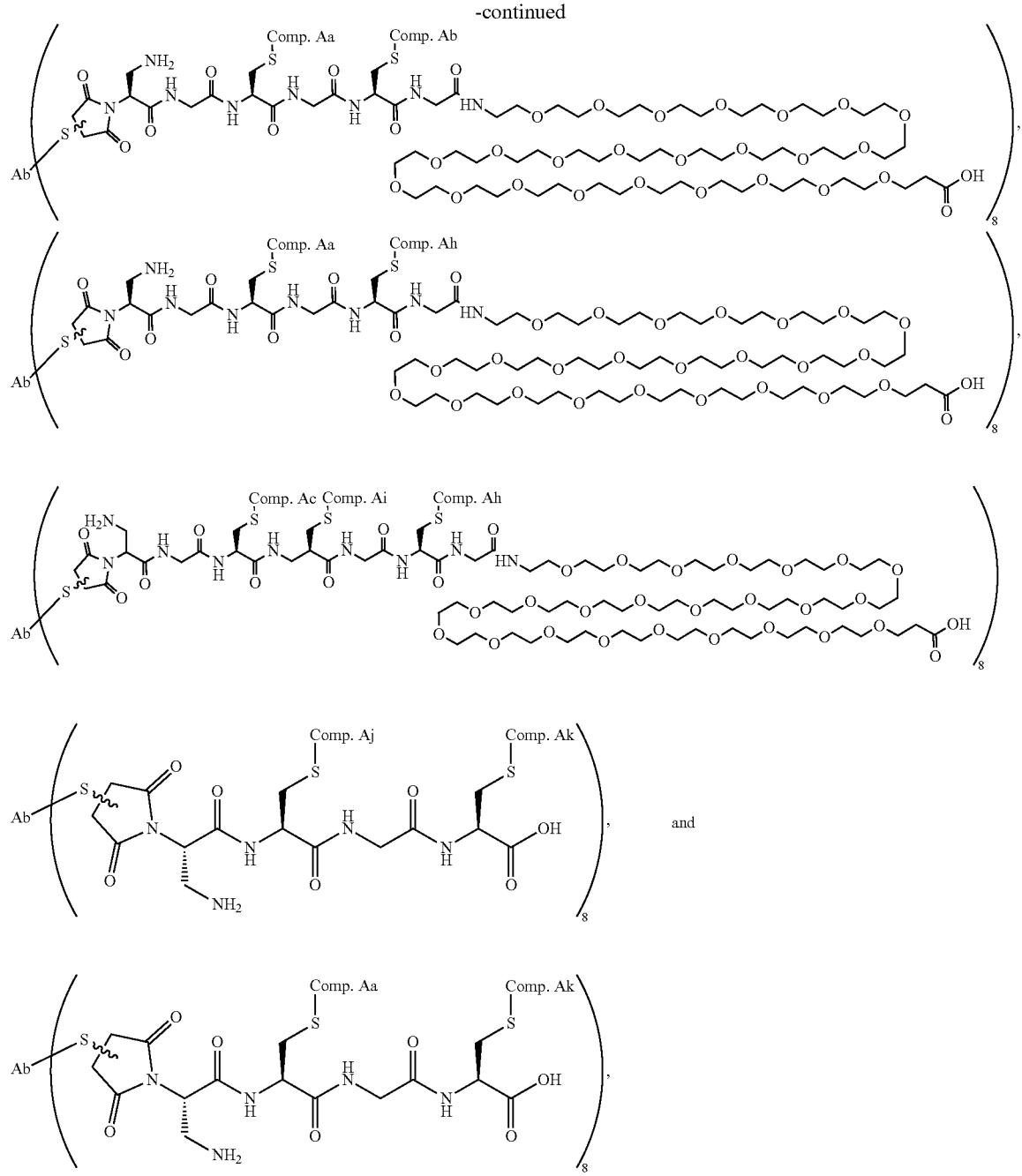
wherein
Comp. Aa is:
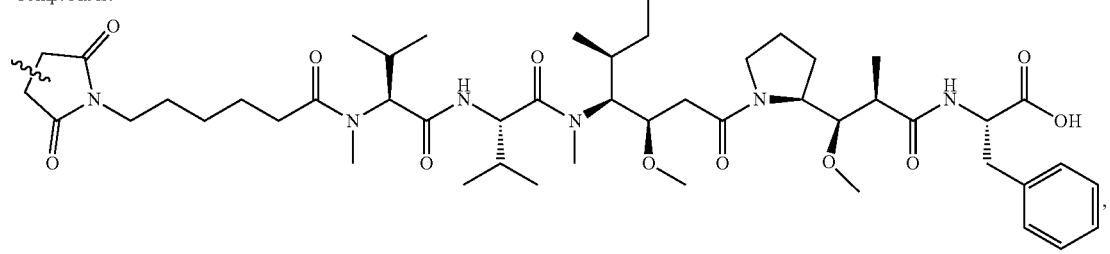

-continued
Comp. Ab is:
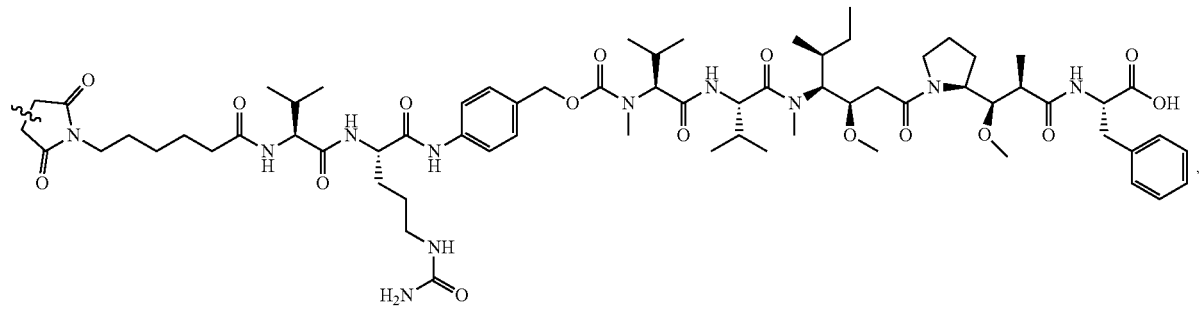
Comp. Ac is:
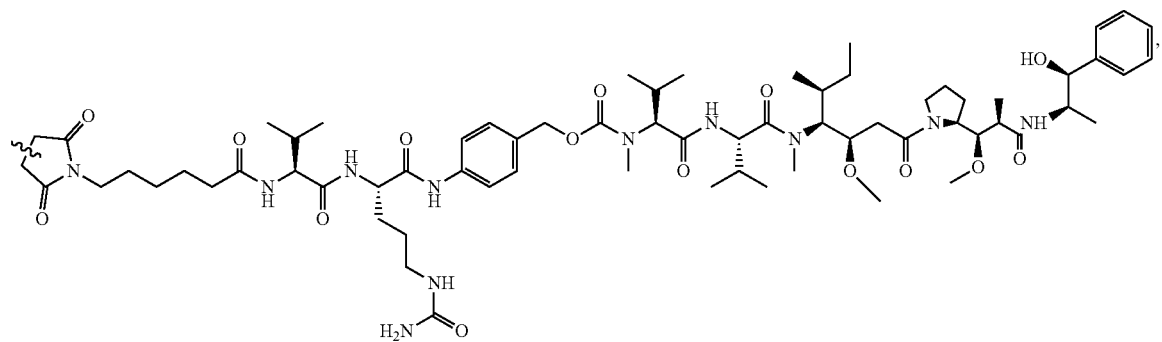
Comp. Ad is:
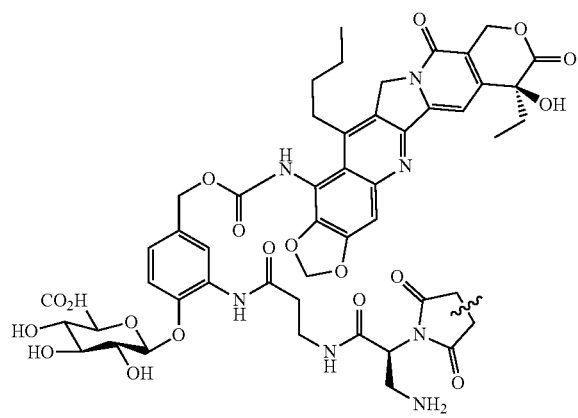
Comp. Ae is:
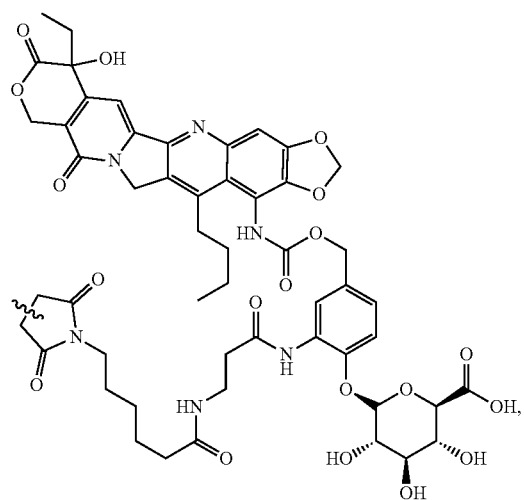

Comp. Af is:
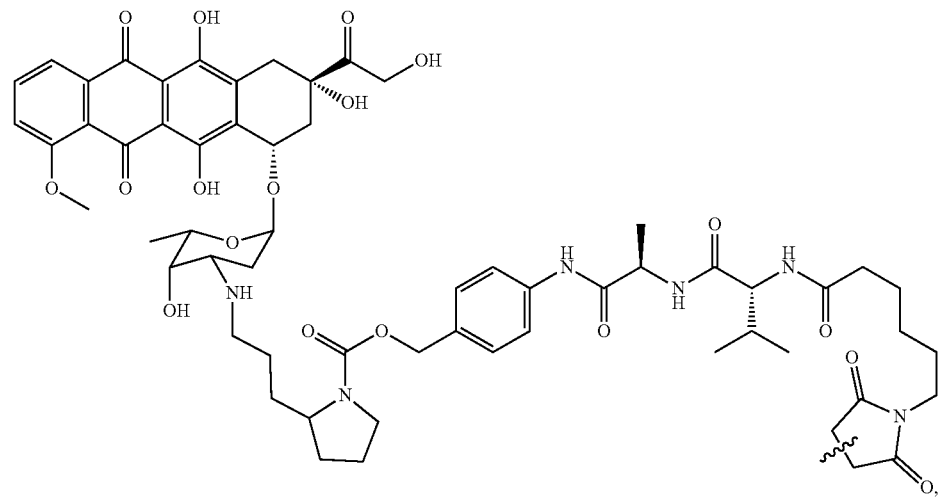
Comp. Ag is:
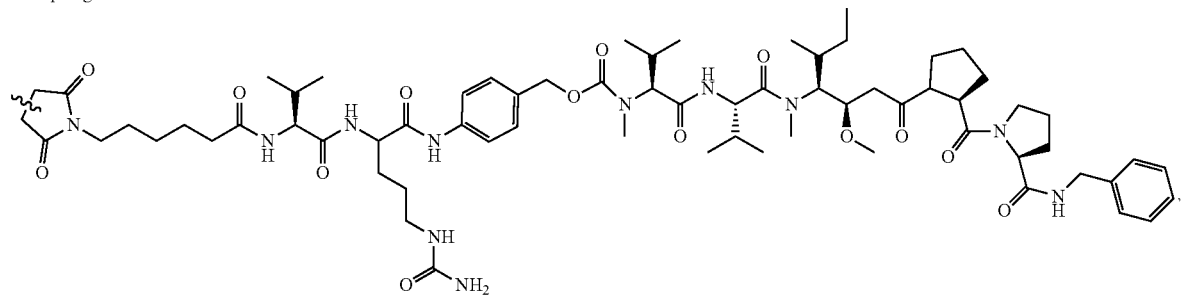

-continued
Comp. Ah is:
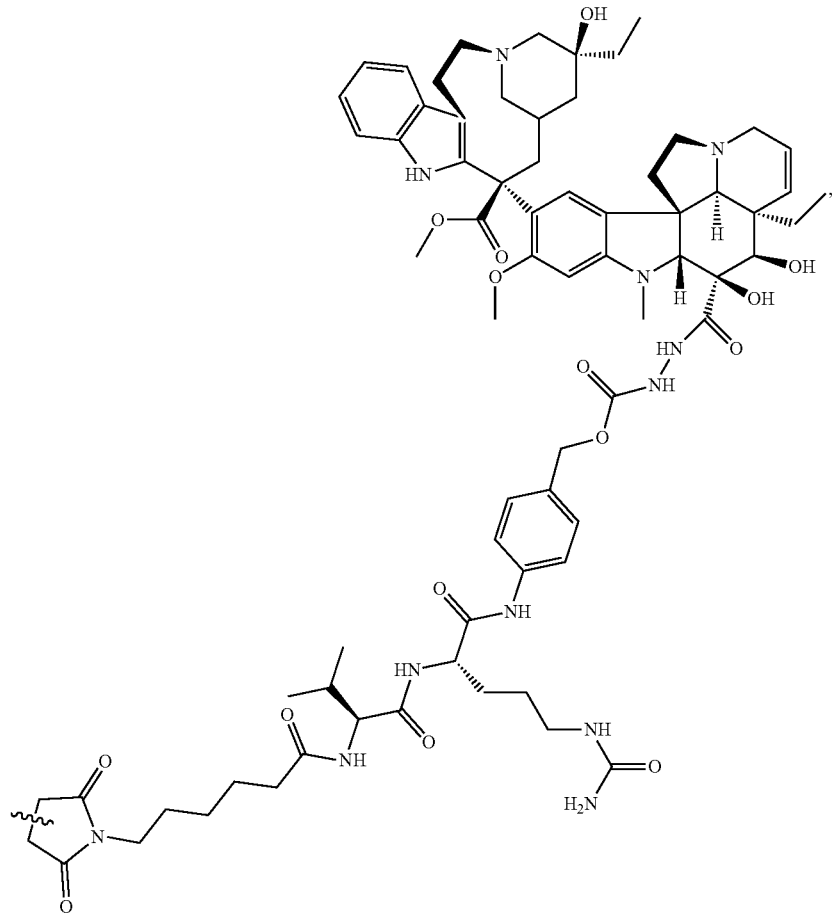
Comp. Ai is:
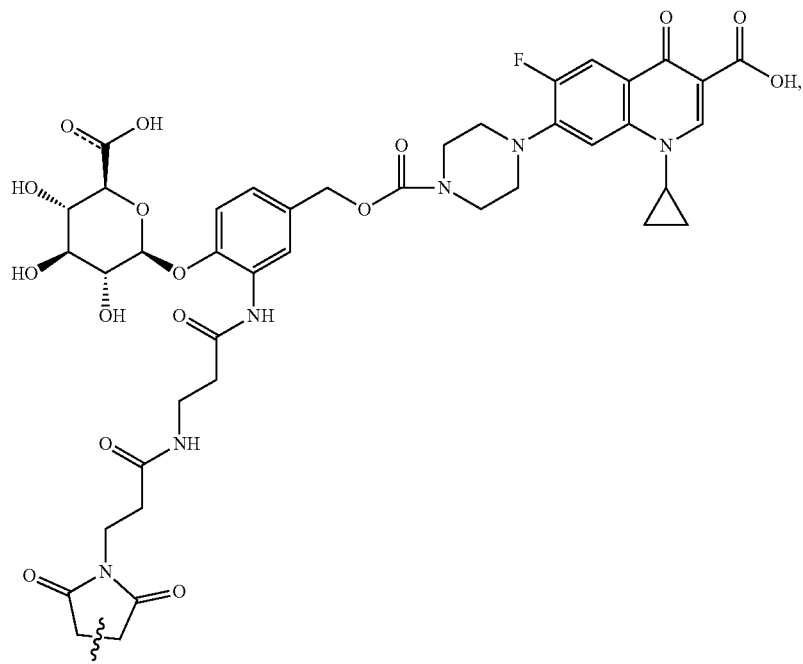

Comp. Aj is:
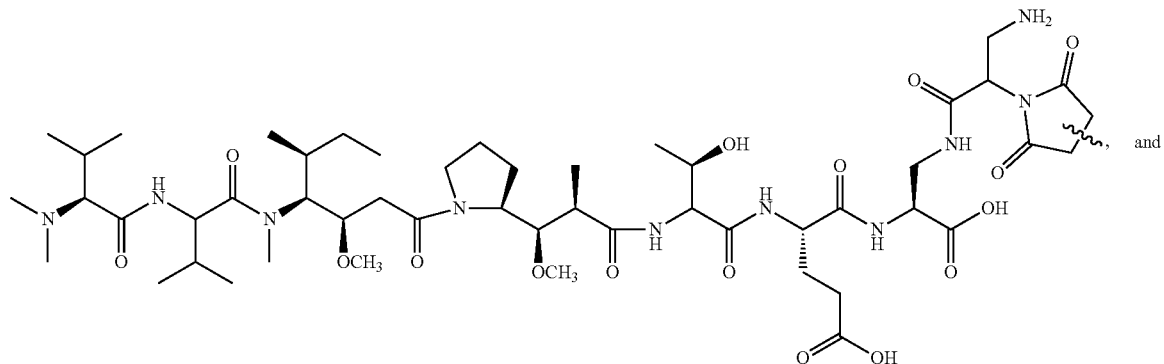
Comp. Ak is:
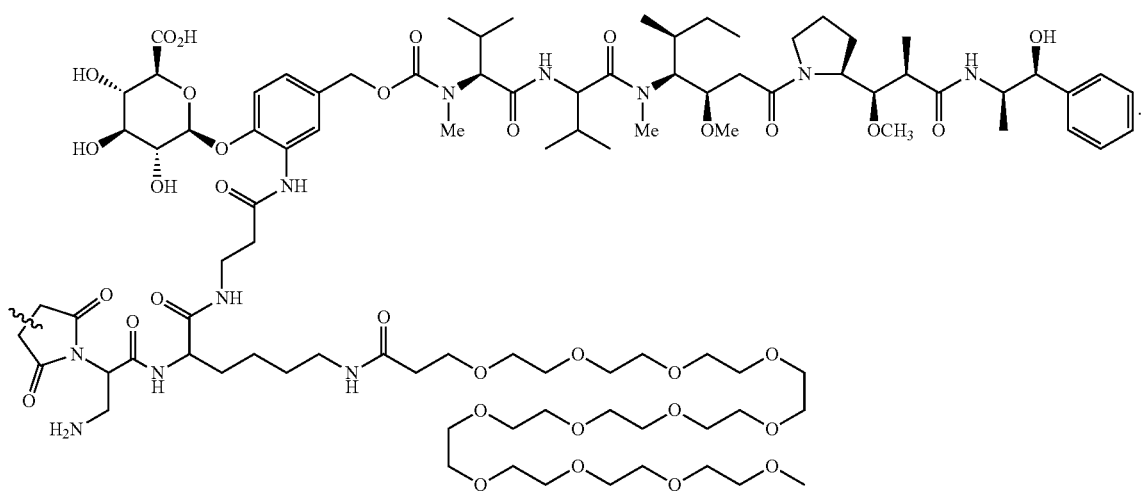
* * * * *

SEQUENCE LISTING

```
<160> NUMBER OF SEQ ID NOS: 10

<210> SEQ ID NO 1
<211> LENGTH: 117
<212> TYPE: PRT
<213> ORGANISM: Mus musculus

<400> SEQUENCE: 1

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Thr Trp Val Lys Gln Lys Pro Gly Gln Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
                100                 105                 110

Val Thr Val Ser Ala
            115

<210> SEQ ID NO 2
<211> LENGTH: 111
<212> TYPE: PRT
<213> ORGANISM: mus musculus

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
                20                  25                  30

Gly Asp Ser Tyr Met Asn Trp Tyr Gln Gln Lys Pro Gly Gln Pro Pro
            35                  40                  45

Lys Val Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
                100                 105                 110

<210> SEQ ID NO 3
<211> LENGTH: 118
<212> TYPE: PRT
<213> ORGANISM: Artificial
```

```
<220> FEATURE:
<223> OTHER INFORMATION: Humanized murine sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Thr Tyr Thr Gly Glu Pro Thr Tyr Ala Asp Ala Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
                100                 105                 110

Thr Val Thr Val Ser Ser
                115

<210> SEQ ID NO 4
<211> LENGTH: 112
<212> TYPE: PRT
<213> ORGANISM: Artificial
<220> FEATURE:
<223> OTHER INFORMATION: Humanized murine sequence

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
                20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gly Gly Thr Lys Val Glu Ile Lys Arg
                100                 105                 110

<210> SEQ ID NO 5
<211> LENGTH: 120
<212> TYPE: PRT
<213> ORGANISM: Artificial
<220> FEATURE:
<223> OTHER INFORMATION: Humanized murine sequence

<400> SEQUENCE: 5

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
                20                  25                  30

Gly Met Gly Val Gly Trp Ile Arg Gln His Pro Gly Lys Gly Leu Glu
            35                  40                  45
```

-continued

```
Trp Ile Gly His Ile Trp Trp Asp Asp Asp Lys Arg Tyr Asn Pro Ala
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Met Glu Leu Trp Ser Tyr Tyr Phe Asp Tyr Trp Gly Gln
             100                 105                 110

Gly Thr Leu Val Thr Val Ser Ser
             115                 120

<210> SEQ ID NO 6
<211> LENGTH: 107
<212> TYPE: PRT
<213> ORGANISM: Artificial
<220> FEATURE:
<223> OTHER INFORMATION: Humanized murine sequence

<400> SEQUENCE: 6

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Val Ser Tyr Met
                 20                  25                  30

His Trp Tyr Gln Gln Lys Pro Gly Gln Ala Pro Arg Leu Leu Ile Tyr
             35                  40                  45

Asp Thr Ser Lys Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Val Ala Val Tyr Tyr Cys Phe Gln Gly Ser Val Tyr Pro Phe Thr
                 85                  90                  95

Phe Gly Gln Gly Thr Lys Leu Glu Ile Lys Arg
             100                 105

<210> SEQ ID NO 7
<211> LENGTH: 330
<212> TYPE: PRT
<213> ORGANISM: homo sapiens

<400> SEQUENCE: 7

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
```

-continued

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 106
<212> TYPE: PRT
<213> ORGANISM: homo sapiens

<400> SEQUENCE: 8

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 9
<211> LENGTH: 117
<212> TYPE: PRT
<213> ORGANISM: Artificial
<220> FEATURE:
<223> OTHER INFORMATION: heavy chain variable region

<400> SEQUENCE: 9

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Asn Tyr Gly Asn Tyr Trp Phe Ala Tyr Trp Gly Gln Gly Thr Leu
            100                 105                 110

Val Thr Val Ser Ser
            115

<210> SEQ ID NO 10
<211> LENGTH: 111
<212> TYPE: PRT
<213> ORGANISM: Artificial
<220> FEATURE:
<223> OTHER INFORMATION: light chain variable region

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
            85                  90                  95

Glu Asp Pro Trp Thr Phe Gly Gln Gly Thr Lys Val Glu Ile Lys
            100                 105                 110